US012642893B2

(12) United States Patent
Ballard et al.

(10) Patent No.: US 12,642,893 B2
(45) Date of Patent: Jun. 2, 2026

(54) NEEDLE THORACOSTOMY DEVICE AND METHOD OF USE

(71) Applicant: B.I.N.T. Industry, LLC, Benson, AZ (US)

(72) Inventors: Patrick Eugene Ballard, Anchorage, AK (US); Michael James Schmidt, Gilbert, AZ (US); Byron Keith Grice, Tempe, AZ (US); Rawley Charles Evans, Benson, AZ (US)

(73) Assignee: B.I.N.T. INDUSTRY, LLC, Benson, AZ (US)

( * ) Notice: Subject to any disclaimer, the term of this patent is extended or adjusted under 35 U.S.C. 154(b) by 0 days.

(21) Appl. No.: 19/355,884

(22) Filed: Oct. 10, 2025

(65) Prior Publication Data

US 2026/0034278 A1 Feb. 5, 2026

Related U.S. Application Data

(63) Continuation-in-part of application No. PCT/US2024/038414, filed on Jul. 17, 2024.
(Continued)

(51) Int. Cl.
*A61M 1/04* (2006.01)
*A61M 25/06* (2006.01)
(Continued)

(52) U.S. Cl.
CPC .......... *A61M 1/04* (2013.01); *A61M 25/0606* (2013.01); *A61M 39/22* (2013.01);
(Continued)

(58) Field of Classification Search
CPC .... A61M 1/04; A61M 39/22; A61M 25/0606; A61B 2017/3409; A61B 2017/3407; A61B 17/3417; A61B 17/3415; A61B 17/34
See application file for complete search history.

(56) References Cited

U.S. PATENT DOCUMENTS 2,245,350 A 6/1941 Marshall
3,791,386 A 2/1974 McDonald
(Continued)

FOREIGN PATENT DOCUMENTS

WO 2009068661 A1 6/2009

OTHER PUBLICATIONS

Evans, et al., "Prehospital traumatic cardiac arrest: management and outcomes from the Resuscitation Outcomes Consortium Epistry-Trauma and PROPHET registries," J Trauma Acute Care Surg. Aug. 2016 ; 81(2): 285-293. doi:10.1097/TA.0000000000001070.

*Primary Examiner* — Jacqueline F Stephens
(74) *Attorney, Agent, or Firm* — FULLER IP LAW LLC; Rodney J. Fuller; Jeffrey D. Merrill

(57) ABSTRACT

A needle thoracostomy device with a venting device, a deployment device, and a positioning device. The venting device is configured to vent a pleural cavity of a patient. The deployment device is removably attached to the venting device and is configured to perform a needle thoracostomy to attach the venting device to the patient. The deployment device has a release mechanism which, when moved to a released position, allows the deployment device to be separated and lifted away from the venting device. The positioning device is configured to removably engage with at least one of the deployment device and the venting device to correctly position the deployment device and the venting device on the patient for the needle thoracostomy. The positioning device may position the deployment device and the venting device based on anatomical landmarks.

20 Claims, 77 Drawing Sheets

Related U.S. Application Data

(60) Provisional application No. 63/745,683, filed on Jan. 15, 2025, provisional application No. 63/623,771, filed on Jan. 22, 2024, provisional application No. 63/514,070, filed on Jul. 17, 2023.

(51) Int. Cl.
  *A61M 39/22* (2006.01)
  *A61B 17/34* (2006.01)

(52) U.S. Cl.
  CPC ................. *A61B 2017/3407* (2013.01); *A61B 2017/3409* (2013.01)

(56) References Cited

U.S. PATENT DOCUMENTS

| | | | |
|---|---|---|---|
| 4,291,694 A | 9/1981 | Chai | |
| 5,098,388 A | 3/1992 | Kulkashi et al. | |
| 5,256,148 A | 10/1993 | Smith et al. | |
| 5,312,354 A | 5/1994 | Allen et al. | |
| 5,334,159 A | 8/1994 | Turkel | |
| 5,372,588 A | 12/1994 | Farley et al. | |
| 5,725,506 A | 3/1998 | Freeman et al. | |
| 5,997,486 A | 12/1999 | Burek et al. | |
| 6,402,770 B1 | 6/2002 | Jessen | |
| 6,921,387 B2 | 7/2005 | Camrud | |
| 8,439,940 B2 | 5/2013 | Chomas et al. | |
| 8,870,820 B2 | 10/2014 | Murphy et al. | |
| 9,610,131 B2 | 4/2017 | Stoianovici et al. | |
| 9,919,082 B2 | 3/2018 | Harder et al. | |
| 10,028,762 B1 | 7/2018 | Slupchynskyj | |
| 10,595,898 B2 | 3/2020 | Krimsky et al. | |
| 10,758,695 B2 | 9/2020 | Krimsky et al. | |
| 11,058,454 B2 | 7/2021 | Krimsky et al. | |
| 2014/0005604 A1 | 1/2014 | Murphy et al. | |
| 2019/0314561 A1* | 10/2019 | Rhee ................. | A61B 17/3496 |
| 2022/0080160 A1 | 3/2022 | Couzens et al. | |
| 2023/0200847 A1* | 6/2023 | Barton ............... | A61B 17/3423 600/439 |
| 2023/0241353 A1 | 8/2023 | Howell et al. | |

\* cited by examiner

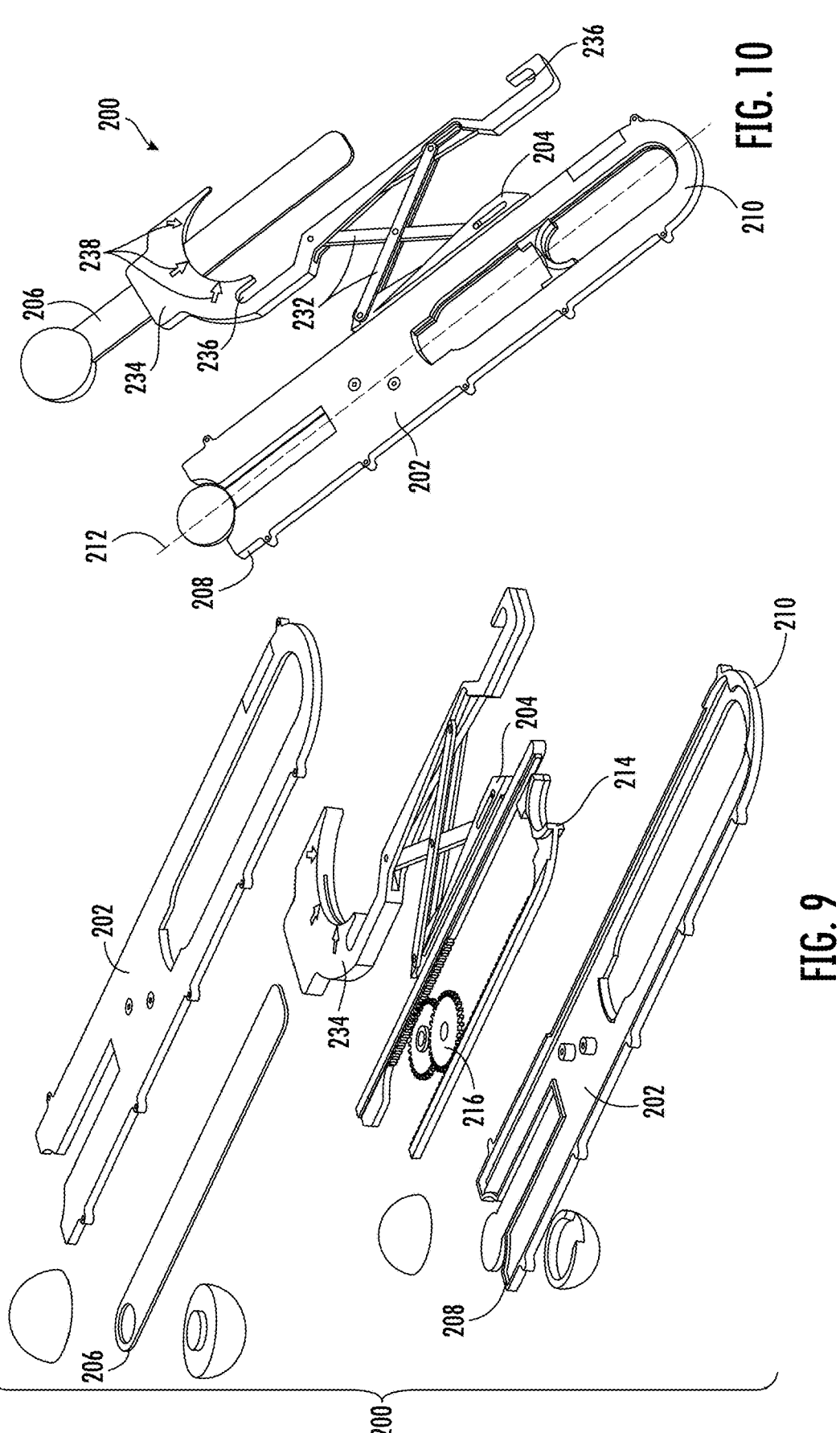

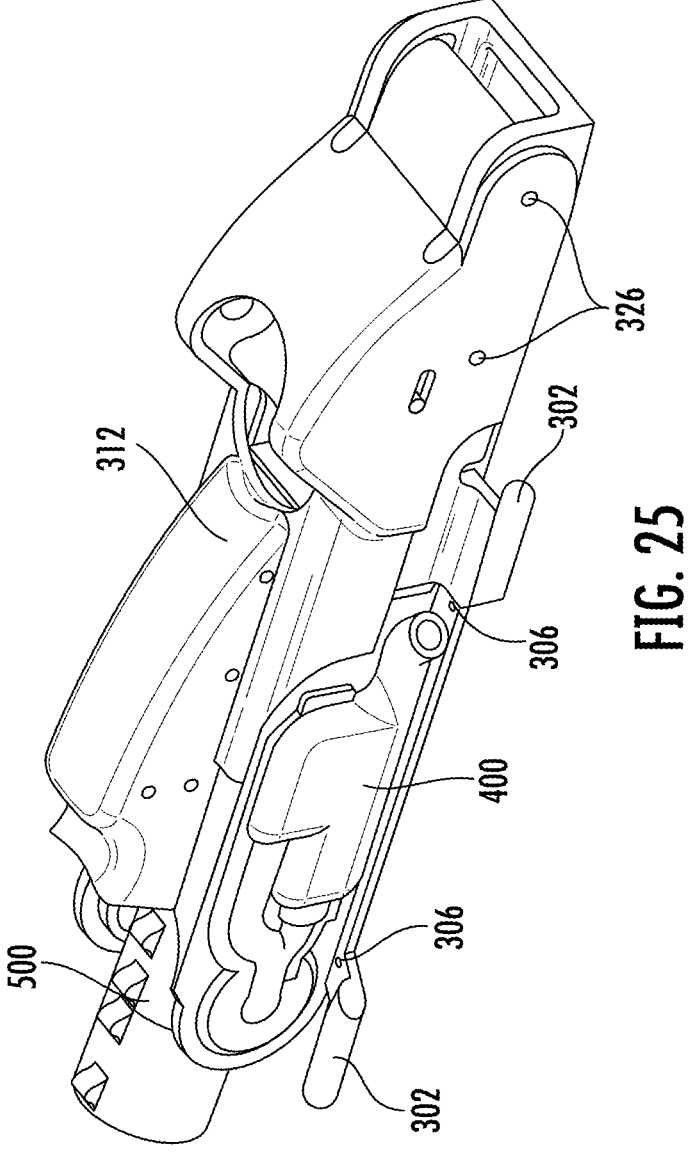
FIG. 25

506

514

516

518

548

552

550

556

556

Anterior axillary line

Midaxillary line 340

Posterior axillary line

342

300

334 { 336 338

1

NEEDLE THORACOSTOMY DEVICE AND METHOD OF USE

RELATED APPLICATIONS

This application is a bypass continuation-in-part of international application no. PCT/US2024/038414, filed on Jul. 17, 2024, which claims the benefit of U.S. provisional patent application 63/514,070, filed Jul. 17, 2023, to Ballard, et al., titled "Needle Thoracostomy Device and Method of Use" and U.S. provisional patent application 63/623,771, filed Jan. 22, 2024, to Ballard, et al., titled "Needle Thoracostomy Device and Method of Use," the entirety of the disclosures of which are hereby incorporated by this reference. This application also claims the benefit of U.S. provisional patent application 63/745,683, filed Jan. 15, 2025, to Ballard, et al., titled "Needle Thoracostomy Device and Method of Use," the entirety of the disclosure of which is hereby incorporated by this reference.

TECHNICAL FIELD

Aspects of this document relate generally to a device for performing a needle thoracostomy, and more specifically to a needle thoracostomy device that simplifies and improves the success rate of the procedure.

BACKGROUND

In emergency medicine, rapid and effective interventions are crucial for managing life-threatening conditions such as tension pneumothorax and hemothorax. Needle thoracostomy, also known as needle decompression, has long been employed as an initial treatment option to relieve the buildup of air or blood in the pleural cavity.

Needle thoracostomy involves the insertion of a large-bore needle into the pleural space to evacuate air or blood. This procedure is typically performed in emergency situations where immediate intervention is required, such as in pre-hospital care, combat medicine, and emergency departments. The procedure aims to rapidly decompress the affected side of the chest, thereby restoring perfusion to the heart, improving ventilation, and relieving potentially life-threatening conditions.

Needle thoracostomy has certain limitations that impact its effectiveness. For example, due to anatomical variations between patients, it can be difficult to know whether the needle has reached the pleural cavity and whether it has been pushed in too far, penetrating into the lung. Inaccurate placement of the needle in the wrong location, such as subcutaneous or intercostal tissues, can impede effective decompression and compromise patient outcomes. Additionally, once placed, the needle is prone to dislodgement or migration due to patient movement, transport, or accidental disconnection from the tubing. Lastly, needle thoracostomy is a challenging procedure to master, particularly in high-stress situations, and inadequate training or experience may increase the risk of complications and reduce success rates. In some cases, those that would perform the procedure may even choose not to do so due to awareness of the likelihood of failure. The effectiveness of this life saving procedure is well documented, but the failure rate of the application is staggering. This leads to apprehension to even perform the procedure. In some cases, those that would perform the procedure may choose not to do so due to awareness of the likelihood of failure, despite the fact that it is currently the standard of care for rapid bilateral needle decompression in post-traumatic codes.

SUMMARY

According to some embodiments, a needle thoracostomy device comprises a base having a first end and a second end, a lever having a first end and a second end, wherein the first end of the lever is hingedly coupled to the second end of the base, and a needle assembly hingedly coupled to the second end of the lever and having a needle and a catheter, wherein the needle thoracostomy device is moveable between a stored position in which the lever and the needle assembly are adjacent the base, a raised position in which the lever is positioned at an oblique angle with respect to the base and the needle assembly extends between the lever and the base, and a deployed position in which the lever is adjacent the base and the needle assembly extends below the base, wherein a hinge joining the lever to the base is configured to allow rotation and linear motion of the lever with respect to the base but constrain both the rotation and the linear motion such that the needle assembly moves along an axis of the needle as the needle thoracostomy device moves from the raised position to the deployed position.

Particular embodiments may comprise one or more of the following features. The device may further comprise a venting system having an outlet and a primary valve configured to drain fluid from the catheter to the outlet and restrict fluid flow from the outlet to the catheter. The venting system may comprise a secondary valve configured to allow fluid from the catheter to bypass the primary valve. The device may further comprise a venting valve positioned adjacent the second end of the lever, the venting valve having a first port and a second port, wherein the venting valve is configured to rotate between a needle position in which the first port is aligned with the catheter and a draining position in which the second port is aligned with the catheter, wherein the venting valve is configured to fluidly couple the catheter to a venting system when in the draining position. The needle may be removable from the needle assembly through the first port and the venting valve may be biased toward the draining position such that the venting valve automatically rotates to the draining position upon removal of the needle from the first port. The base may further have a docking prong configured to position the needle thoracostomy device on a patient with respect to a positioning device configured to position the deployment device on the patient for a needle thoracostomy. The base may be configured to attach to a body of a patient, wherein when in the deployed position, the needle assembly extends into the patient, and wherein the needle is configured to automatically detach from the needle assembly when the needle enters a pleural cavity of the patient.

According to some embodiments, a needle thoracostomy device comprises a venting device configured to vent a pleural cavity of a patient, a deployment device attached to the venting device and configured to perform a needle thoracostomy to attach the venting device to the patient, and a positioning device configured to engage with at least one of the deployment device and the venting device to correctly position the deployment device and the venting device on the patient.

Particular embodiments may comprise one or more of the following features. After the needle thoracostomy has been performed, the deployment device and the positioning device may be removable to leave just the venting device attached to the patient. The deployment device may comprise a release mechanism configured to move between an attached position and a released position, wherein when the deployment device is attached to the venting device and the release mechanism is moved to the released position, the deployment device can be lifted away from the venting device. The positioning device may be configured to fold around the deployment device and the venting device. The positioning device may comprise at least one docking port sized and shaped to receive at least one docking prong on at least one of the deployment device and the venting device, wherein the at least one docking prong comprises a docking prong on the deployment device and a docking prong on the venting device each configured to mate with a different docking port of the at least one docking port on the positioning device. The positioning device may be configured to position the deployment device and the venting device on the patient based on anatomical landmarks.

According to some embodiments, a needle assembly comprises a needle having a hollow body, a plunger positioned within and slidably coupled with the needle, wherein the plunger is configured to move between an extended, inactive position and a retracted, active position, and a blade assembly positioned within the needle affixed to the plunger, wherein the blade assembly is configured to automatically deploy at least one blade when the plunger moves to the retracted, active position.

Particular embodiments may comprise one or more of the following features. The plunger may be biased toward the extended, inactive position. The blade assembly may be configured to automatically retract the at least one blade when the plunger moves to the extended, inactive position. When in the extended, inactive position, the plunger may extend past a sharpened end of the needle and, when in the retracted, active position, the sharpened end of the needle may extend past the plunger. When the plunger reaches a position where the plunger is flush with the sharpened end of the needle, the at least one blade may be at least 75% deployed compared to a maximum deployment of the at least one blade. The at least one blade of the blade assembly may be pivotably coupled to the needle about a pivot point, wherein the pivot point is fixed with respect to the needle. The at least one blade may have a blade channel configured to slidingly engage with a plunger pin coupled to the plunger, wherein the blade channel is shaped to create a nonlinear relationship between a position of the plunger within the needle and deployment of the at least one blade.

Aspects of this document relate to a needle thoracostomy device, comprising a venting device configured to vent a pleural cavity of a patient, a deployment device removably attached to the venting device and configured to perform a needle thoracostomy to attach the venting device to the patient, the deployment device comprising a release mechanism configured to move between an attached position and a released position, wherein when the deployment device is attached to the venting device and the release mechanism is moved to the released position, the deployment device can be lifted away from the venting device, a positioning device configured to removably engage with at least one of the deployment device and the venting device to correctly position the deployment device and the venting device on the patient for the needle thoracostomy based on anatomical landmarks.

Particular embodiments may comprise one or more of the following features. The venting device may have a plurality of suture holes configured to enable attachment of the venting device to the patient with sutures. The positioning device may be configured to fold around the deployment device and the venting device. The positioning device may comprise at least one docking port sized and shaped to receive at least one docking prong on at least one of the deployment device and the venting device. The at least one docking prong may comprise a docking prong on the deployment device and a docking prong on the venting device each configured to mate with a different docking port of the at least one docking port on the positioning device. Lifting the deployment device away from the venting device may allow the at least one docking port of the positioning device to decouple from the at least one docking prong. The release mechanism may comprise a projection and a lock each extending into the venting device, wherein when the release mechanism is in the attached position, the projection and the lock are mated within the venting device and when the release mechanism is in the released position, the lock is removed from the projection. The release mechanism may further comprise a spring aligned with the projection, wherein when the release mechanism is in the released position, the spring is configured to bias the deployment device to detach from the venting device by lifting the projection out of the venting device. The deployment device may comprise a base and a lever movable with respect to the base between a raised position and a stored position, wherein the release mechanism comprises a first internal release mechanism in the base and a second internal release mechanism in the lever. Each of the first internal release mechanism and the second internal release mechanism may comprise a projection and a lock, wherein when the release mechanism is in the attached position, the projection and the lock are mated within the venting device and when the release mechanism is in the released position, the lock is removed from the projection. The second internal release mechanism may operatively interlock with the first internal release mechanism when the lever is in the stored position and disengage with the first internal release mechanism when the lever is in the raised position.

Aspects of this document relate to a needle thoracostomy device, comprising a deployment device configured to perform a needle thoracostomy, and a positioning device configured to engage with the deployment device and correctly position the deployment device on a patient.

Particular embodiments may comprise one or more of the following features. The positioning device may be configured to align with anatomical landmarks to indicate the correct position for the deployment device to perform the needle thoracostomy. The deployment device may have a plurality of suture holes configured to enable attachment of the deployment device to the patient with sutures. The positioning device may be configured to fold around the deployment device. The positioning device may comprise at least one docking port sized and shaped to receive at least one docking prong on the deployment device.

Aspects of this document relate to a needle thoracostomy device, comprising a venting device configured to vent a pleural cavity of a patient, and a deployment device attached to the venting device and configured to perform a needle thoracostomy to attach the venting device to the patient.

Particular embodiments may comprise one or more of the following features. After the needle thoracostomy has been performed, the deployment device may be removable to leave just the venting device attached to the patient. The deployment device may comprise a release mechanism configured to move between an attached position and a released position, wherein when the deployment device is attached to the venting device and the release mechanism is moved to the released position, the deployment device can be lifted away from the venting device. The release mechanism may comprise a projection and a lock each extending into the venting device, wherein when the release mechanism is in the attached position, the projection and the lock are mated within the venting device and when the release mechanism is in the released position, the lock is removed from the projection. The release mechanism may further comprise a spring aligned with the projection, wherein when the release mechanism is in the released position, the spring is configured to bias the deployment device to detach from the venting device by lifting the projection out of the venting device. The deployment device may comprise a base and a lever movable with respect to the base between a raised position and a stored position, wherein the release mechanism comprises a first internal release mechanism in the base and a second internal release mechanism in the lever. Each of the first internal release mechanism and the second internal release mechanism may comprise a projection and a lock, wherein when the release mechanism is in the attached position, the projection and the lock are mated within the venting device and when the release mechanism is in the released position, the lock is removed from the projection. The second internal release mechanism may operatively interlock with the first internal release mechanism when the lever is in the stored position and disengage with the first internal release mechanism when the lever is in the raised position. The venting device may have a plurality of suture holes configured to enable attachment of the venting device to the patient with sutures.

The foregoing and other aspects, features, and advantages will be apparent from the DESCRIPTION and DRAWINGS, and from the CLAIMS if any are included.

BRIEF DESCRIPTION OF THE DRAWINGS

Implementations will hereinafter be described in conjunction with the appended and/or included DRAWINGS, where like designations denote like elements.

FIG. 9 is an exploded view of a positioning device according to some embodiments.

FIG. 10 is a perspective view of a positioning device according to some embodiments.

FIG. 25 is a perspective view of a needle thoracostomy device according to some embodiments.

DETAILED DESCRIPTION

Figure 1:
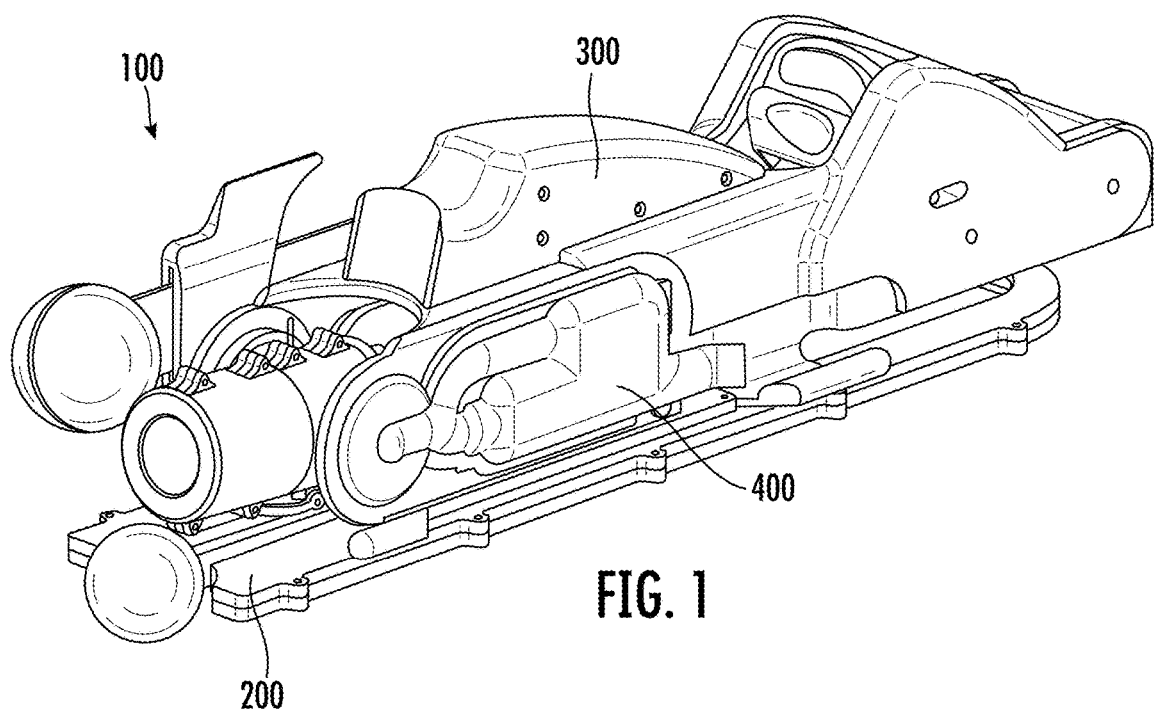
FIG. 1 is a perspective view of a needle thoracostomy device according to some embodiments.
Figure 2:
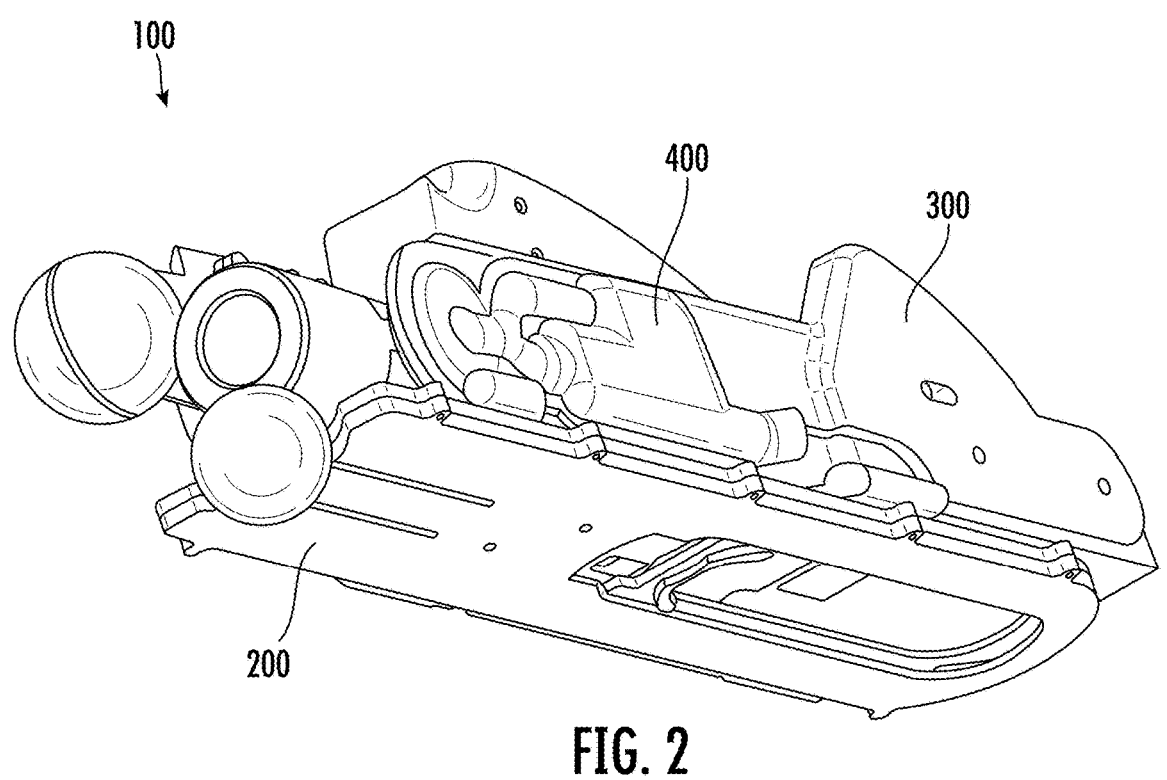
FIG. 2 is a perspective view of a needle thoracostomy device according to some embodiments.
Figure 3:
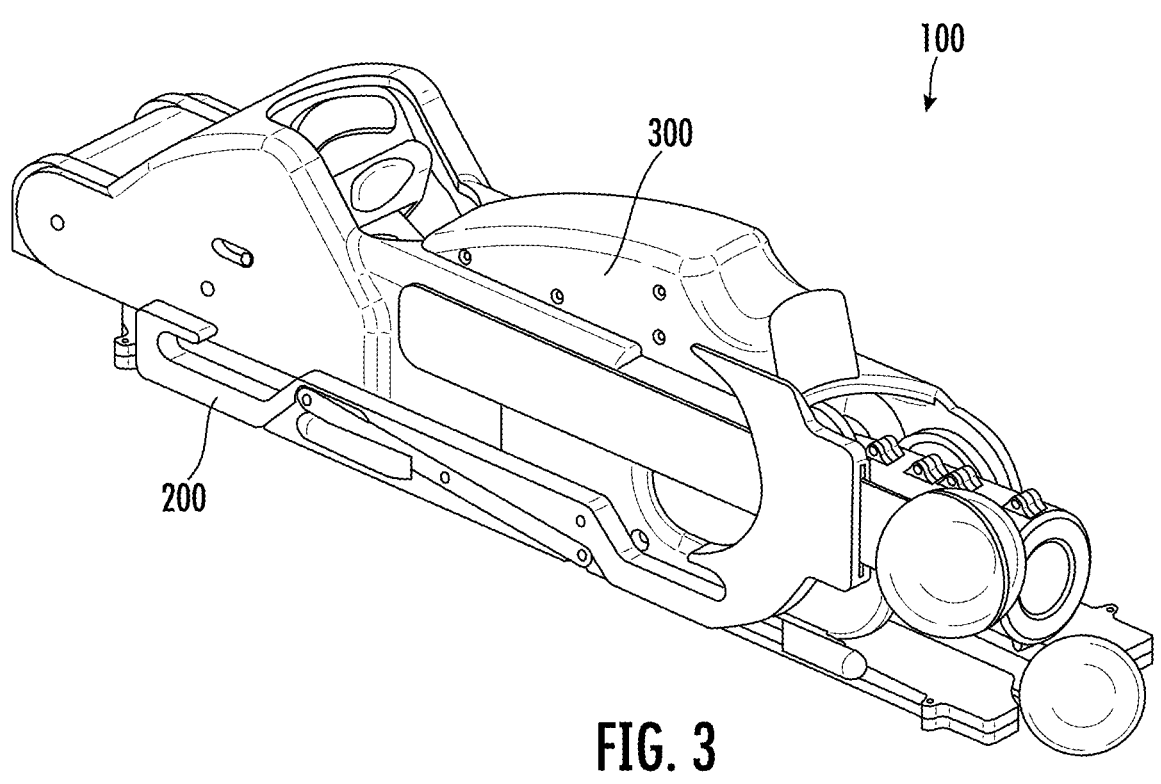
FIG. 3 is a perspective view of a needle thoracostomy device according to some embodiments.
Figure 4:
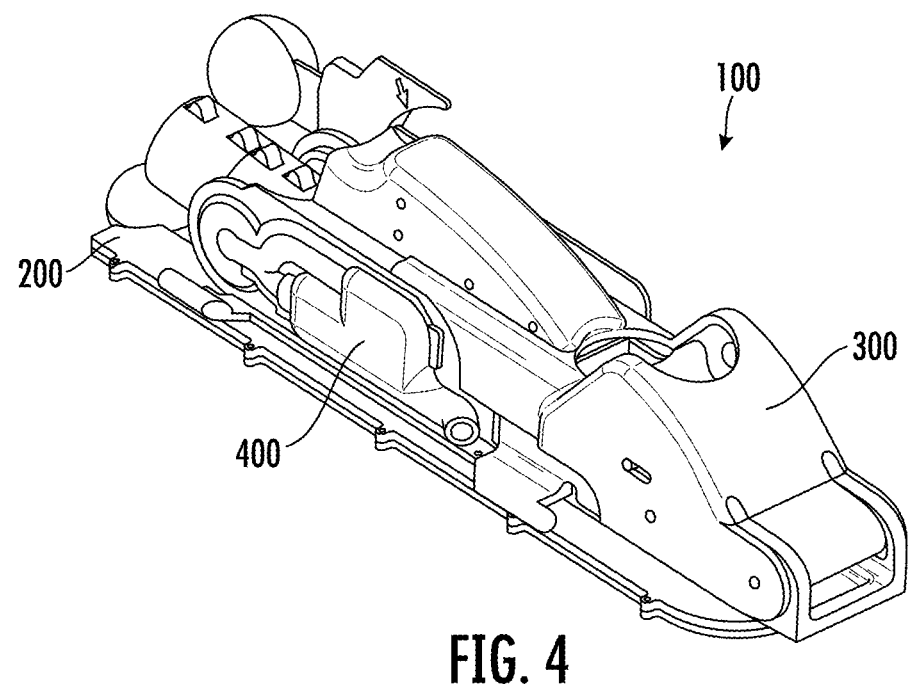
FIG. 4 is a perspective view of a needle thoracostomy device according to some embodiments.
Figures 5, 6:
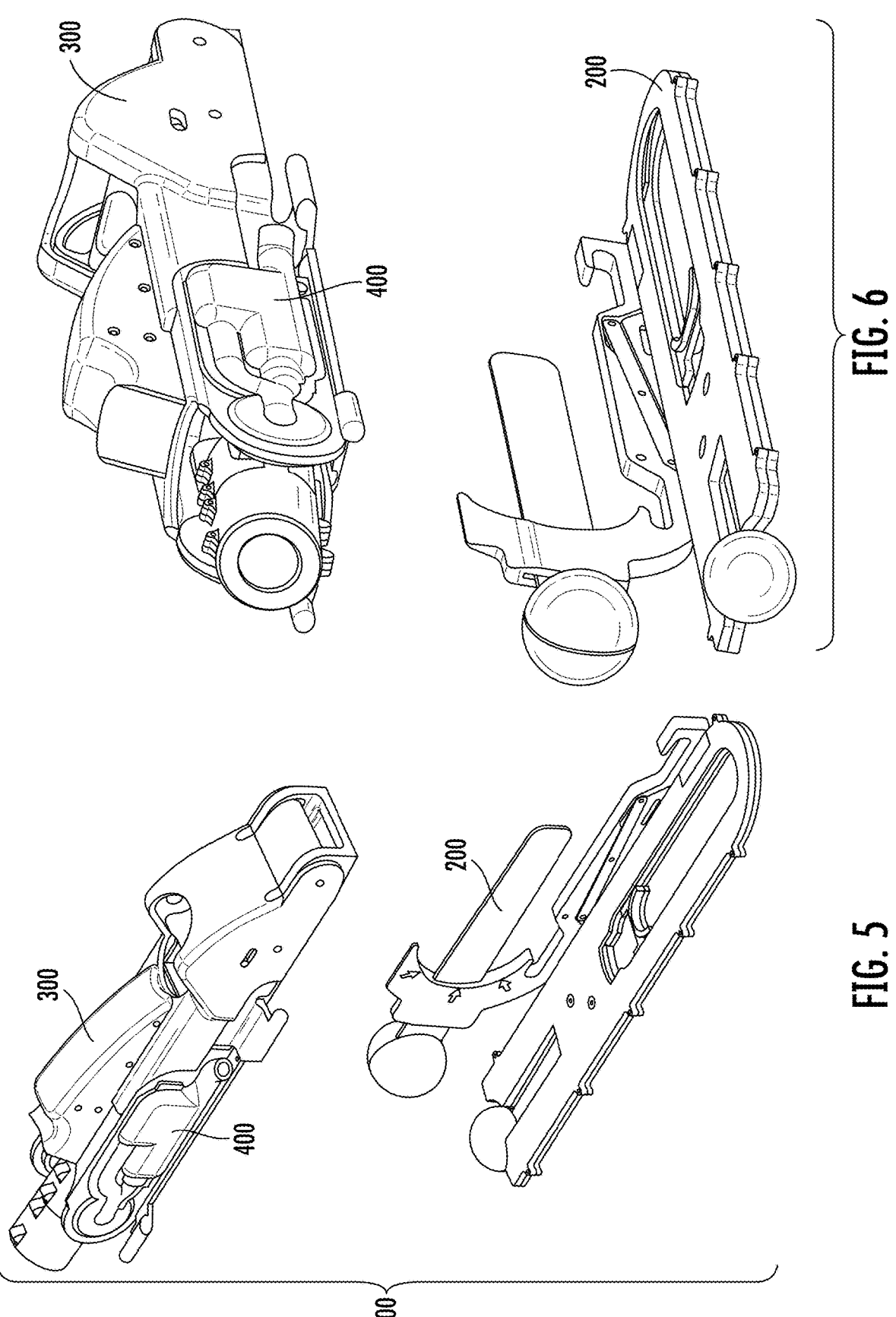
FIG. 5 is an exploded view of a needle thoracostomy device according to some embodiments.
FIG. 6 is an exploded view of a needle thoracostomy device according to some embodiments.

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

Throughout the description and claims of this specification, the words "comprise" and "contain" and variations of the words, for example "comprising" and "comprises", mean "including but not limited to", and are not intended to (and do not) exclude other components.

As required, detailed embodiments of the present disclosure are included herein. It is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the disclosure to be better understood. However, they are given merely by way of guidance and do not imply any limitation.

The present disclosure may be understood more readily by reference to the following detailed description taken in connection with the accompanying figures and examples, which form a part of this disclosure. It is to be understood that this disclosure is not limited to the specific materials, devices, methods, applications, conditions, or parameters described and/or shown herein, and that the terminology used herein is for the purpose of describing particular embodiments by way of example only and is not intended to be limiting of the claimed inventions. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

More specifically, this disclosure, its aspects and embodiments, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The present disclosure is related to a needle thoracostomy device, as well as a method of performing a needle thoracostomy. The needle thoracostomy device is configured for use in treating conditions such as tension pneumothorax, hemothorax, hemopneumothorax, chylothorax, and empyema. The needle thoracostomy device is designed to be small and compact so that it is portable. This allows it to be carried into situations where it can be useful in saving lives, such as during a military operation or a first responder situation. The needle thoracostomy device is also designed to be simpler to effectively use, thus increasing the likelihood that the procedure will be carried out correctly and decreasing the hesitation to use it. This makes it desirable both for military operations as described above and in well-equipped medical facilities, as the needle thoracostomy device improves the effectiveness of the procedure, regardless of the location where it is performed.

The present disclosure is also related to a needle thoracostomy positioning device that is configured to correctly identify and position a deployment device in the optimal location for performing the needle thoracostomy. Though a needle thoracostomy can be effectively carried out in various locations on a patient, in some embodiments, the needle thoracostomy is performed on the chest of the patient. Typically, a patient needs a needle thoracostomy because air has entered the patient's pleural cavity, the space between the lungs and the chest wall. Because air is typically lighter than other fluids within the pleural cavity, it is desirable to perform the needle thoracostomy high up on the patient's chest, as this is typically the highest point on the patient as they rest or recline on their back. Performing the needle thoracostomy high up on the patient's chest helps to drain more air from the patient as a result of the air rising within the patient toward the front upper area of the pleural cavity. Therefore, this disclosure primarily discusses performing the needle thoracostomy in this location, just above the third rib. However, it is to be understood that some embodiments of the needle thoracostomy positioning device may be used in other locations on the body.

As shown in FIGS. 1-6, the needle thoracostomy device 100 may comprise a positioning device 200, a deployment device 300, and/or a venting device 400. Additional embodiments of the needle thoracostomy device are shown throughout the figures, including needle thoracostomy device 101 shown in FIGS. 77-90D. The needle thoracostomy device 101 may have any of the features described herein with respect to any other needle thoracostomy device, including needle thoracostomy device 100. As will be described in more detail below, the venting device 400 is configured to vent a pleural cavity of a patient. The deployment device 300 may be removably attached to the venting device 400 and is configured to perform a needle thoracostomy to attach the venting device 400 to the patient, discussed in more detail below. The positioning device 200 is configured to removably engage with at least one of the deployment device 300 and the venting device 400 to correctly position the deployment device 300 and the venting device 400 on the patient for the needle thoracostomy. The positioning device 200 may be configured to position the deployment device 300 and the venting device 400 based on anatomical landmarks, as discussed in more detail below.

Figure 7:
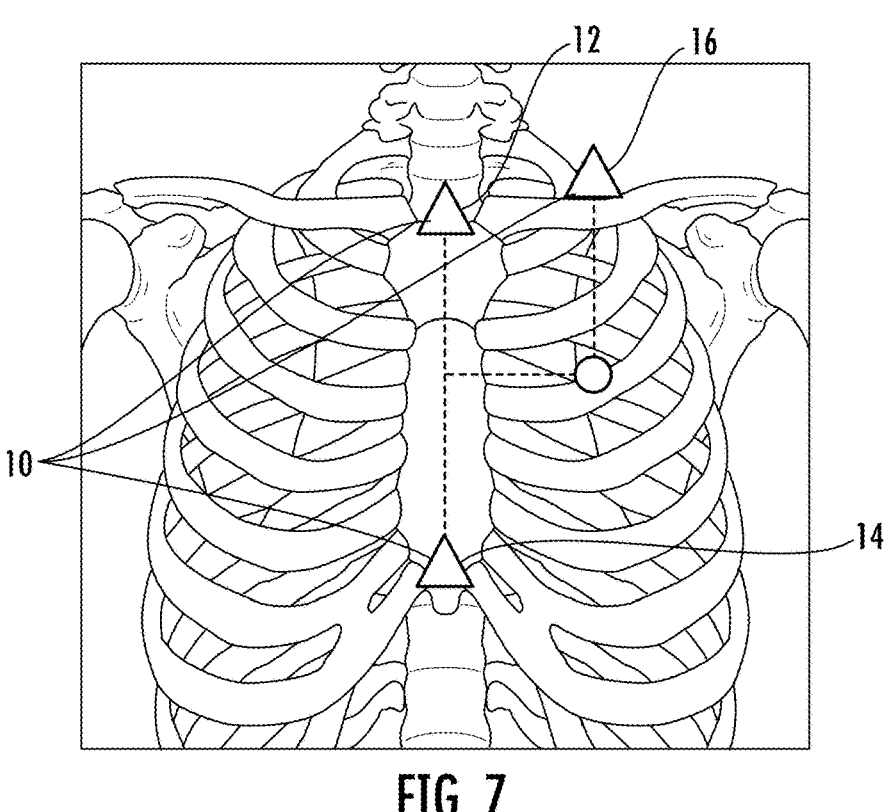
FIG. 7 is a representation of a skeleton to demonstrate desired positioning for a needle thoracostomy according to some embodiments.
Figure 8:
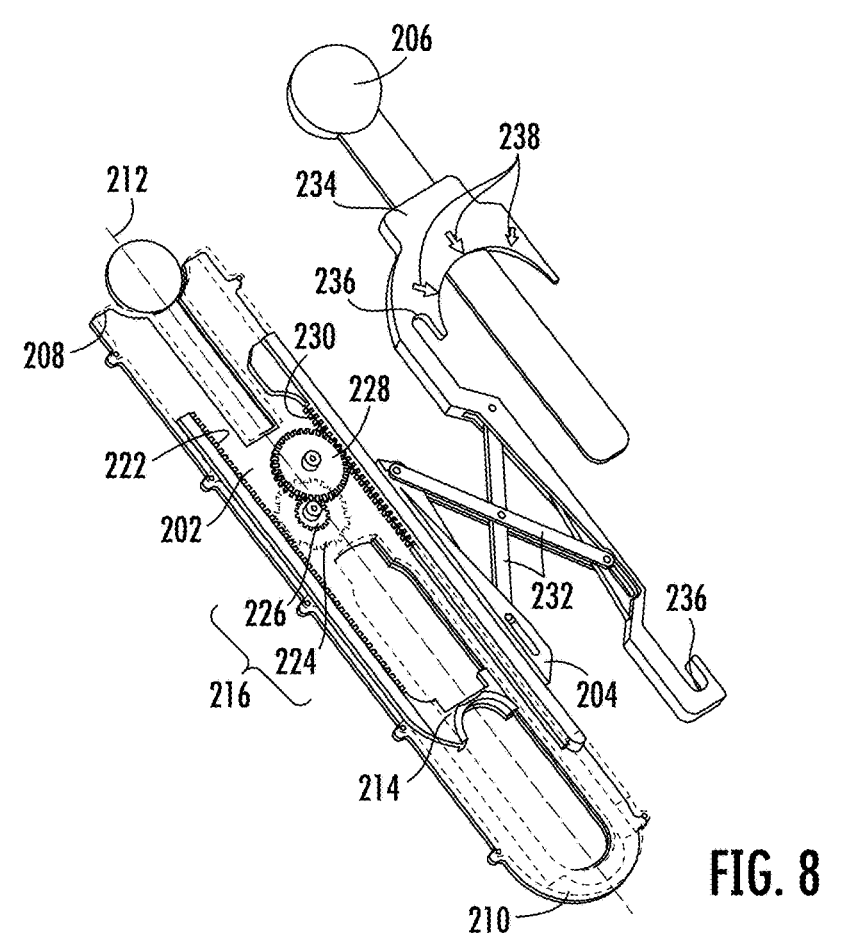
FIG. 8 is a perspective view of a positioning device with interior components shown according to some embodiments.
Figures 11, 12, 13:
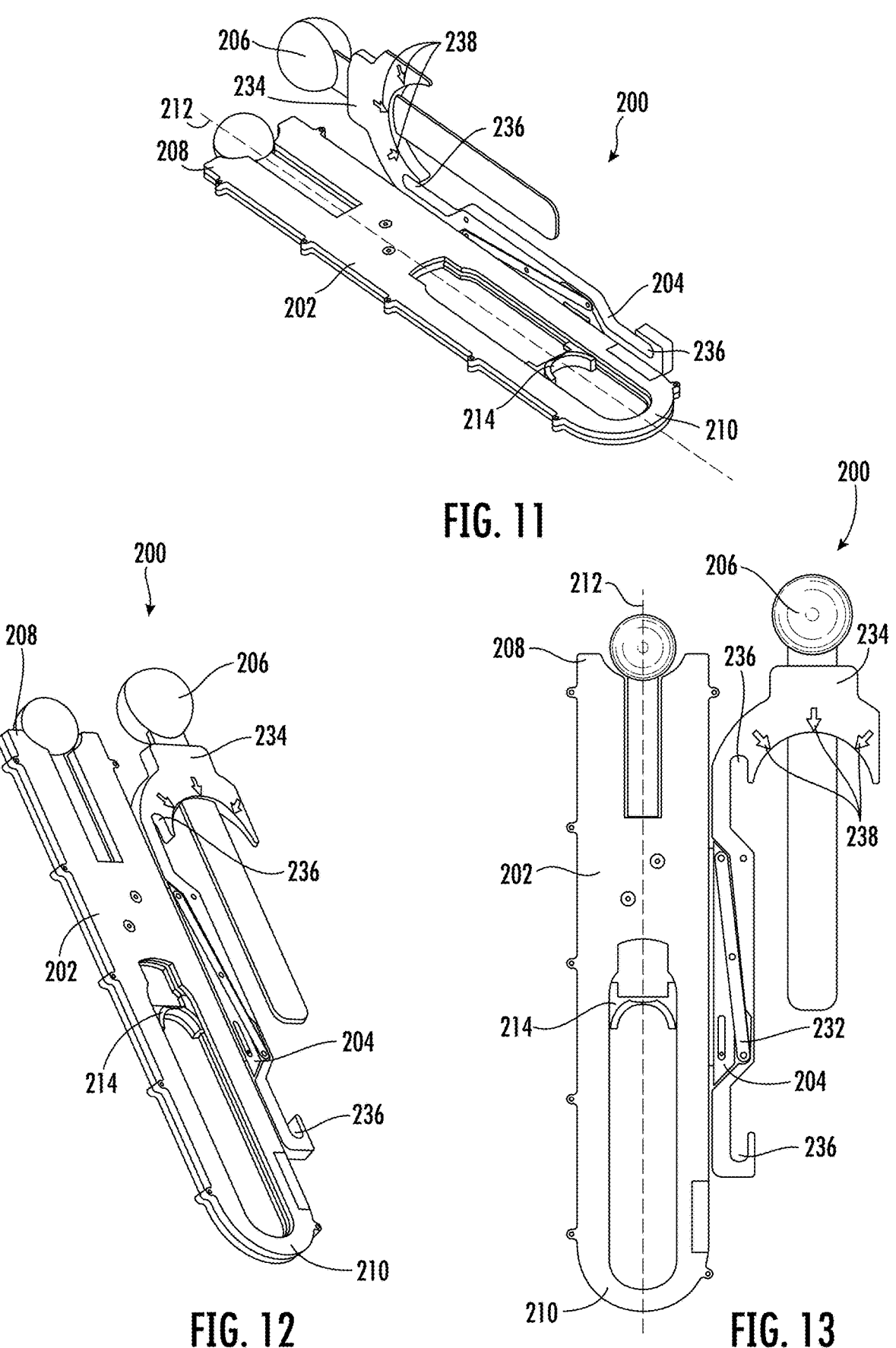
FIG. 11 is a perspective view of a positioning device in a folded configuration according to some embodiments.
FIG. 12 is a perspective view of a positioning device in a flattened configuration according to some embodiments.
FIG. 13 is a front view of a positioning device according to some embodiments.
Figure 15:
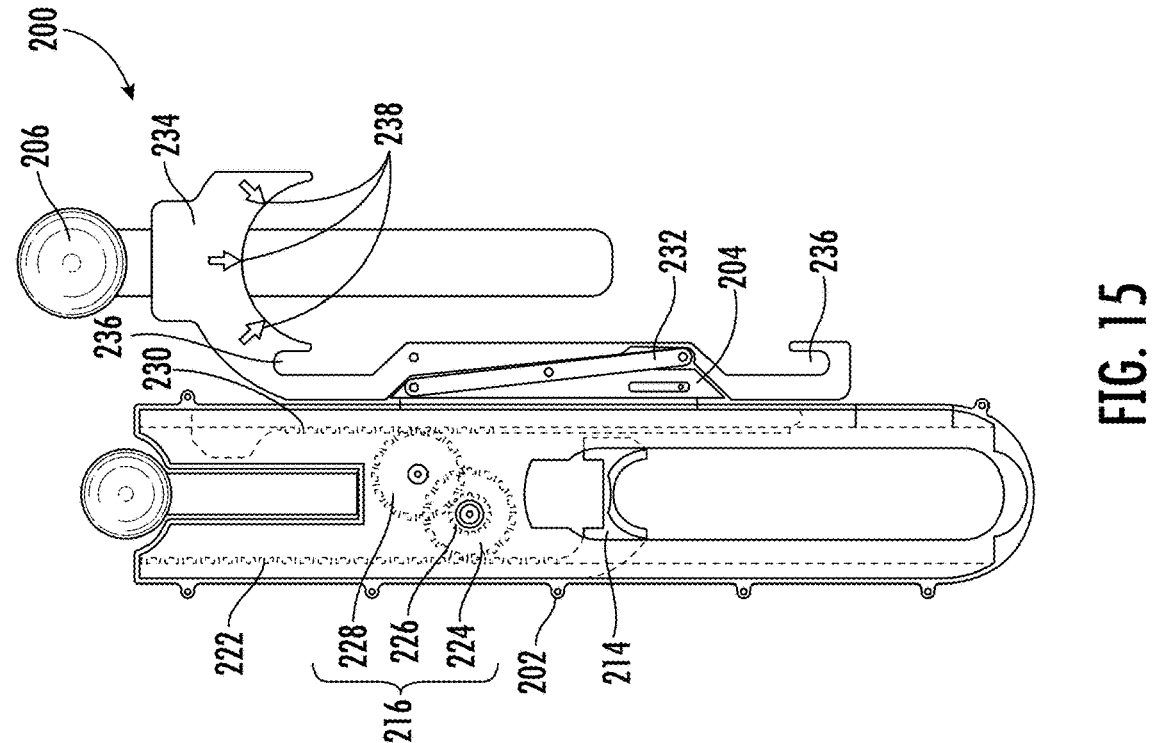
FIG. 15 is a front view of a positioning device with interior components shown according to some embodiments.
Figure 14:
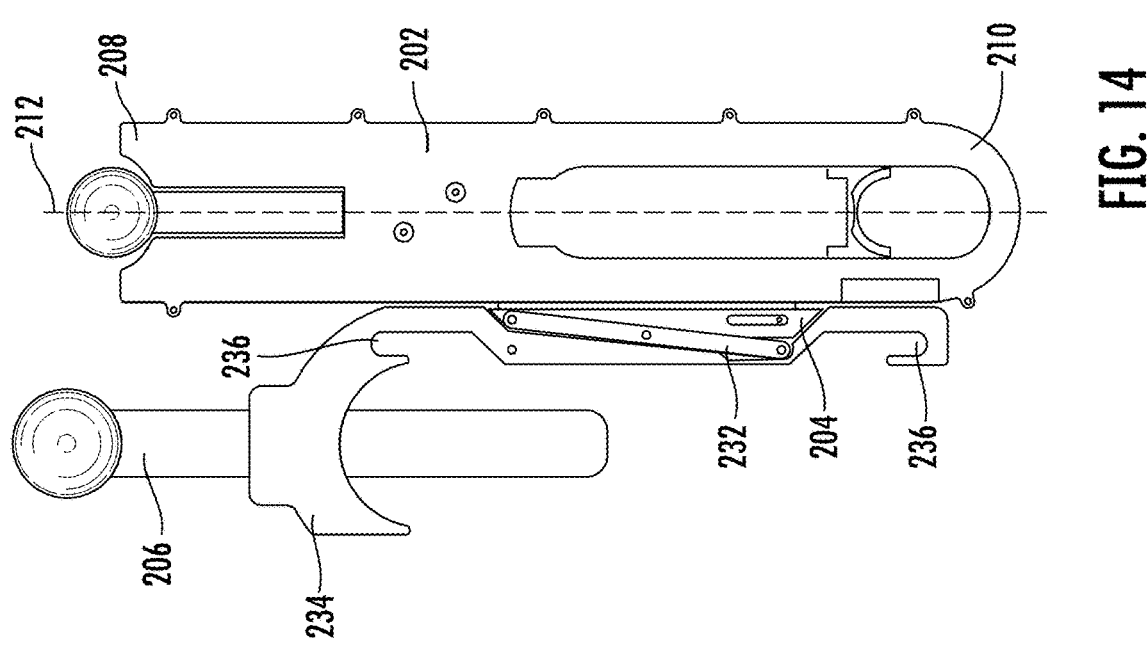
FIG. 14 is a rear view of a positioning device according to some embodiments.
Figure 17:
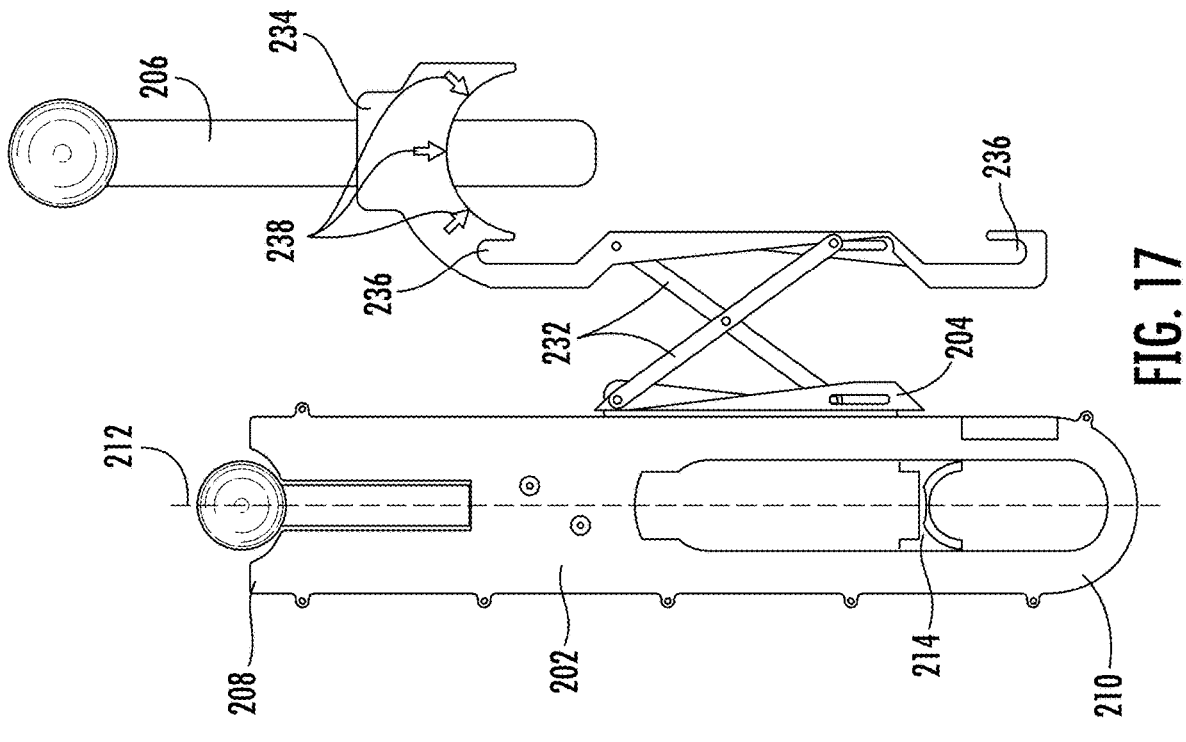
FIG. 17 is a front view of a positioning device with the alignment tool in the extended position according to some embodiments.
Figure 16:
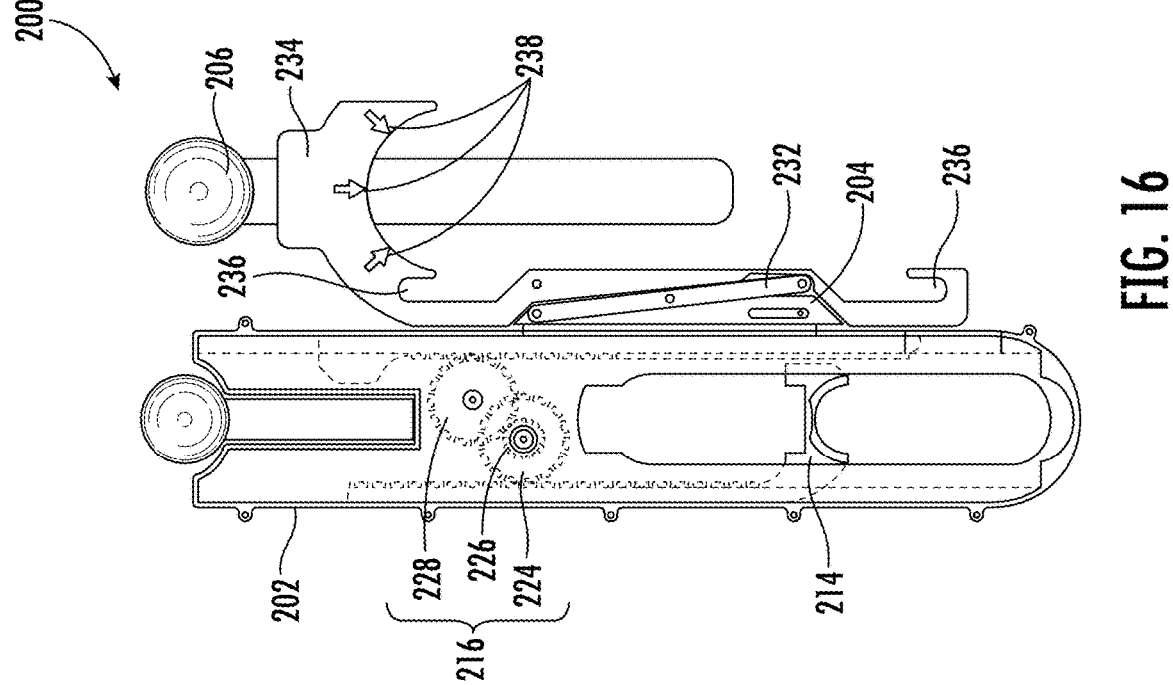
FIG. 16 is a front view of a positioning device with interior components shown and the anatomical indicator lowered toward the second end of the elongated track according to some embodiments.
Figure 19:
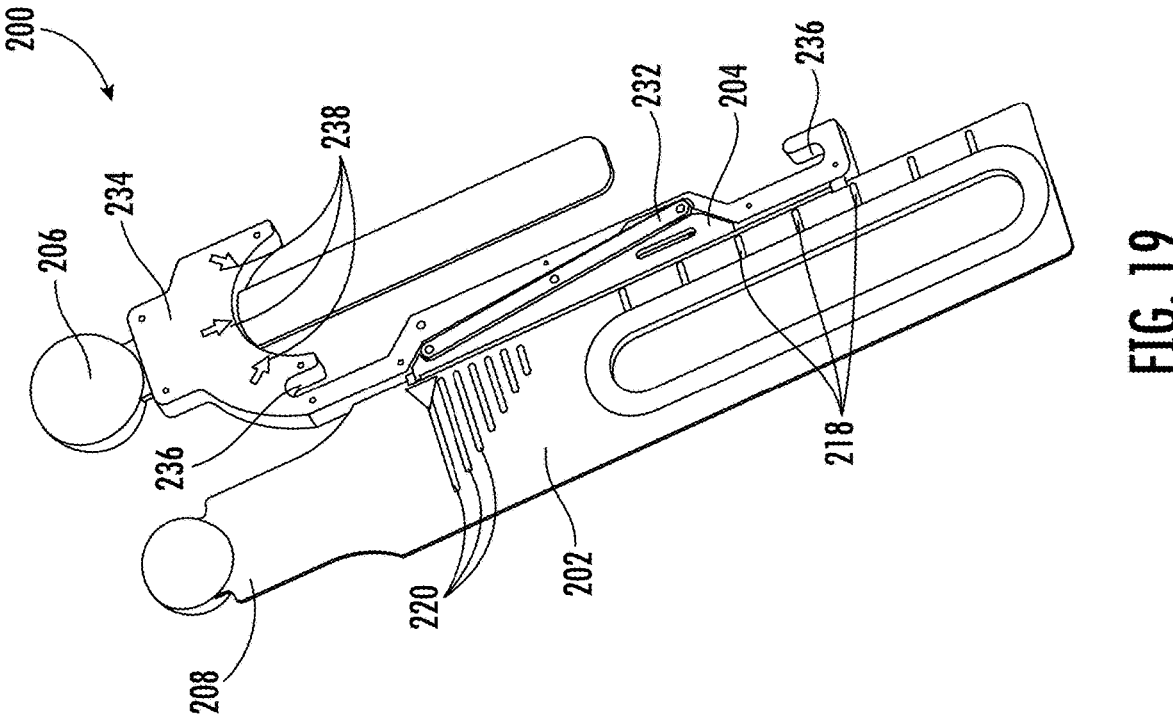
FIG. 19 is a perspective view of a positioning device in a flattened configuration according to some embodiments.
Figure 18:
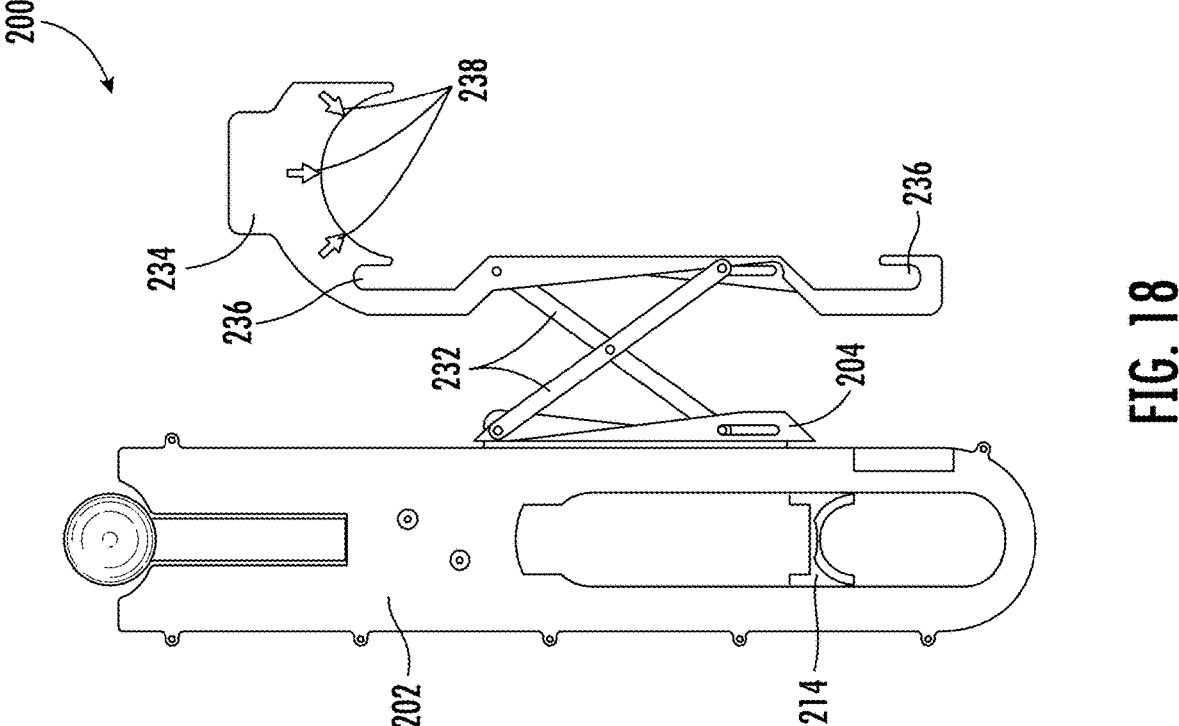
FIG. 18 is a front view of a positioning device with the alignment tool removed according to some embodiments.
Figure 21:
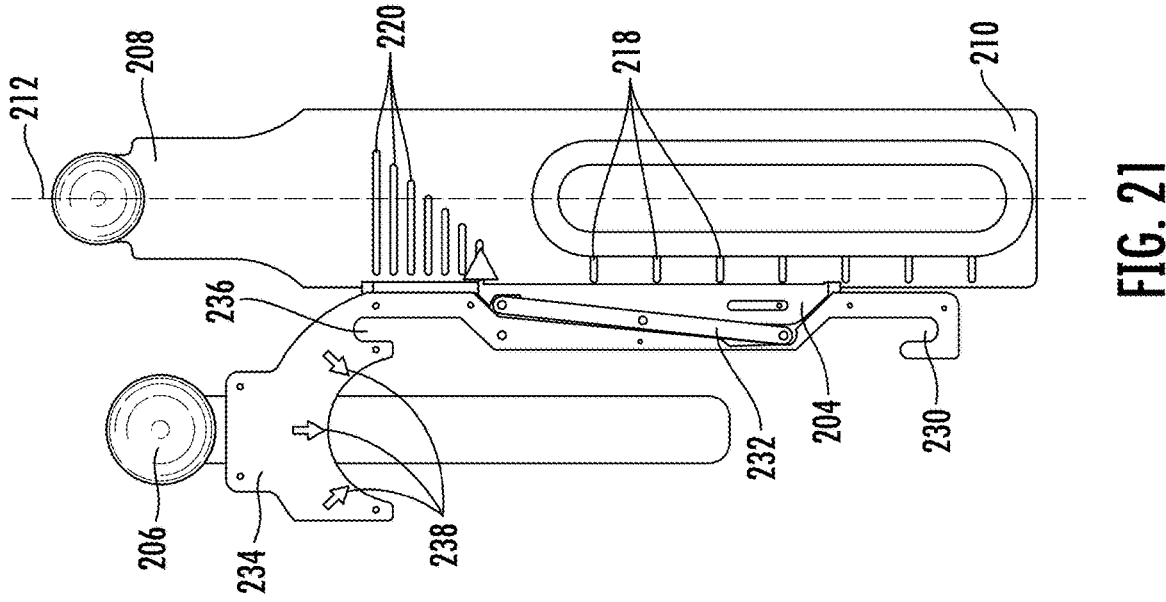
FIG. 21 is a rear view of a positioning device according to some embodiments.
Figure 20:
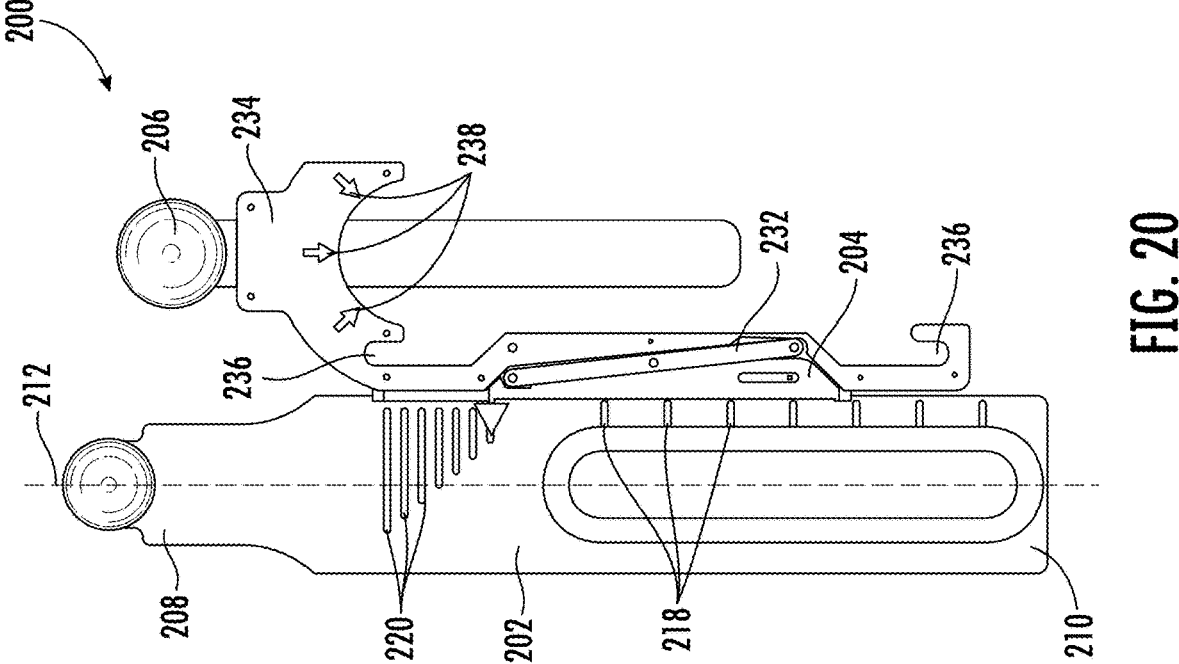
FIG. 20 is a front view of a positioning device according to some embodiments.
Figure 23:
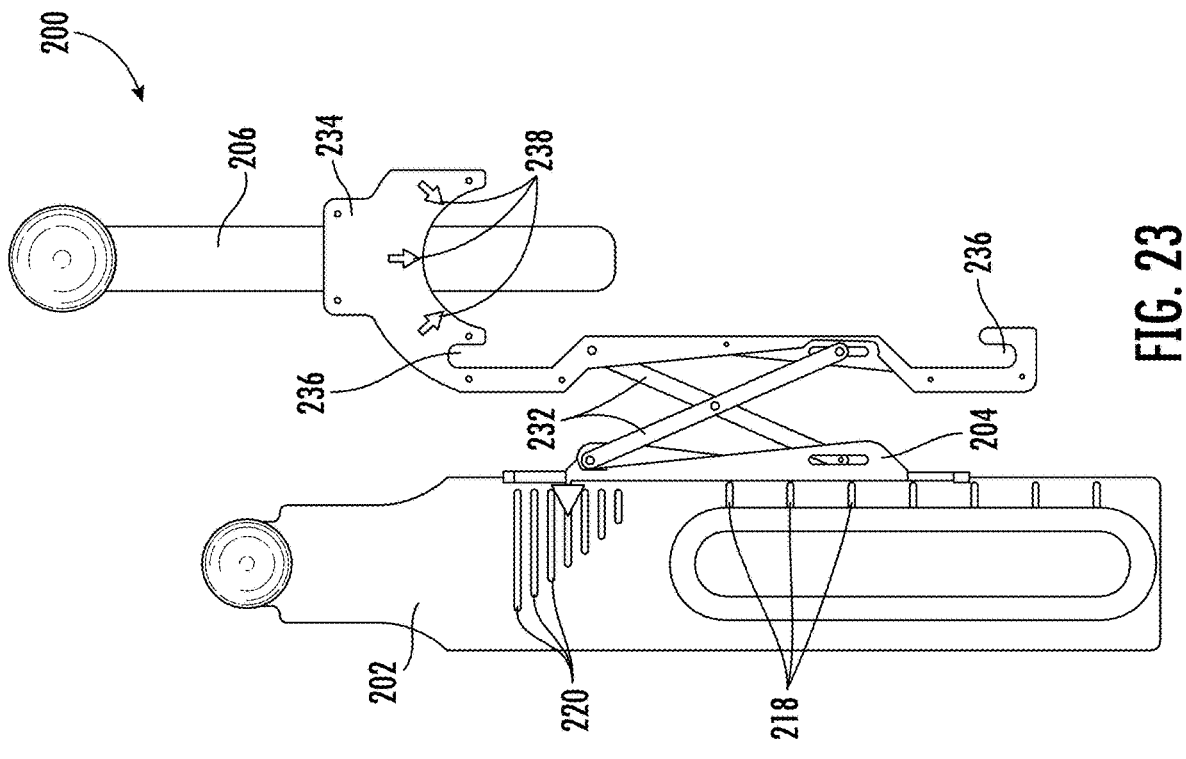
FIG. 23 is a front view of a positioning device with the alignment tool in the extended position according to some embodiments.
Figure 22:
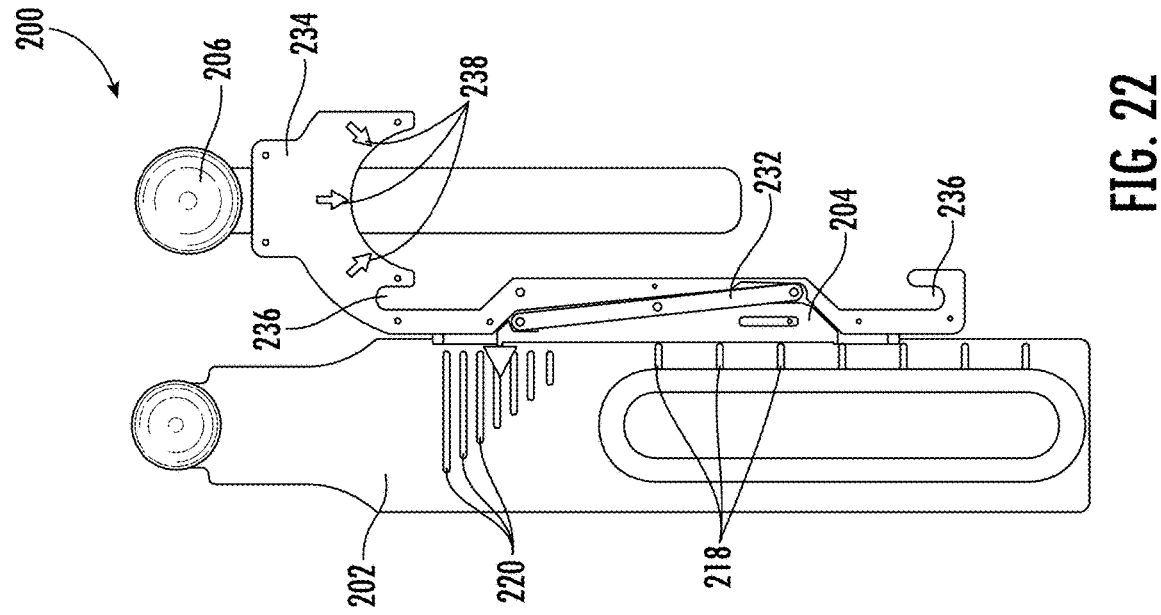
FIG. 22 is a front view of a positioning device with the linear slide lowered toward the second end of the elongated track according to some embodiments.
Figure 24:
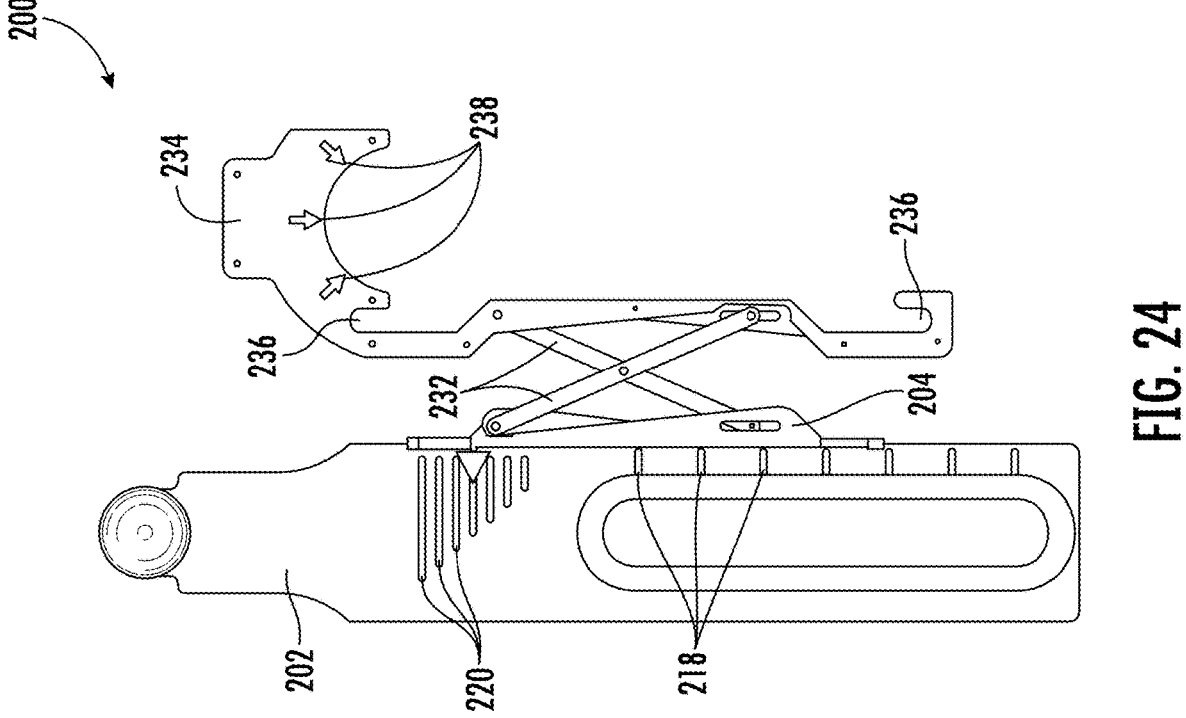
FIG. 24 is a front view of a positioning device with the alignment tool removed according to some embodiments.
Figure 26:
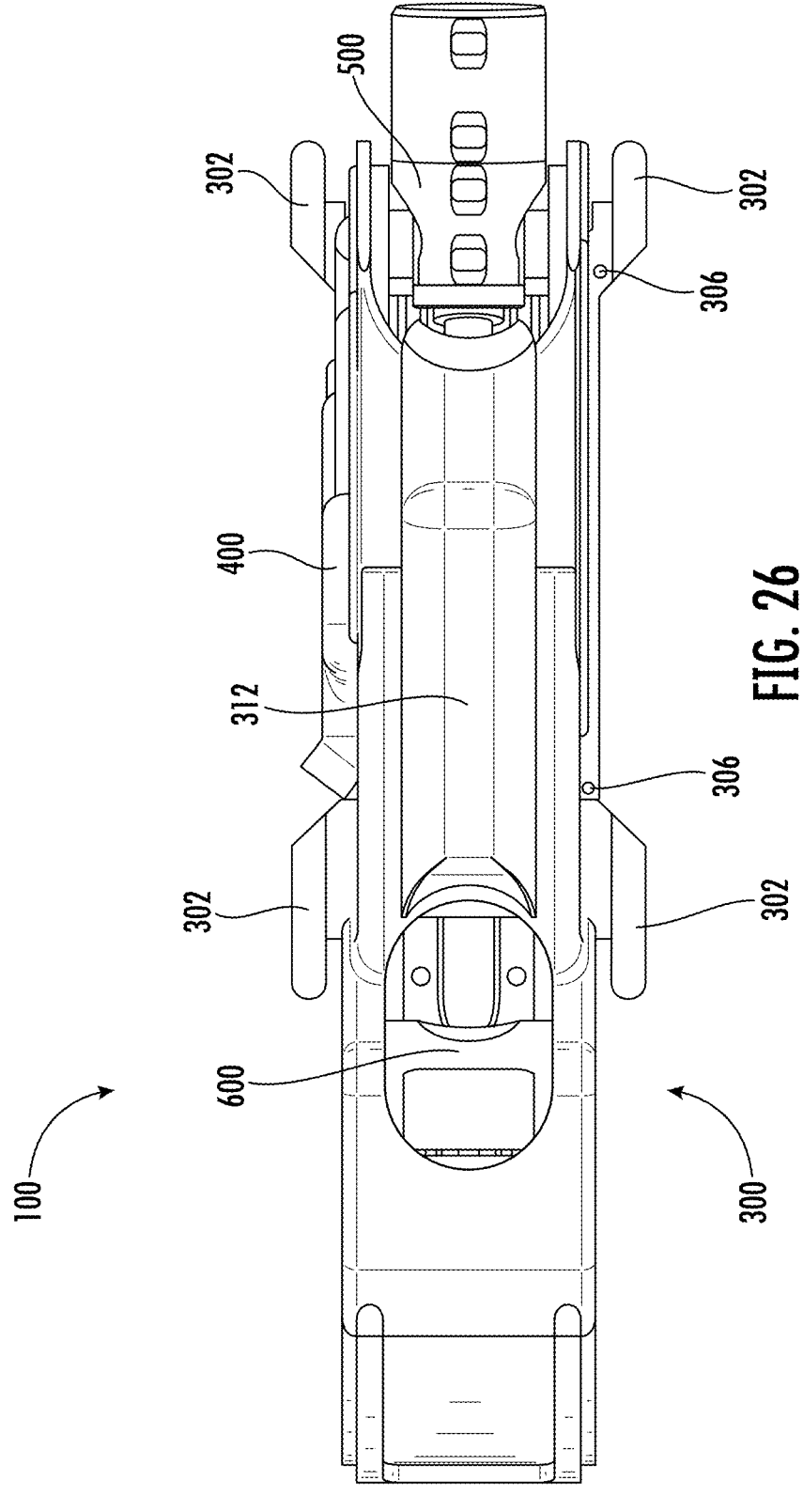
FIG. 26 is a top view of a needle thoracostomy device according to some embodiments.
Figure 27:
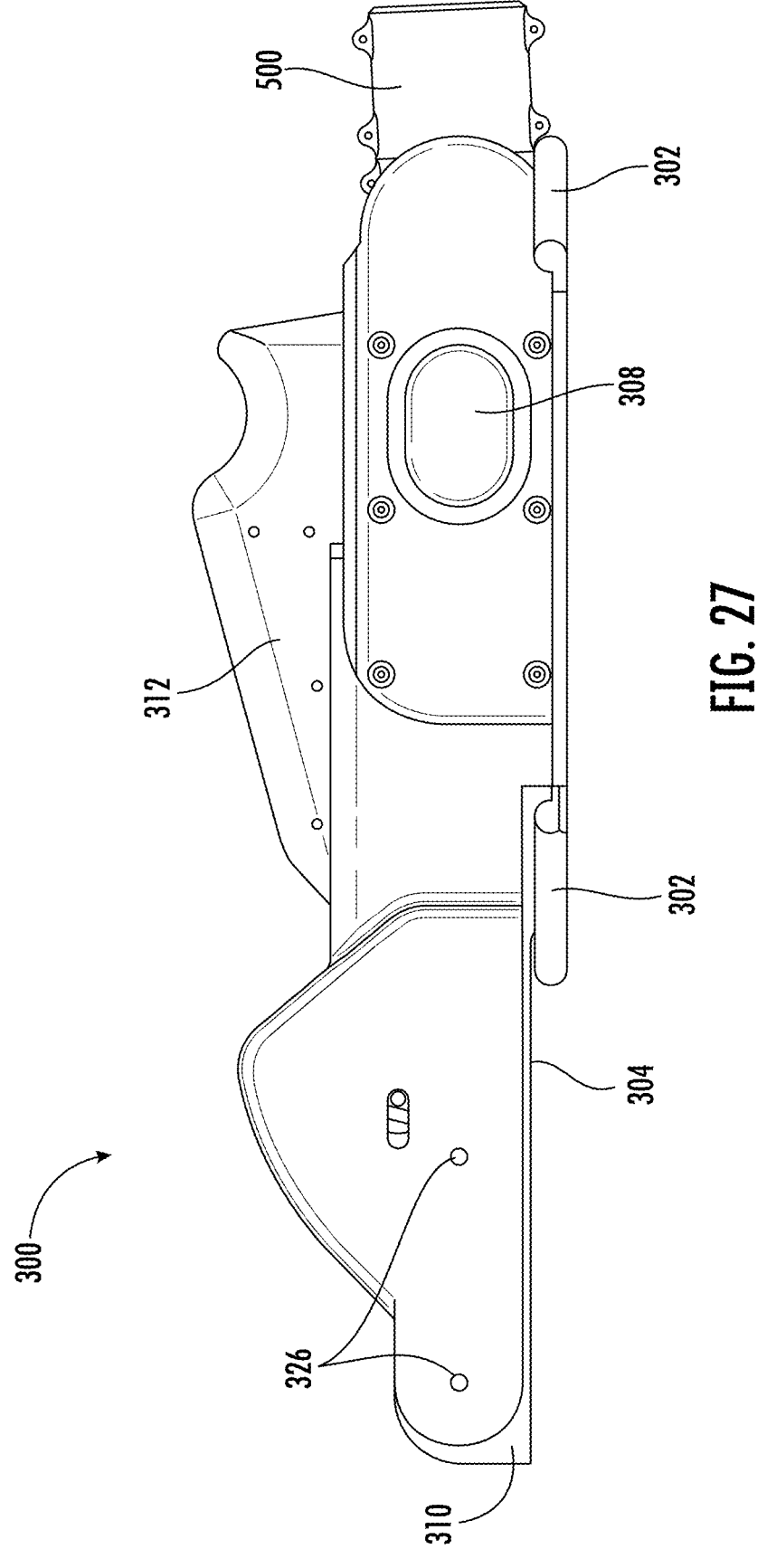
FIG. 27 is a side view of a needle thoracostomy device according to some embodiments.
Figure 28:
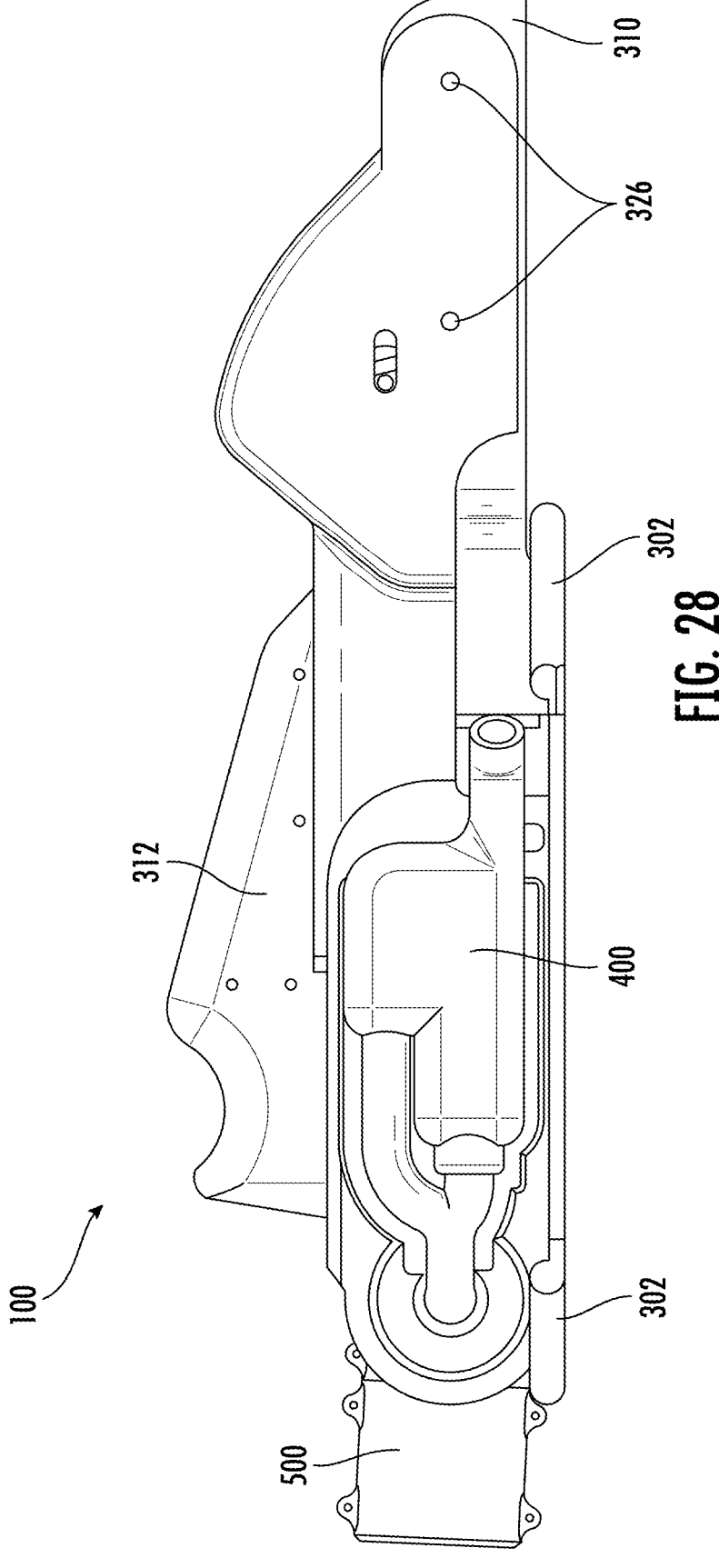
FIG. 28 is a side view of a needle thoracostomy device according to some embodiments.
Figure 30:
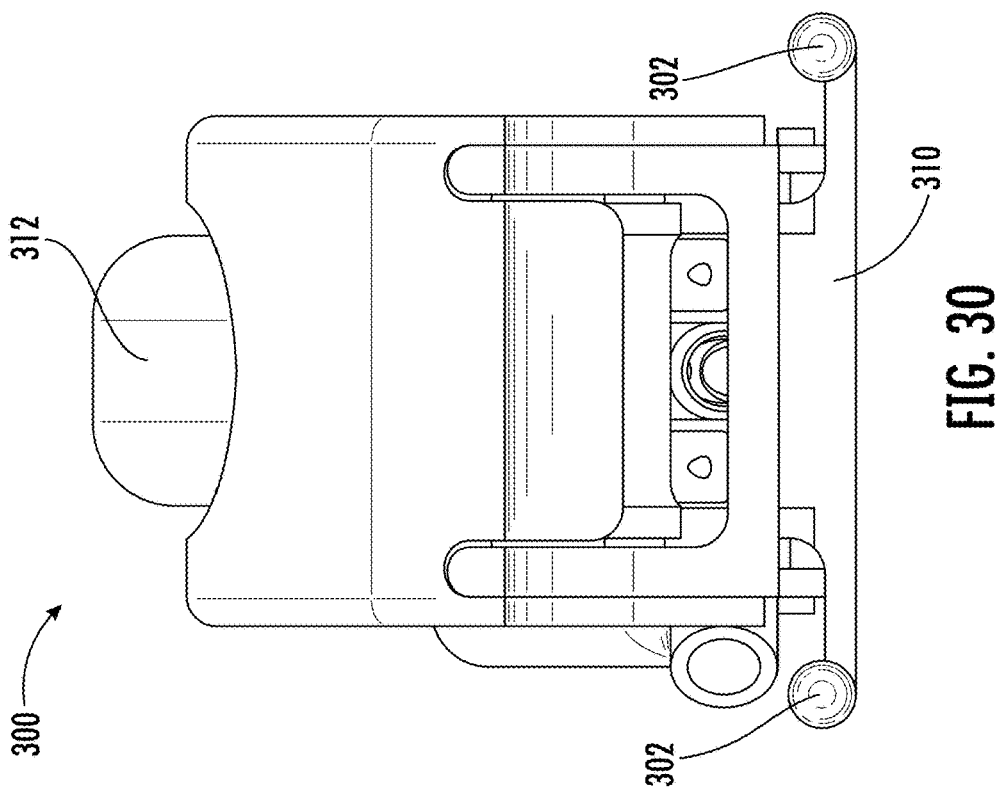
FIG. 30 is a back view of a needle thoracostomy device according to some embodiments.
Figure 29:
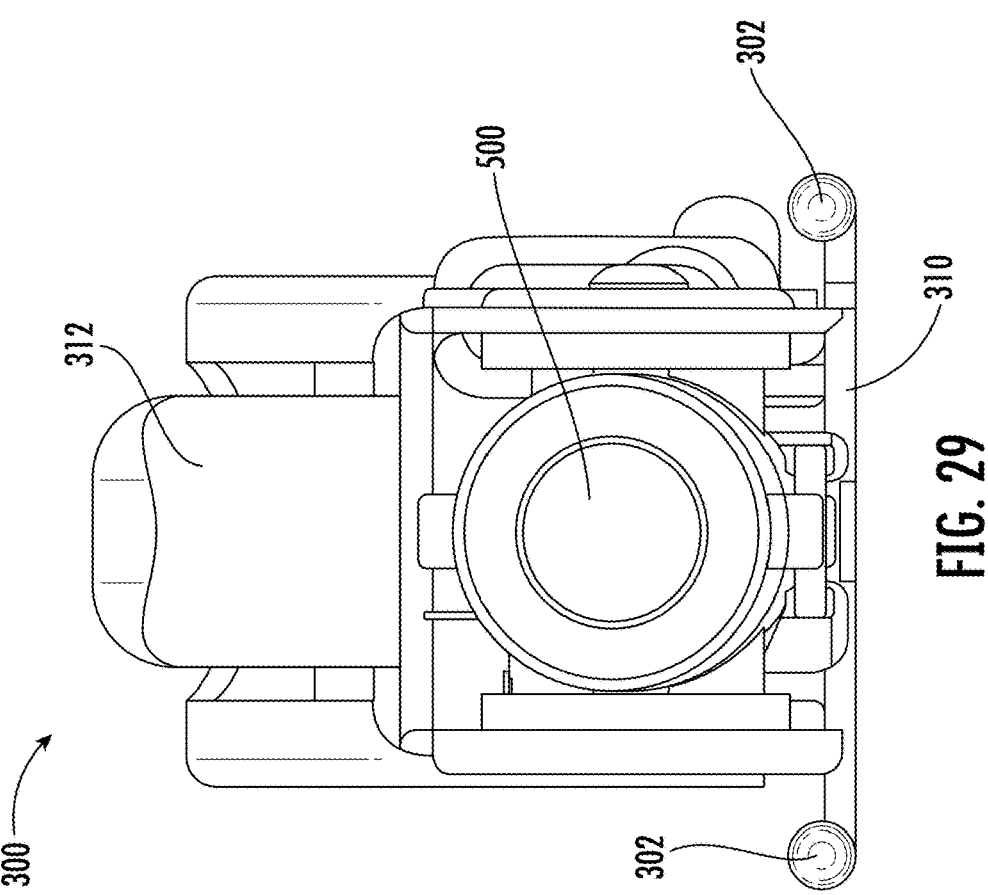
FIG. 29 is a front view of a needle thoracostomy device according to some embodiments.

The goal of the positioning device 200 is to place the deployment device 300 where the needle will insert into the patient, hit the 3rd rib, and glide over the top of it. This helps the needle to enter at the optimal angle and avoids nerves and vessels that extend along the bottoms of the ribs. However, there is a specific area of the third rib that works best for the needle thoracostomy and minimizes the risk of injury to essential organs and arteries. The target area is illustrated in FIG. 7. The positioning device 200 disclosed herein is configured to help an untrained individual locate this area. Rather than requiring the user to know where to position the deployment device 300, the user only needs to identify certain easy-to-find, palpable anatomical landmarks. This is a change from the current theoretical anatomical lines that are used during needle thoracostomies to tactile positions that the user can find by touch.

The present disclosure is related to a positioning device 200, as well as a method of using the positioning device 200 for performing a needle thoracostomy to treat conditions such as tension pneumothorax, hemothorax, hemopneumothorax, chylothorax, and empyema. One method of selecting a procedure site for a needle thoracostomy involves the anatomical landmarks 10 shown in FIG. 7. These anatomical landmarks 10 may include a first anatomical landmark 12, a second anatomical landmark 14, and a third anatomical landmark 16. As will be discussed in more detail below with specific reference to the positioning device 200, in some embodiments, the first anatomical landmark 12 is a jugular notch of the patient, the second anatomical landmark 14 is a xiphoid process of a sternum of the patient, and the third anatomical landmark 16 is a supraclavicular fossa of the patient. Generally, the distance from the jugular notch to the 3rd rib is 37%-40% of the patient's sternum length. Thus, based on general rules about human anatomy, a safe and effective location for the needle thoracostomy can be located by drawing a line between the jugular notch and the xiphoid process (i.e., the sternum length), finding a point about 37%-40% of the way down from the jugular notch along that line, and then moving perpendicular to the line over to a position below the supraclavicular fossa, as shown in FIG. 7. The supraclavicular fossa's medial edge is the lateralmost insertion of the sternocleidomastoideole insertion on the superior surface of the clavicle. This is the medial edge of the theoretical mid-clavicular line that is conventionally used. The supraclavicular fossa can easily be found by running the finger along the top of the clavicle. Once the finger cannot continue along the top of the clavicle, and instead is forced to the front of the clavicle, this is the supraclavicular fossa. Thus, the supraclavicular fossa acts as an appropriate substitute for aligning the alignment tool with the center line of the clavicle and is much easier to find by simple touch. Using the supraclavicular fossa as a guide point also ensures that the needle thoracostomy occurs lateral to the internal thoracic artery and major pulmonary vessels, thus avoiding damage to these organs. Some embodiments of the positioning device 200 are configured to facilitate locating this point and are configured to position the deployment device 300 lateral to the internal thoracic artery and major pulmonary vessels. Using the positioning device 200 takes the guesswork out of selecting the procedure site, instead only requiring the user to locate the anatomical landmarks 10, all of which are palpable and easy to locate based on simple instructions.

As illustrated by the embodiments shown in FIGS. 8-24, the positioning device 200 comprises an elongated track 202, a linear slide 204, and an alignment tool 206. The linear slide 204 may be slidably coupled to the elongated track 202, allowing the linear slide 204 to move along the elongated track 202. The alignment tool 206 may be mounted to the linear slide 204 such that the alignment tool 206 moves with the linear slide 204.

The elongated track 202 is configured to be placed on the chest of the patient. The elongated track 202 has a first end 208 and a second end 210 opposite the first end 208, with a centerline 212 extending between the first end 208 and the second end 210. The first end 208 is configured to be positioned on the first anatomical landmark 12 of the patient. The second end 210 of the elongated track 202 is then aligned to point towards the second anatomical landmark 14 of the patient. This aligns the centerline 212 of the elongated track 202 with the line between the first anatomical landmark 12 and the second anatomical landmark 14. For example, the first end 208 may be positioned on the jugular notch of the patient and the second end 210 may be oriented towards the xiphoid process of the patient to align the centerline 212 of the elongated track 202 with the sternum of the patient.

In some embodiments, the linear slide 204 is slidably coupled to the elongated track 202. This allows the linear slide 204 to be moved to a desired location that is aligned with the third rib as discussed above. The linear slide 204 may be configured to move parallel with the centerline 212 of the elongated track 202. Depending on the embodiment of the positioning device 200, movement of the linear slide 204 to the desired location may be accomplished in different ways. For example, as shown in FIGS. 8-18, the positioning device 200 may comprise an anatomical indicator 214 that is slidably coupled to the elongated track 202. The anatomical indicator 214 is operatively coupled to the linear slide 204 through a plurality of gears 216 or some other gear reduction ratio structure. The relationship between the position of the linear slide 204 and the anatomical indicator 214 may be such that at any given moment, the linear slide 204 is positioned a predetermined percentage of the distance from the first end 208 of the elongated track 202 to the anatomical indicator 214. Similarly, the plurality of gears 216 couples the linear slide 204 to the anatomical indicator 214 such that a distance covered by the linear slide 204 is a predetermined percentage of a distance covered by the anatomical indicator 214.

As shown, the anatomical indicator 214 may have a plurality of teeth 222 that are configured to engage with a first gear 224 of the plurality of gears 216. The first gear 224 may be fixed to a second gear 226, which is smaller, such that the first gear 224 and the second gear 226 rotate together. The second gear 226 may be configured to engage with a third gear 228, which in turn engages with a plurality of teeth 230 on the linear slide 204. In this way, the motion of the anatomical indicator 214 is transferred to the linear slide 204, but the plurality of gears 216 reduces the motion of the linear slide 204 so that the linear slide 204 does not travel to the same extent that the anatomical indicator 214 travels.

The predetermined percentage may correlate with the typical ratio between the vertical distance from the first anatomical landmark 12 to the third rib and the vertical distance from the first anatomical landmark 12 to the second anatomical landmark 14. Thus, the predetermined percentage may be between 37% and 40%. In some embodiments, the predetermined percentage may be between 20%-50%, 25%-50%, 30%-45%, or 37%-40%. Moving the anatomical indicator 214 along the elongated track 202 causes the linear slide 204 to move with respect to the elongated track 202 as well. Thus, as the anatomical indicator 214 is moved away from the first end 208 of the elongated track 202, the linear slide 204 is configured to move to maintain a position at the predetermined percentage of the distance from the first end 208 of the elongated track 202 to the anatomical indicator 214, even as this distance changes. The user can therefore move the anatomical indicator 214 down to the second anatomical landmark 14, such as the xiphoid process. In such embodiments, when the first end 208 of the elongated track 202 is on the first anatomical landmark 12 and the anatomical indicator 214 in on the second anatomical landmark 14, the linear slide 204 is aligned with where the third rib of the patient should be located.

As another example of how the linear slide 204 may be moved to a desired location that is aligned with the third rib as discussed above, the elongated track 202 may comprise anatomical markings 218 and corresponding anatomical markings 220 each spaced along the elongated track 202, as illustrated in FIGS. 19-24. The anatomical markings 218 and the corresponding anatomical markings 220 together are configured to visually indicate to the user where to place the linear slide 204. In use, the user may place a finger on the second anatomical landmark 14 of the patient and make note of which anatomical marking 218 is closest to the finger. Then the user may manually move the linear slide 204 to the corresponding anatomical marking 220, which is positioned to be at the predetermined percentage along the elongated track 202 with respect to the anatomical marking 218. This places the linear slide 204 in the desired location aligned with the third rib of the patient.

As mentioned above, the alignment tool 206 may be mounted to the linear slide 204 such that the alignment tool 206 moves with the linear slide 204. In addition, the alignment tool 206 may be movable in a direction noncollinear with the centerline 212 of the elongated track 202. This allows the alignment tool 206 to move away from the centerline 212 to align with the third anatomical landmark 16. In some embodiments, the alignment tool 206 is mounted through a plurality of structural members 232 that are hingedly coupled to the elongated track 202 and to the alignment tool 206 or to a structure supporting the alignment tool 206 (such as the docking frame 234 discussed below). The plurality of structural members 232 allows the alignment tool 206 to be moved freely toward and away from the elongated track 202, as shown in FIGS. 17, 18, 23, and 24. Other mechanisms for mounting the alignment tool 206 to the linear slide 204 will be apparent to one of skill in the art. Thus, the alignment tool 206 may be moveable between a central position (FIGS. 12-16 and 19-22) and an extended position (FIGS. 17, 18, 23, and 24). The extended position may be based on alignment with the third anatomical landmark 16. In other words, once the linear slide 204 has been correctly positioned as described above, the alignment tool 206 can be extended out to align with the third anatomical landmark 16, thus indicating the procedure site for the needle thoracostomy to the user. The alignment tool 206 may be removable from the positioning device 200. Removing the alignment tool 206 makes space for the deployment device 300 to be used with the positioning device 200 to perform the needle thoracostomy.

An important feature of the positioning device 200 is that, the positioning device 200 holds the deployment device 300 to the side so that the deployment device 300 cannot be positioned too close to the center of the patient. If the needle 506 were deployed too close to the center of the patient, there would be increased risk of damage to the intrathoracic artery, pulmonary vasculature, or other organs of the patient. The positioning device 200 thus acts as a safety feature that reduces this risk because the closest the deployment device 300 can get to the center of the patient is when the positioning device 200 is in the central position.

The positioning device 200 may also comprise a docking frame 234. In some embodiments, the docking frame 234 is mounted to the linear slide 204 with the alignment tool 206. In some embodiments, the docking frame 234 is mounted to the linear slide 204 and the alignment tool 206 is mounted to the docking frame 234. The docking frame 234 is configured to position the deployment device 300 on the patient to perform the needle thoracostomy. In some embodiments, the docking frame 234 is sized and shaped to receive a docking prong 302 of a deployment device 300. In some embodiments, the docking frame 234 has a docking port 236 that is configured to mate with a docking prong 302 on the deployment device 300 or on the venting device 400. This allows the positioning device 200 to position the deployment device 300 more precisely in the desired procedure site. In some embodiments, the docking frame 234 has a docking port 236 configured to mate with a docking prong 302 on the deployment device 300 and a docking port 236 configured to mate with a docking prong 302 on the venting device 400. This allows the deployment device 300 and the venting device 400 to lock in to the positioning device 200 until the deployment device 300 is separated from the venting device 400 (see FIGS. 66 and 71), at which point the deployment device 300 can be lifted away, and then the positioning device 200 can slide off of the venting device 400.

In some embodiments, the positioning device 200 comprises a docking frame 235, which may have any of the same features and capabilities as the docking frame 234. In some embodiments, the docking frame 235 is sized and shaped to receive a docking prong 303 of a deployment device 300. The docking frame 235 may comprise pads 237 that are configured to couple with the docking prongs 303 on the deployment device 300, as shown in FIGS. 90A-90D. The docking prongs 303 may comprise magnets 305, thus making the docking prongs 303 magnetic. In some embodiments, the pads 237 are metal and/or comprise metal. Thus, the docking prongs 303 may be magnetically attracted to the pads 237 when placed near the docking frame 235. In some embodiments, this causes the docking prongs 303 to make an audible noise or a tactile click or snap when coupling with the docking frame 235. This may help the user to feel confident that the deployment device 300 has been properly coupled with the positioning device 200. In some embodiments, the docking prongs 303 and/or the pads 237 are colored differently, such as yellow, orange, or red, to help indicate their location and make the process of coupling the deployment device 300 to the positioning device 200 more intuitive. In some embodiments, the location of the magnets and the magnetic material are interchangeable. For example, in some embodiments, the magnets 305 are positioned on the docking prongs 303 and the pads 237 comprise magnetic material such as metal. In other embodiments, the magnets 305 are positioned on the pads 237 and the docking prongs 303 comprise magnetic material such as metal. In some embodiments, both the docking prongs 303 and the pads 237 comprise magnets 305.

The docking frame 234 may comprise one or more anesthesia indicators 238. The one or more anesthesia indicators 238 are configured to indicate potential sites for local anesthesia, such as lidocaine ("lido"). This may help to instruct the user on where to inject the anesthesia to numb the skin prior to performing the needle thoracostomy and removes the need for the user to decide where local anesthesia would be appropriate.

The positioning device 200 may have adhesive on a surface of the positioning device 200 to be used once different portions of the positioning device 200 are properly positioned. The adhesive is configured to attach the positioning device 200 to the patient. In some embodiments, the adhesive is covered until needed, at which point the covering can be removed to attach the positioning device 200 to the patient. This allows the positioning device 200 to be placed where desired, and then attached to the patient when ready. Multiple coverings may also be implemented such that different portions of the positioning device 200 can be attached to the patient at different times. For example, the elongated track 202 may be attached before extending the alignment tool 206 out to the extended position. Once the alignment tool 206 is also properly positioned, it can also be attached to the patient. This allows the positioning device 200 to remain in place during the needle thoracostomy and until the user desires to remove the positioning device 200 from the patient.

As stated above, the positioning device 200 is configured to help the user to locate the proper location for the needle thoracostomy and position the deployment device 300 in that location. Depending on the circumstances, the needle thoracostomy may need to be performed on the right side of the patient or on the left side. Therefore, in some embodiments, the positioning device 200 is adaptable to be used on a left side and on a right side of the patient by flipping the positioning device 200 over, and may be implemented on either the left side or the right side of the patient. In this way, the positioning device 200 may be reversible.

The positioning device 200 is designed to be small and compact so that it is portable. This allows it to be carried into situations where it can be useful in saving lives, such as during a military operation or a first responder situation. In some embodiments, the positioning device 200 is configured to fold up to a 90 degree angle, as shown in FIGS. 1-6 and 11. This allows the positioning device 200 to be contained in a smaller space without requiring such a complex hinge that it can be folded 180 degrees. To conserve space, the positioning device 200 may be folded around the deployment device 300 and/or the venting device 400 that are to be used with the positioning device 200. This allows the needle thoracostomy device 100 to be packaged in a smaller space. The positioning device 200 is also designed to be easy to effectively use, thus increasing the likelihood that the procedure will be carried out in the correct position and decreasing the hesitation to use it. This makes it desirable both for military operations as described above and in well-equipped medical facilities, as the positioning device 200 improves the effectiveness of the procedure.

The present disclosure is also related to a method of selecting a procedure site for a needle thoracostomy. The method may comprise providing a positioning device 200 as described above. The first end 208 of the elongated track 202 of the positioning device 200 may be positioned on a first anatomical landmark 12 of the patient. The elongated track 202 may be aligned with a second anatomical landmark 14 of the patient. The linear slide 204 may be slid away from the first end 208 of the elongated track 202 to a desired location that is based on the second anatomical landmark 14. The alignment tool 206 may be moved to an extended position aligned with a third anatomical landmark 16 of the patient.

The method may also comprise sliding the anatomical indicator 214 that is operatively coupled to the linear slide 204 away from the first end 208 of the elongated track 202 to the second anatomical landmark 14. The method may also comprise indicating potential sites for local anesthesia with the positioning device 200 prior to the needle thoracostomy, removing the alignment tool 206 from the positioning device 200, and/or attaching the positioning device 200 to the patient.

The present disclosure is also related to a method of selecting a procedure site of a needle thoracostomy that comprises positioning a first component of a positioning device 200 on a patient based on a first anatomical landmark 12 of the patient, adjusting a position of a second component of the positioning device 200 with respect to the first component based on a second anatomical landmark 14 of the patient, adjusting a position of a third component of the positioning device 200 with respect to the first component and the second component on the patient based on a third anatomical landmark 16 of the patient, and identifying the procedure site for the needle thoracostomy using the positioning device 200.

In such a method, the first anatomical landmark 12 may be a jugular notch of the patient, the second anatomical landmark 14 may be a xiphoid process of a sternum of the patient, and/or the third anatomical landmark 16 may be a supraclavicular fossa of the patient. Similarly, the first component may be an elongated track 202, the second component may be a linear slide 204, and/or the third component may be an alignment tool 206. Adjusting the position of the second component with respect to the first component may comprise sliding an anatomical indicator 214 operatively coupled to the second component away from a first end 208 of the first component to the second anatomical landmark 14. The method may also comprise indicating potential sites for local anesthesia with the positioning device 200 prior to the needle thoracostomy, removing the third component from the positioning device 200, and/or attaching the positioning device 200 to the patient.

Figure 89B:
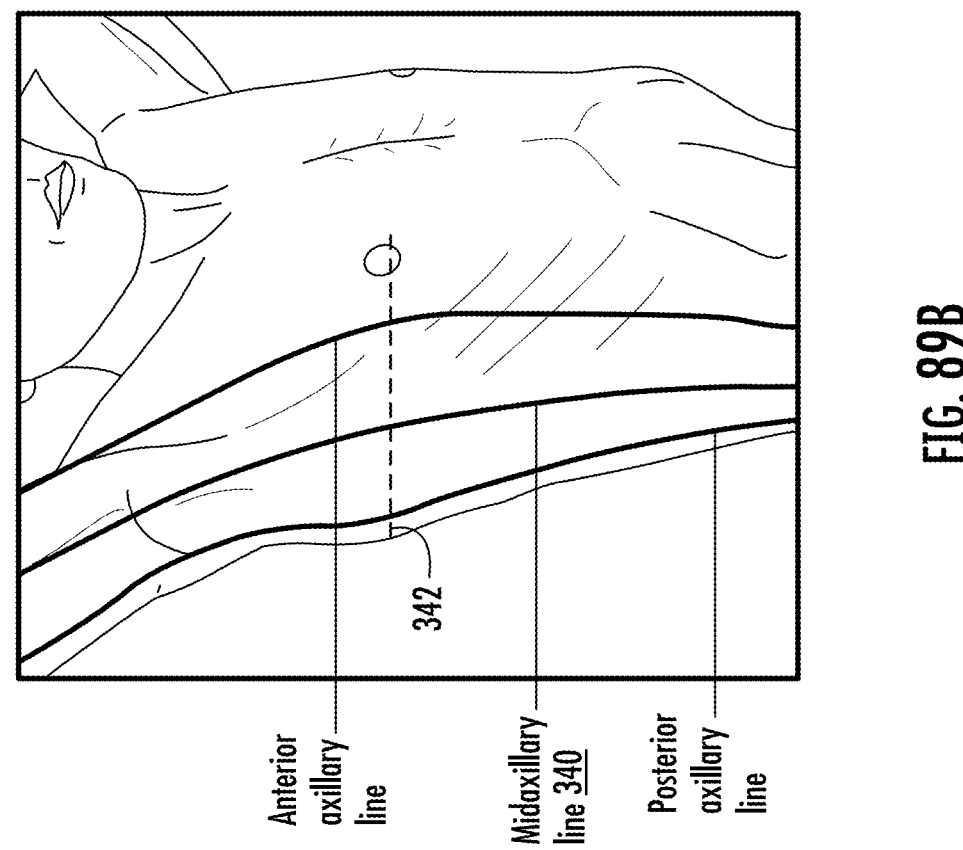
FIGS. 89A-89B illustrate a method of performing a needle thoracostomy with a needle thoracostomy device according to some embodiments.
Figure 89A:
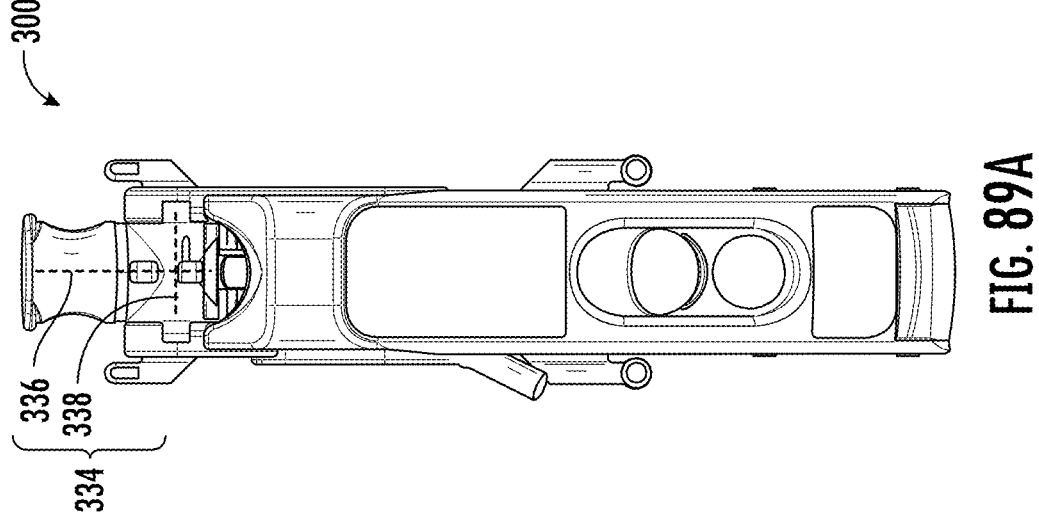
Figures 90A, 90B:
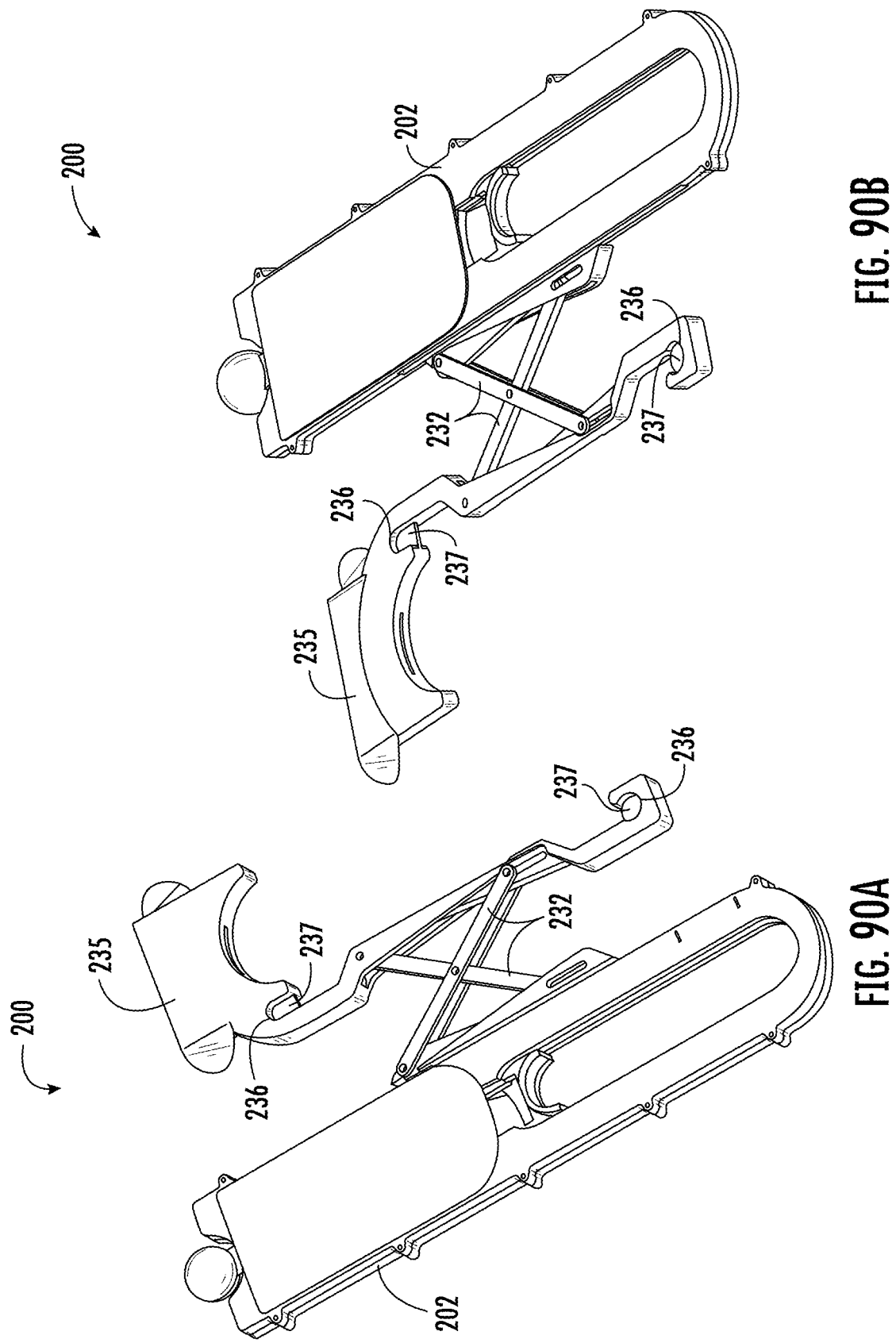
FIG. 90A-90D illustrate a needle thoracostomy device with a positioning device and a deployment device configured to couple to each other through magnets according to some embodiments.
Figure 90C:
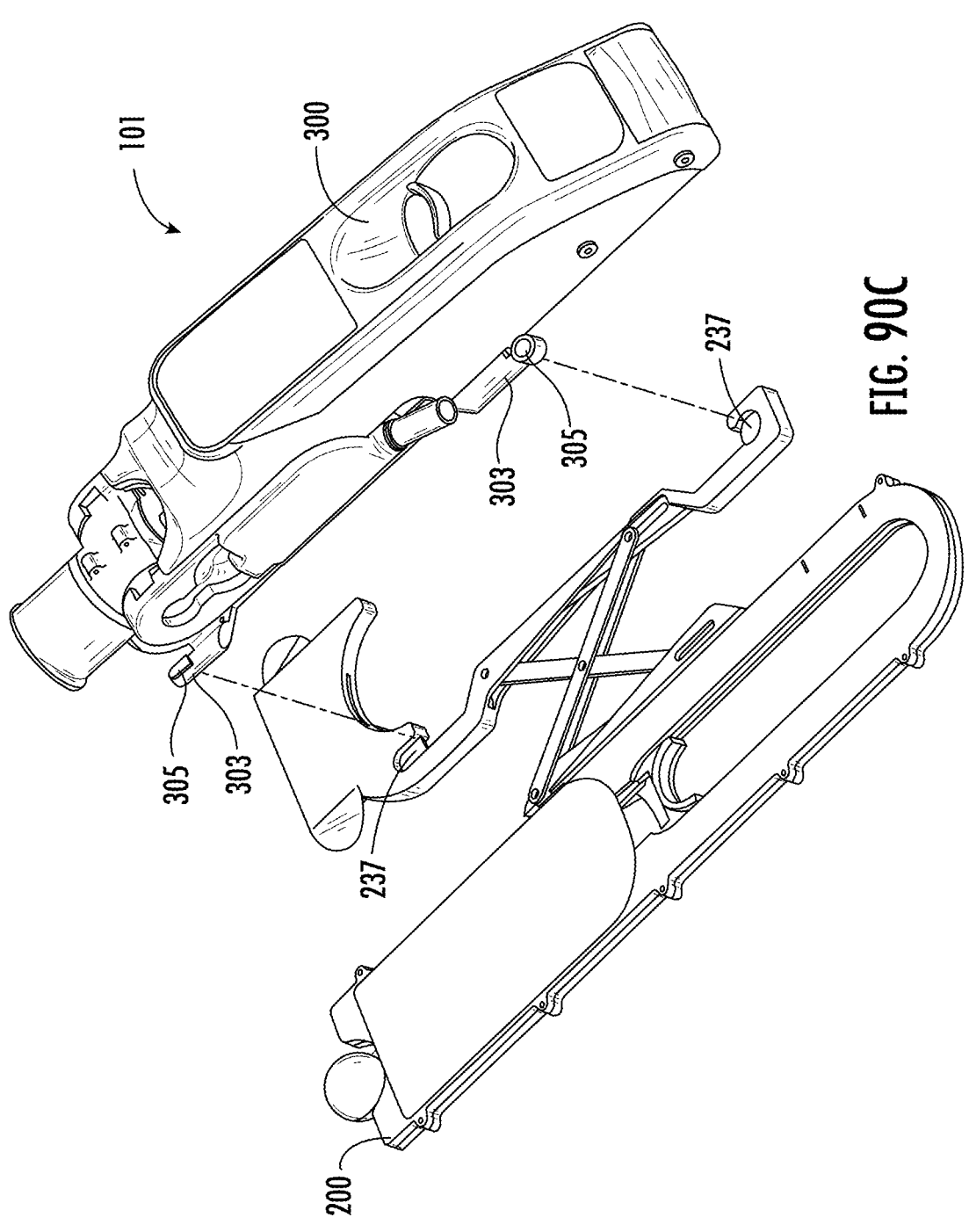
Figure 90D:
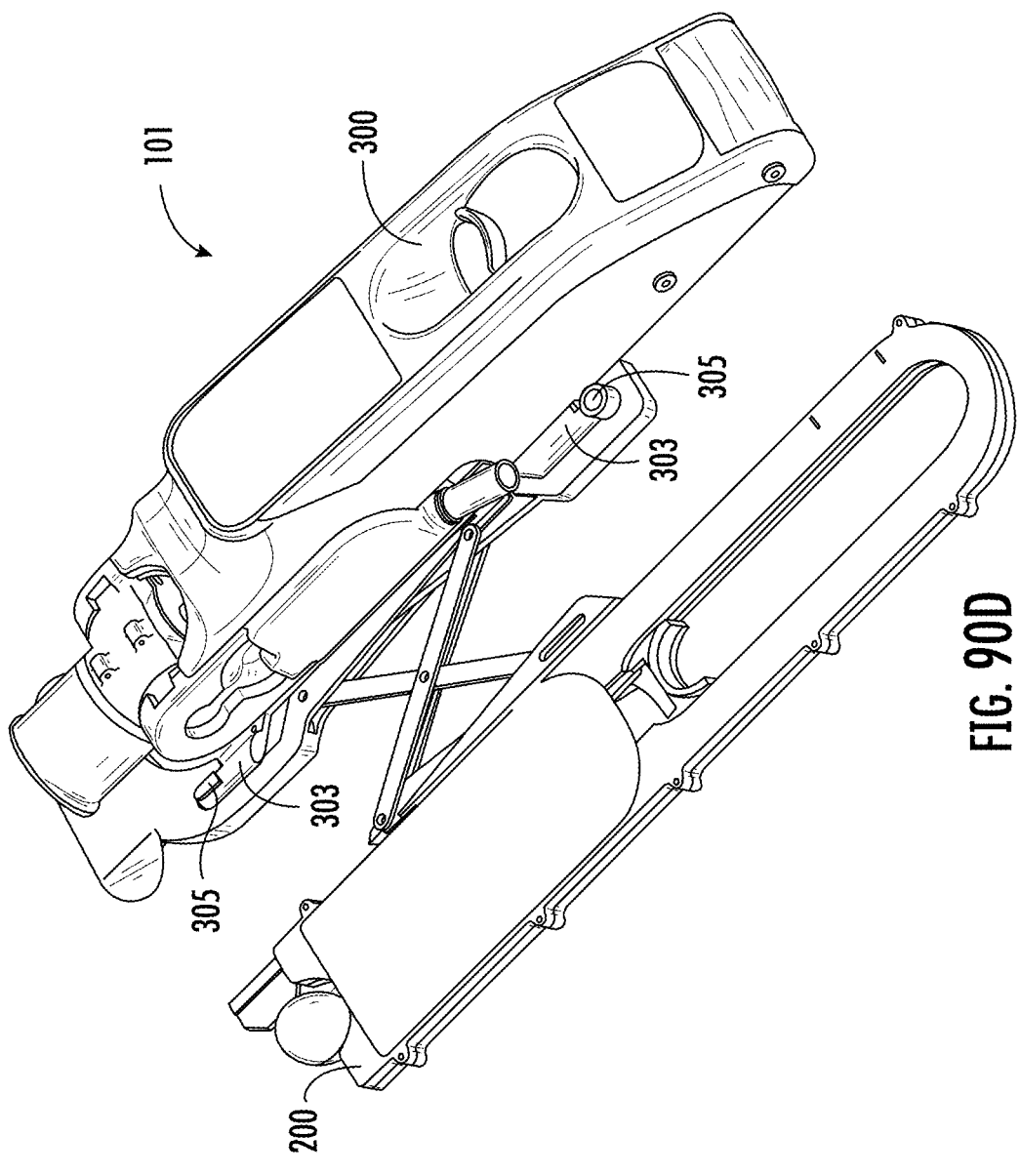

In some embodiments, the deployment device 300 may also be implemented in a needle thoracostomy procedure on the side of a patient, as shown in FIG. 89A-89B. This may be helpful in situations where the patient is on his or her side and cannot be moved. The deployment device 300 may have cross-hair marks 334 to aid in positioning the deployment device 300. The vertical cross-hair mark 336 may be aligned with the mid axillary line 340 of the patient, as shown, and the horizontal cross-hair mark 338 on the deployment device 300 may be aligned with the internipple line 342 of the patient. Once the deployment device 300 is positioned on the patient in this way, the deployment device 300 can be adhered to the patient and is ready to be used to perform the needle thoracostomy.

A method of performing a needle thoracostomy with the needle thoracostomy device 100 may therefore comprise aligning the vertical cross-hair mark 336 with the mid axillary line 340, aligning the horizontal cross-hair mark 338 with the internipple line 342, adhering the needle thoracostomy device 100 to the patient, and/or using the needle thoracostomy device 100 to perform a needle thoracostomy.

In yet another non-limiting embodiment, a method of performing a needle thoracostomy comprises: positioning a deployment device on a patient; actuating a lever to advance a needle assembly along a needle axis; detaching the needle upon entry into the pleural cavity of the patient; and venting fluid through a valve. In certain embodiments, positioning comprises aligning the deployment device. And optionally, method further comprises adhering the deployment device to the patient before deploying the device to perform the needle thoracostomy on the patient.

Turning now to details concerning the deployment device 300, certain embodiments of the deployment device 300 are illustrated in FIGS. 25-33. The deployment device 300 is configured to successfully perform the needle thoracostomy without requiring that the user have special training. Thus, each step of the needle thoracostomy can be completed by following simple instructions. This increases the success rate of needle thoracostomies performed with the deployment device 300.

A needle thoracostomy can be effectively carried out in various locations on a patient. Typically, a patient needs a needle thoracostomy because air has entered the patient's pleural cavity, the space between the lungs and the chest wall. Because air is typically lighter than other fluids within the pleural cavity, it is desirable to perform the needle thoracostomy high up on the patient's chest, as this is typically the highest point on the patient as they rest on their back. Therefore, as mentioned above, this disclosure primarily discusses performing the needle thoracostomy in this location, just above the third rib. However, it is to be understood that the deployment device 300 and methods of use disclosed herein can also be used in other locations on the body.

Figure 34:
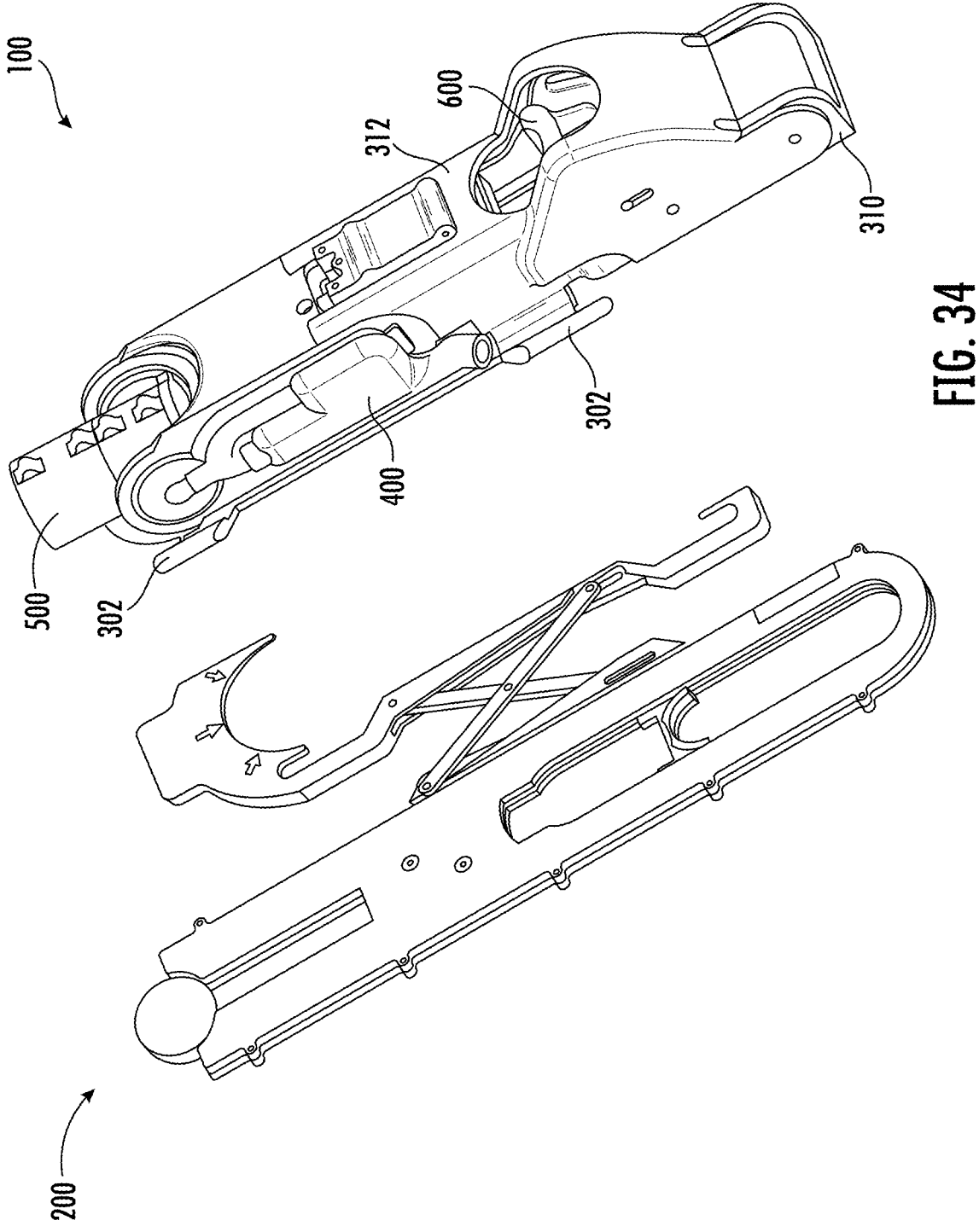
FIG. 34 is a perspective view of a needle thoracostomy device prior to placement with a positioning device according to some embodiments.
Figure 35:
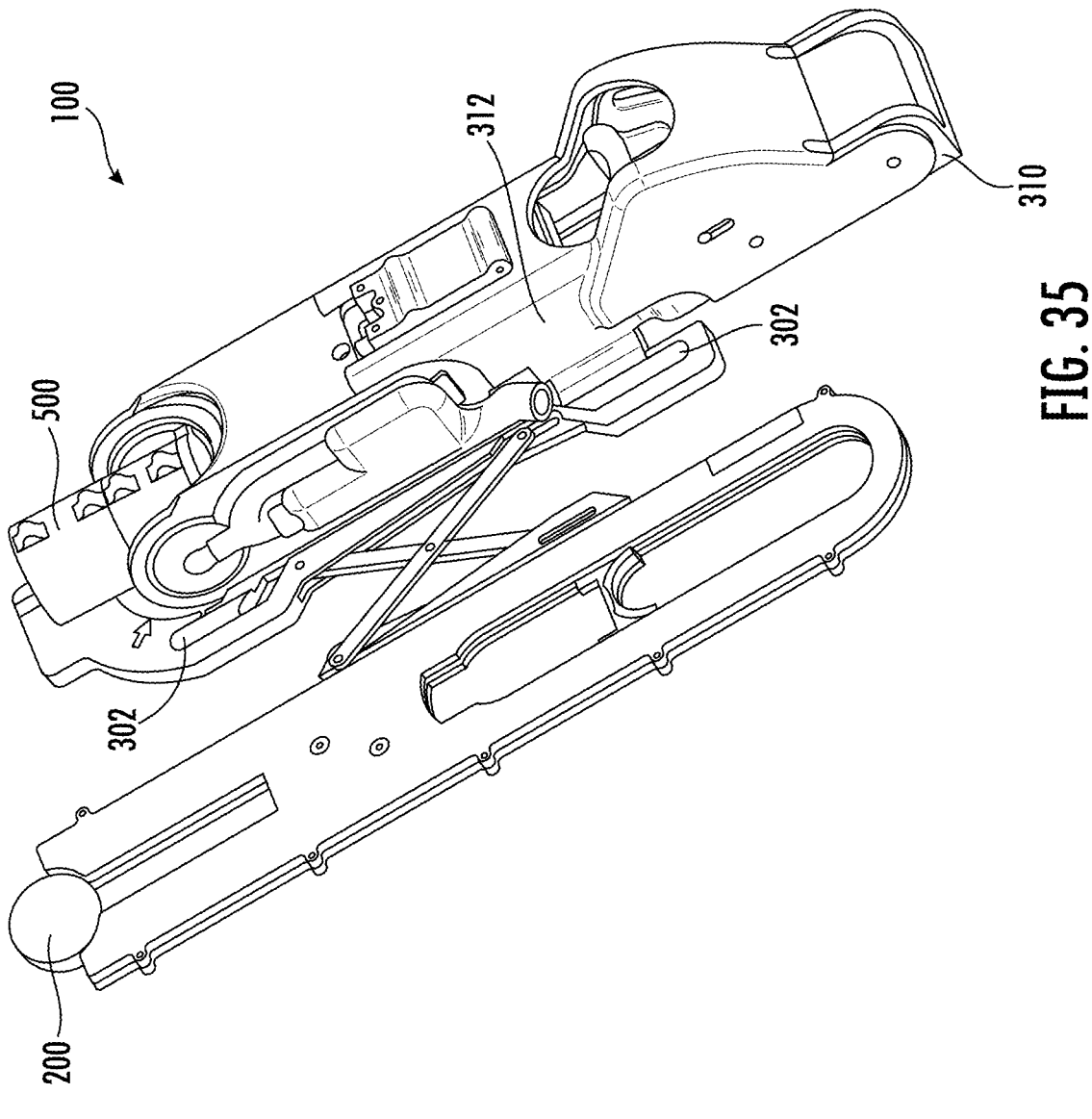
FIG. 35 is a perspective view of a needle thoracostomy device placed with a positioning device according to some embodiments.

As shown in FIGS. 34-35, the needle thoracostomy device 100 may be implemented with a positioning device 200, which is configured to help position the needle thoracostomy device 100 in a desirable location for the needle thoracostomy. The needle thoracostomy device 100 may engage with the positioning device 200 to correctly position the needle thoracostomy device 100. For example, the needle thoracostomy device 100 may comprise a docking prong 302 that is configured to position the needle thoracostomy device 100 on a patient with respect to the positioning device 200. The needle thoracostomy device 100 may have docking prongs 302 on both sides of the needle thoracostomy device 100 to allow the needle thoracostomy device 100 to be positioned on the left side or the right side of the patient according to what is needed. The needle thoracostomy device 100 may also be configured to attach to the patient. For example, the needle thoracostomy device 100 may have adhesive on the bottom surface 304 of the deployment device 300 to hold the needle thoracostomy device 100 in the desired location while the needle thoracostomy is performed. Similarly, the needle thoracostomy device 100 may comprise suture holes 306 that allow the user to suture the needle thoracostomy device 100 to the patient. In other words, the suture holes 306 are configured to enable attachment of the venting device 400 or other component of the needle thoracostomy device 100 to the patient with sutures. This may be especially useful in situations where the patient must be moved after the needle thoracostomy procedure when the needle thoracostomy device 100 is being used to vent the pleural cavity because the needle thoracostomy device 100 is more securely attached to the patient and is less easily dislodged or removed.

Figure 36:
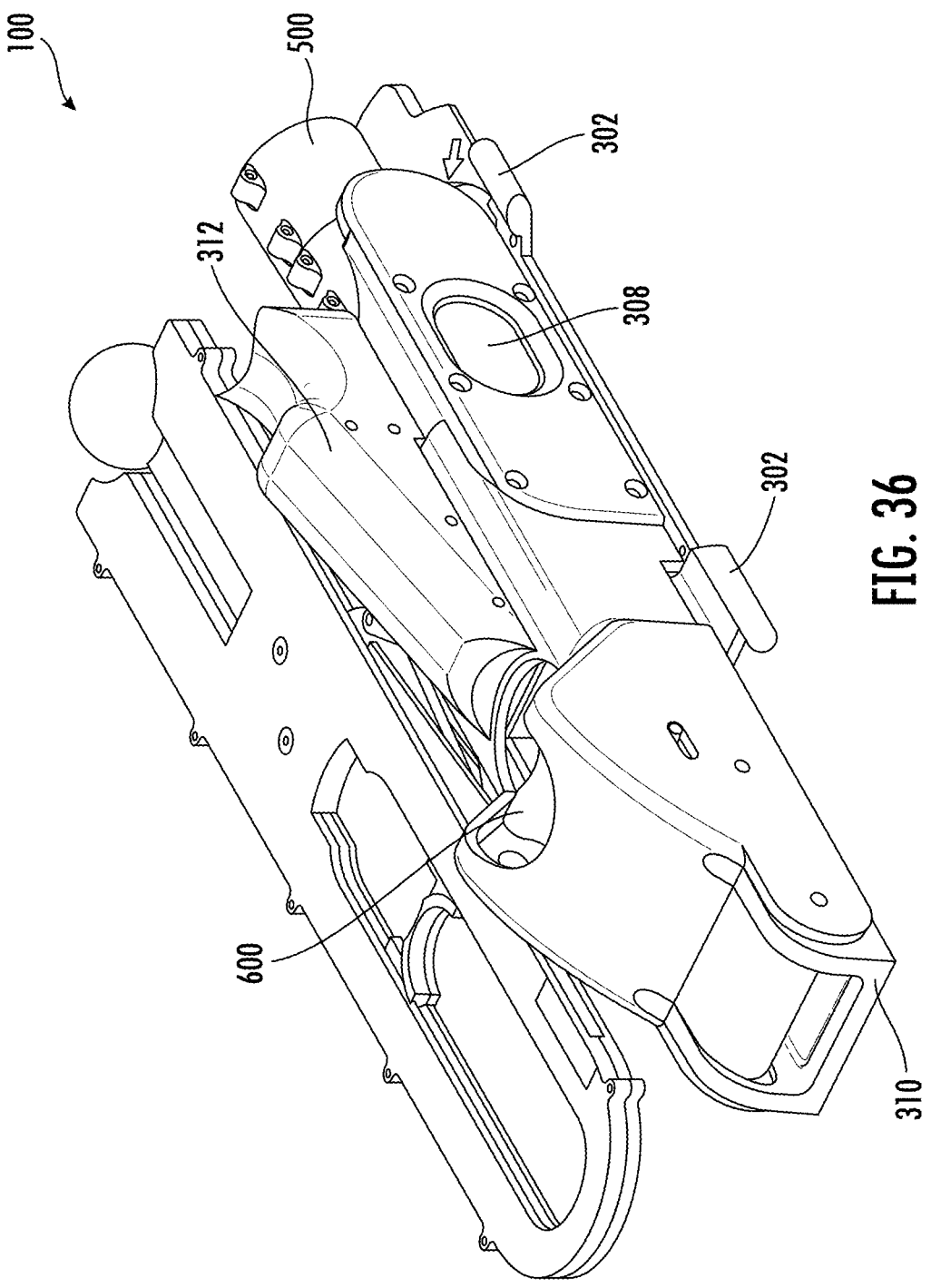
FIG. 36 is a perspective view of a needle thoracostomy device in the stored position according to some embodiments.

In some embodiments, the needle thoracostomy device 100 is configured to move between a stored position, a raised position, and a deployed position. As shown in FIG. 36, the deployment device 300 may comprise a release button 308 that is configured to unlock the needle thoracostomy device 100 from the stored position. Once the release button 308 has been pressed, the needle thoracostomy device 100 can begin to move up into the raised position, as discussed in more detail below. The needle thoracostomy device 100 may have one or more release buttons 308. In embodiments with two release buttons 308, the release buttons 308 may be positioned on opposite sides of the needle thoracostomy device 100 so that a pinching motion may be implemented by the user to press the release buttons 308 and unlock the needle thoracostomy device 100.

Figure 31:
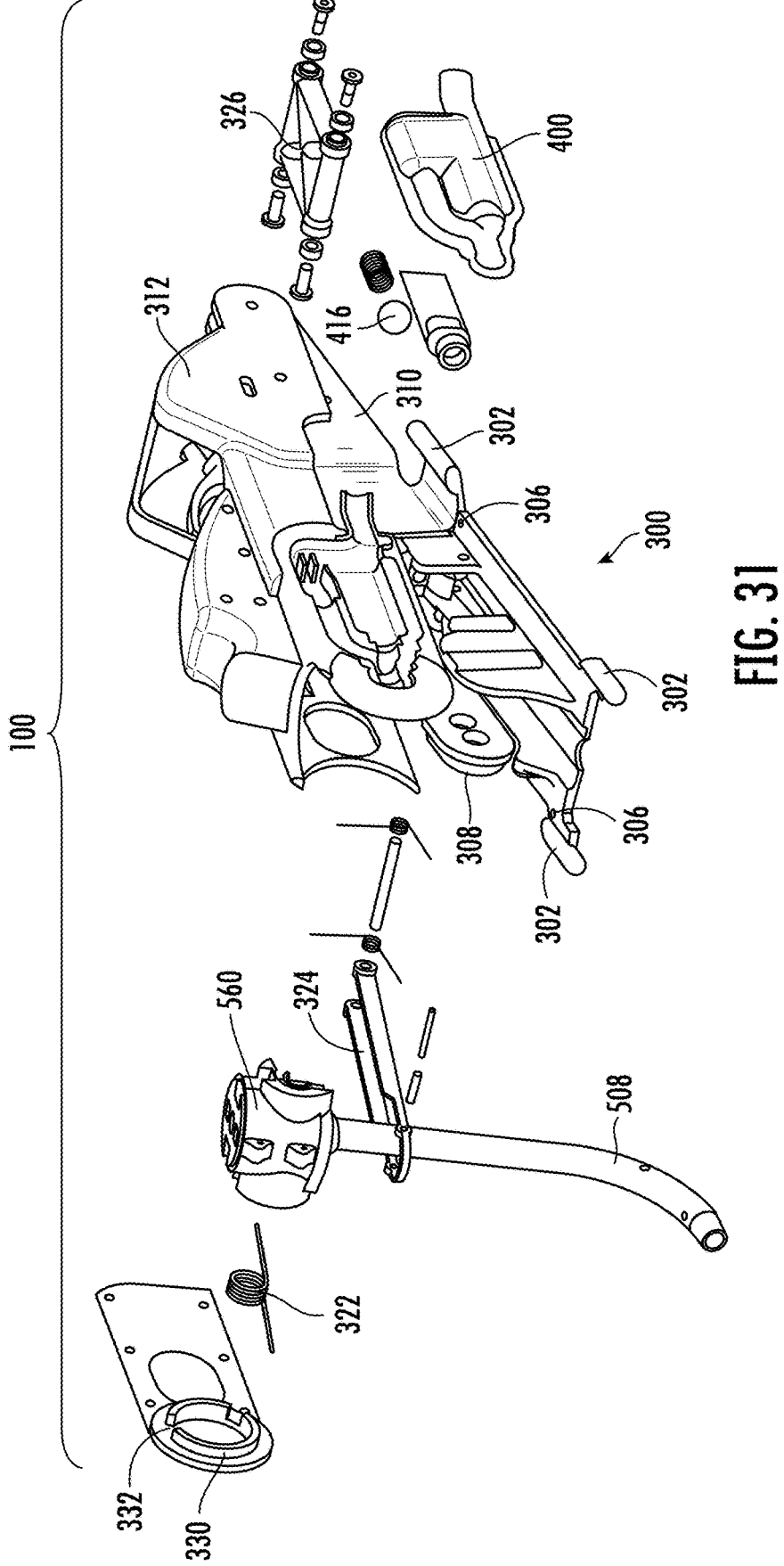
FIG. 31 is an exploded view of a needle thoracostomy device according to some embodiments.
Figure 37:
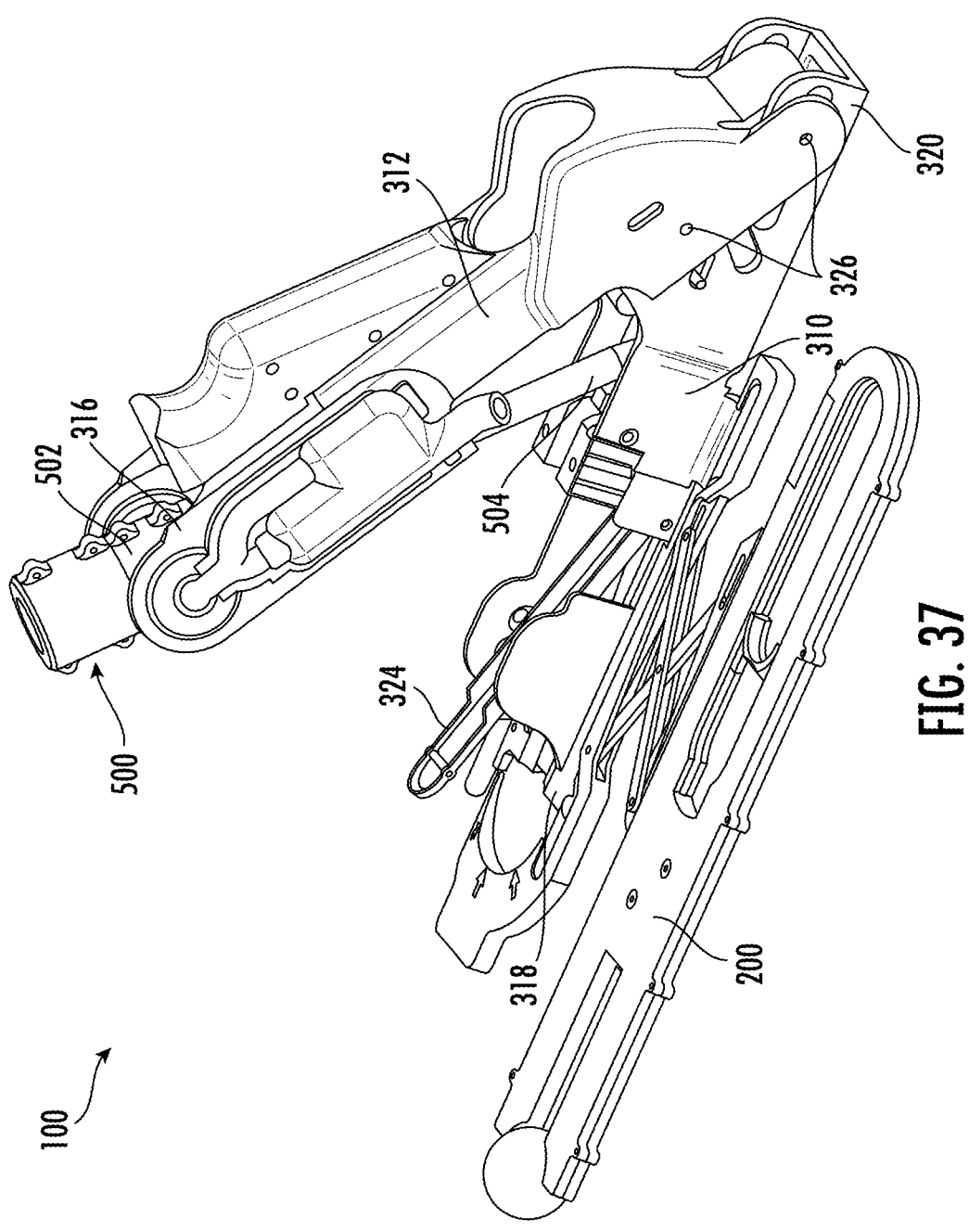
FIG. 37 is a perspective view of a needle thoracostomy device in between the stored position and the raised position according to some embodiments.
Figure 38:
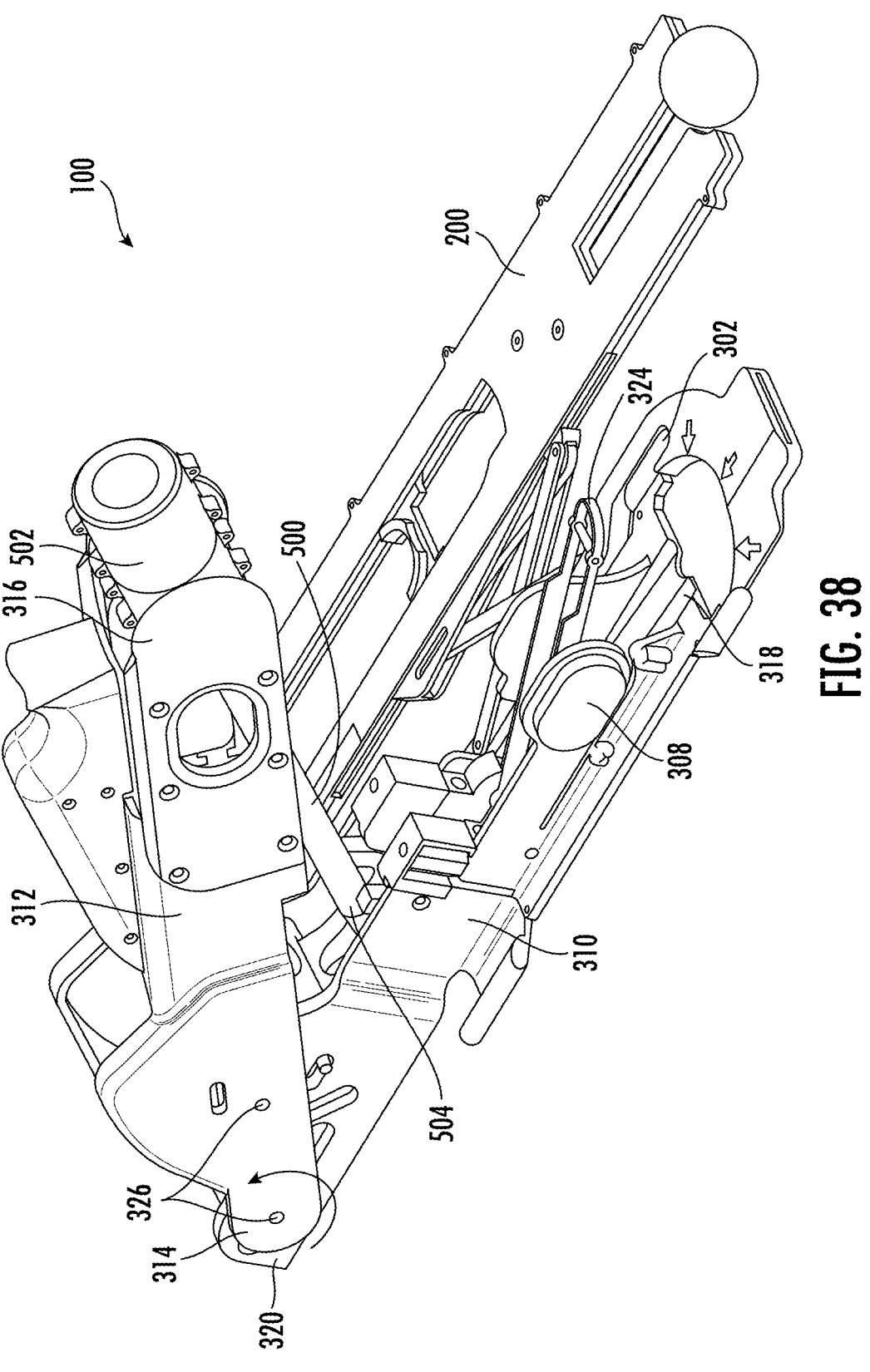
FIG. 38 is a perspective view of a needle thoracostomy device in between the stored position and the raised position according to some embodiments.
Figure 39:
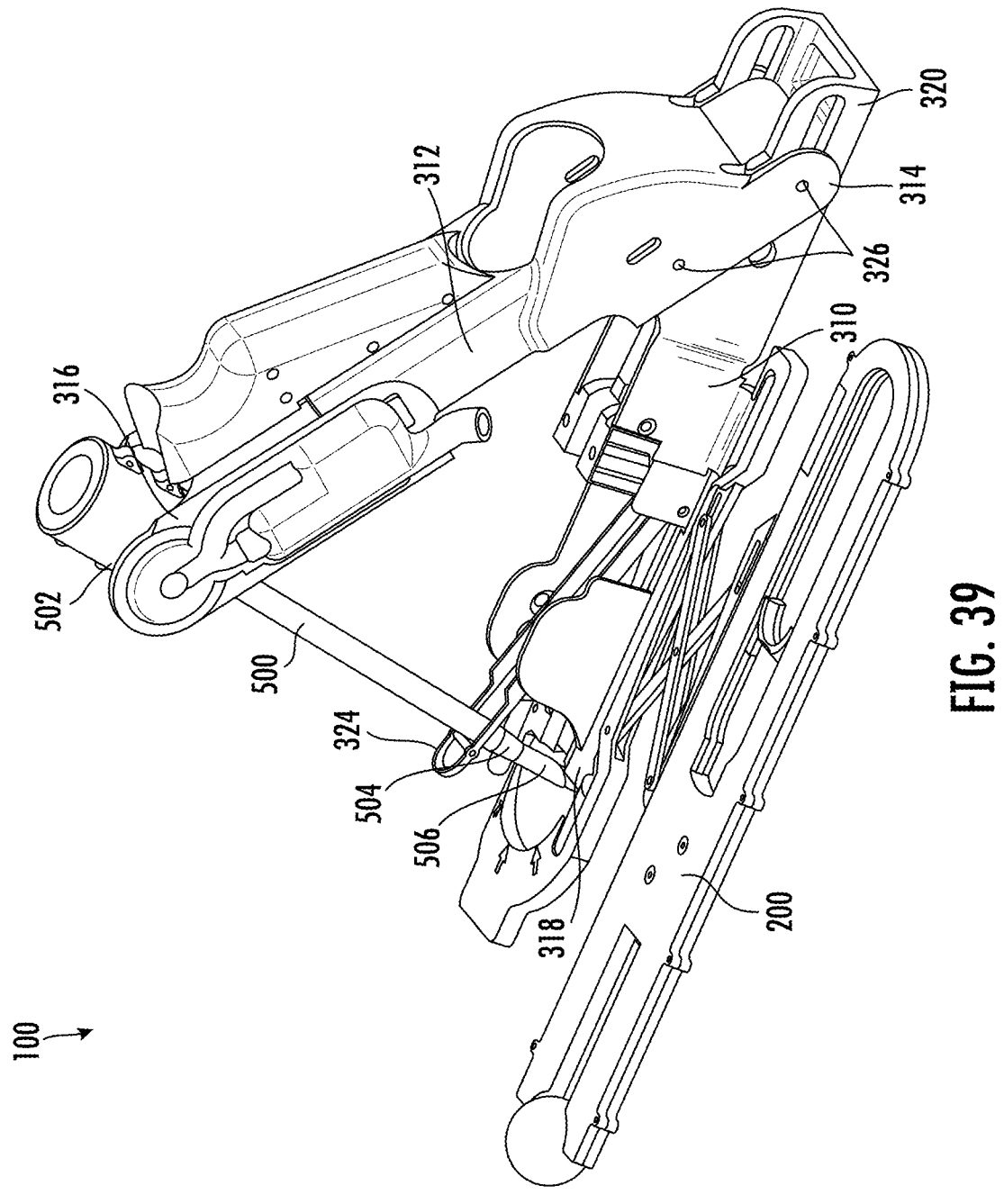
FIG. 39 is a perspective view of a needle thoracostomy device in the raised position according to some embodiments.

The deployment device 300 may have a base 310, a lever 312, and/or a needle assembly 500. The lever 312 of the deployment device 300 may have a first end 314 and a second end 316. The base 310 may also have a first end 318 and a second end 320. The first end 314 of the lever 312 may be hingedly coupled to the second end 320 of the base 310. This allows the lever 312 of the deployment device 300 to move between the stored position and the raised position, as illustrated in FIGS. 37-39. The second end 316 of the lever 312 of the deployment device 300 may be hingedly coupled to the needle assembly 500. When the needle thoracostomy device 100 is in the stored position (FIG. 36), the lever 312 and the needle assembly 500 are adjacent to the base 310 and may extend parallel or substantially parallel with the base 310. When the needle thoracostomy device 100 is in the raised position (FIGS. 39-40), the lever 312 is positioned at an oblique angle with respect to the base 310 and the needle assembly 500 extends between the lever 312 and the base 310. In some embodiments, as the needle thoracostomy device 100 moves from the stored position to the raised position, the needle assembly 500 is configured to maintain contact with the base 310. Because the needle assembly 500 is hingedly coupled to the second end 316 of the lever 312, as the lever 312 moves to the raised position, this raises a hinged end 502 of the needle assembly 500. The needle assembly 500 may be biased to rotate with respect to the lever 312 such that a free end 504 of the needle assembly 500 slides forward toward the first end 318 of the base 310. To assist deployment of the needle assembly 500, a spring assist 322, which may be a torsion spring as shown in FIG. 31, may be positioned at the second end 316 of the lever 312 to bias the needle assembly 500 toward an unfolded position. In some embodiments, the lever 312 may be lifted from the base 310 and the needle assembly 500 may be unfolded from the lever 312 and then placed in contact with the first end 318 of the base 310. When the needle thoracostomy device 100 is in the deployed position (FIGS. 64-65), the lever 312 is again adjacent to the base 310 and may be parallel with or substantially parallel with the base 310, and the needle assembly 500 extends below the base 310. Thus, in use, once the needle thoracostomy device 100 is in the deployed position, the needle assembly 500 extends into the patient.

Figure 40:
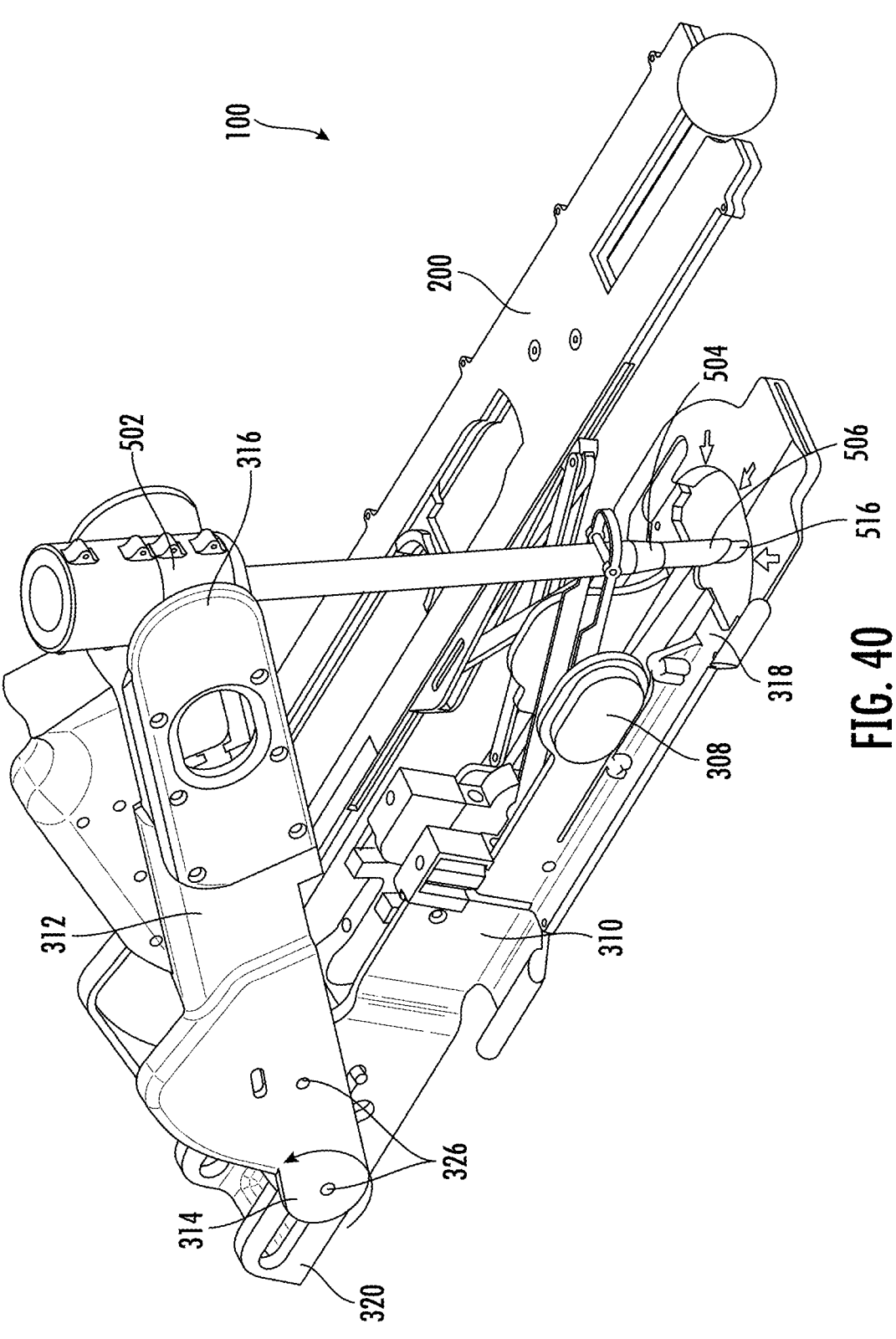
FIG. 40 is a perspective view of a needle thoracostomy device in the raised position according to some embodiments.
Figure 42:
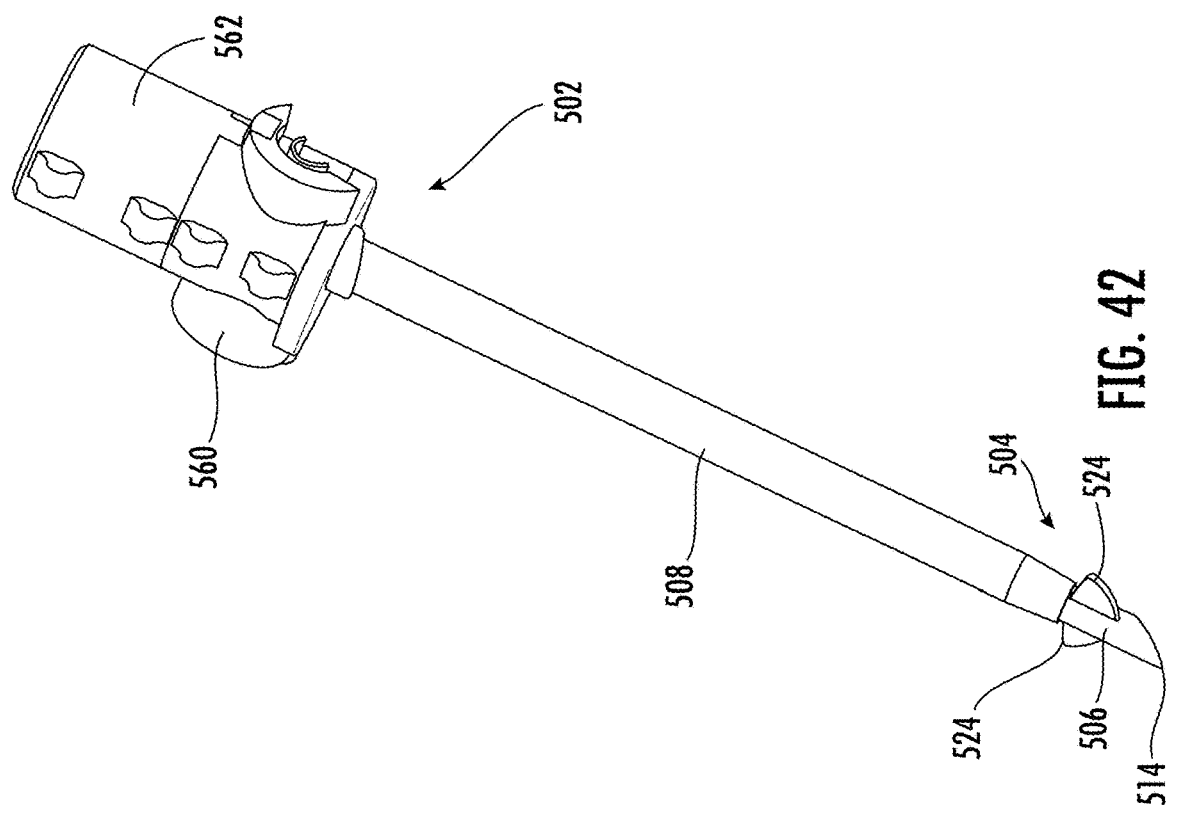
FIG. 42 is a perspective view of a needle assembly with the plunger in the retracted position according to some embodiments.
Figure 41:
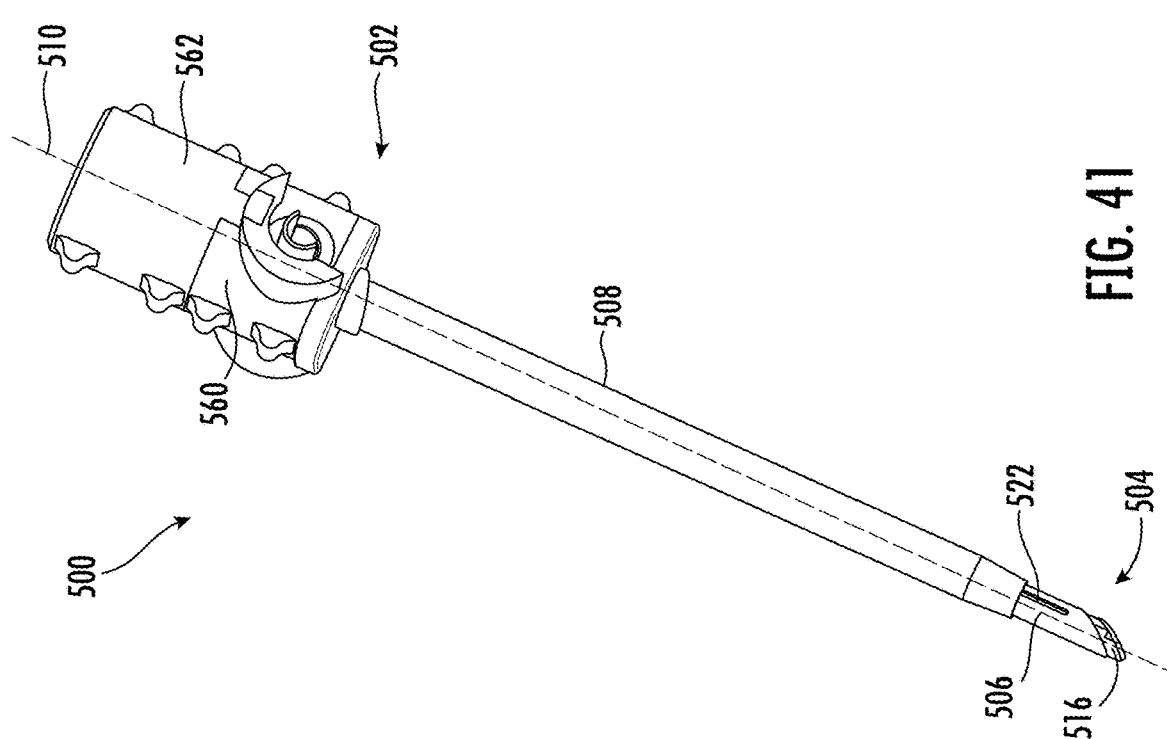
FIG. 41 is a perspective view of a needle assembly with the plunger in the extended position according to some embodiments.
Figure 43A:
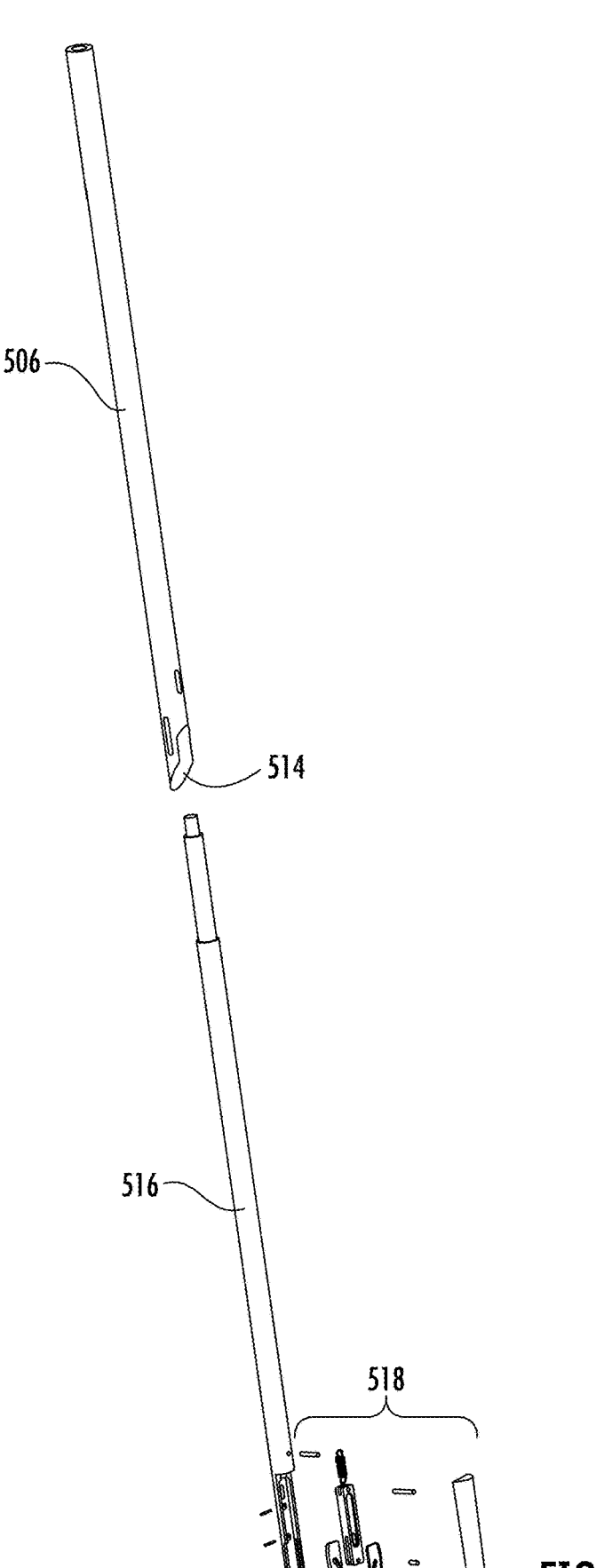
FIG. 43A is an exploded view of a needle assembly according to some embodiments.
Figure 43B:
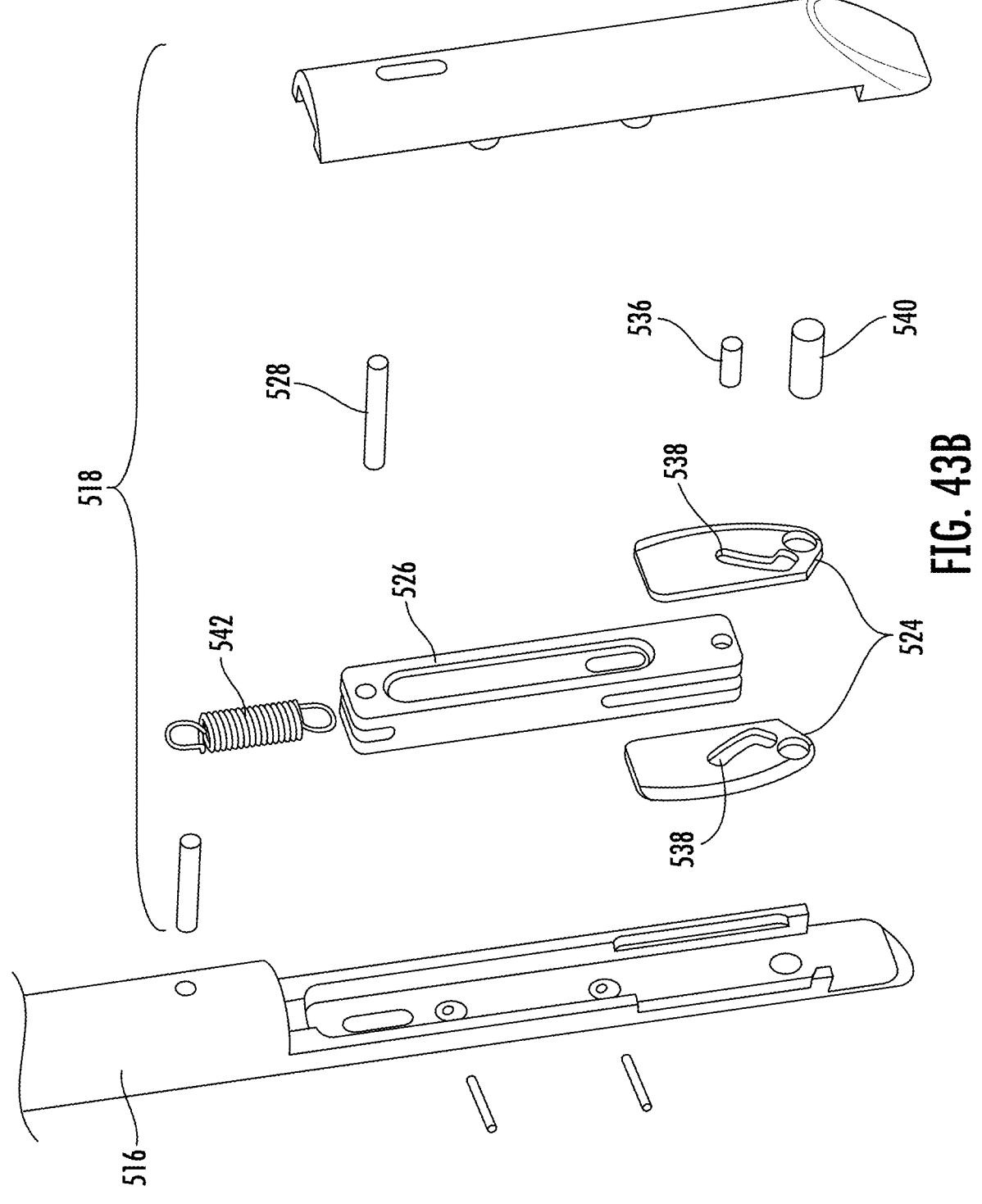
FIG. 43B is an exploded view of a blade assembly according to some embodiments.

The needle assembly 500 may comprise a needle 506 and a catheter 508 (see FIG. 40). The needle assembly 500 may be useful in more situations than just for use in a deployment device 300 for a needle thoracostomy. For example, a catheter may need to be placed in situations where medication, hydration, nutrition, or some other fluid needs to be injected into the patient's bloodstream. A catheter is also useful in situations where fluid buildup, including air, needs to be removed. The presently disclosed needle assembly 500 is configured to allow the catheter 508 to be successfully placed by creating an incision that is correctly sized for the catheter 508. This helps to avoid leaks around the catheter 508 when the incision is too large. This also helps to prevent buckling of the catheter 508 upon insertion when the incision is too small. By automatically creating the correct size of incision, successful insertion of the catheter 508 is facilitated, leading to more efficient and rapid medical intervention. This helps to save lives in emergency situations where immediate intervention is required, such as in pre-hospital care, combat medicine, and emergency departments.

The needle 506 may be positioned inside of the catheter 508. This allows the needle 506 to make the initial incision before introducing the catheter 508 to the incision. In addition, as the needle assembly 500 is inserted into the incision, the catheter 508 is automatically introduced into the incision and is structurally supported by the needle 506 while doing so. This helps to guide the catheter 508 into the incision and helps prevent buckling of the catheter 508.

Figure 57:
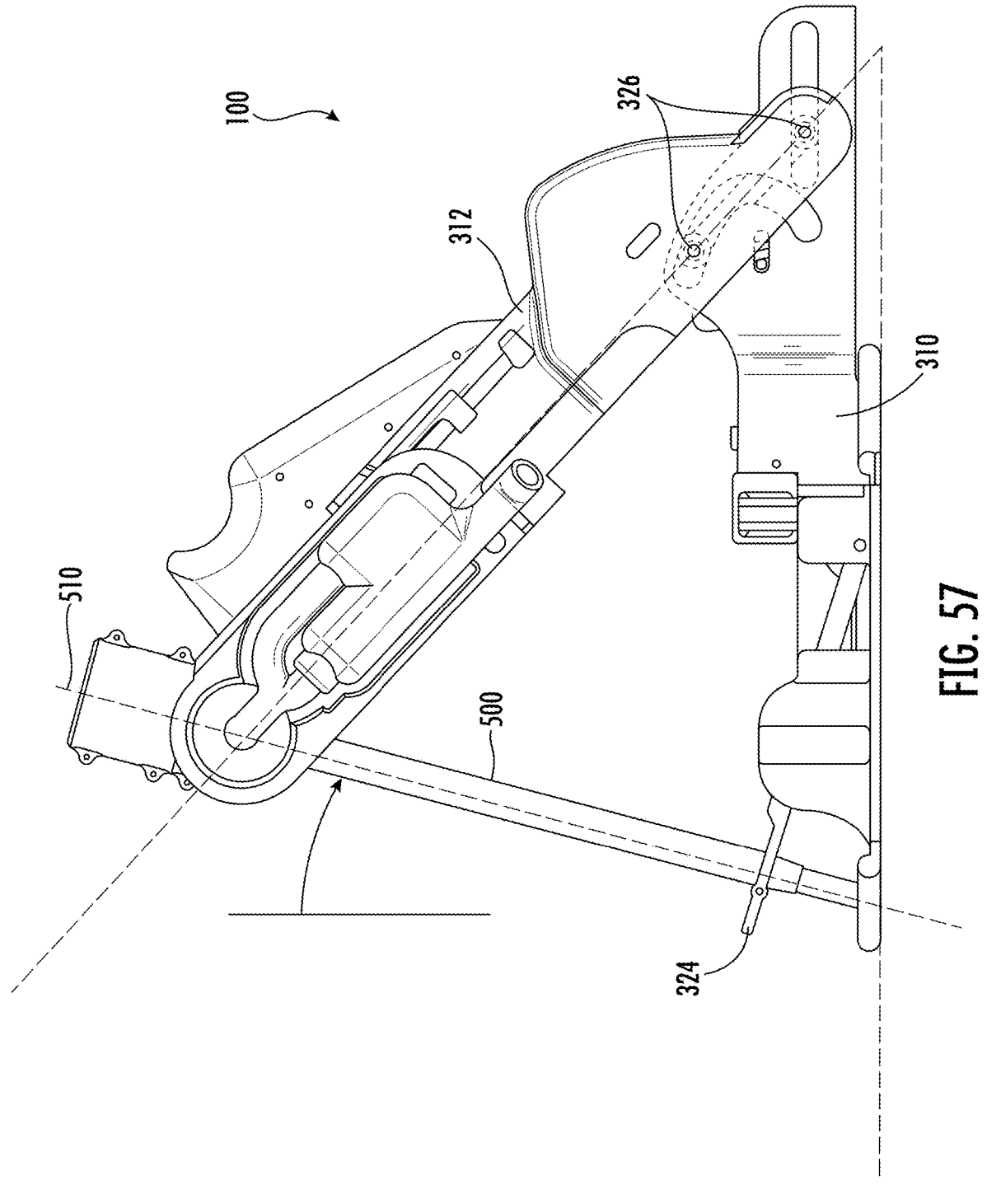
FIG. 57 is a side view of a needle thoracostomy device in the raised position according to some embodiments.
Figure 58:
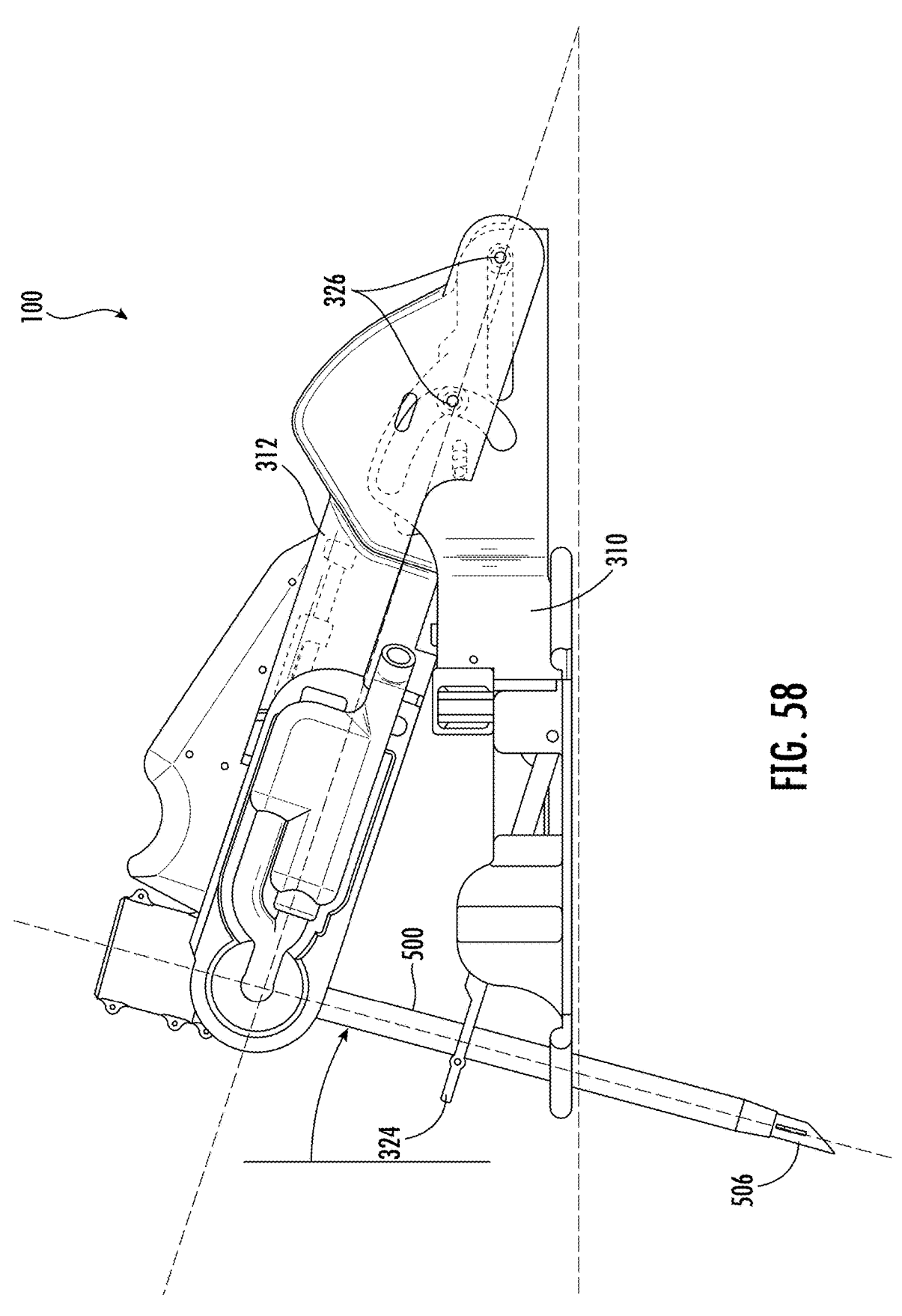
FIG. 58 is a side view of a needle thoracostomy device in between the raised position and the deployed position according to some embodiments.

The length of the lever 312, the base 310, and the needle assembly 500 and the locations of the couplings between these components may be selected so that, when the lever 312 is in the raised position, the needle assembly 500 is positioned at a proper angle for insertion into the patient (see FIGS. 57-58). The needle assembly 500 may be close to perpendicular to the base 310 but may be slightly oblique to encourage the needle 506 of the needle assembly 500 to move over the top of the 3rd rib during insertion. In different embodiments, the angle of the needle assembly 500 with respect to the line perpendicular to the base 310 may be less than or equal to 20 degrees, between 0 degrees and 15 degrees, between 10 degrees and 20 degrees, between 10 degrees and 15 degrees, and/or equal 15 degrees.

The deployment device 300 may include a needle guide loop 324 as part of the base 310 (FIGS. 37-40). The needle guide loop 324 is configured to provide additional support to the needle assembly 500 both in positioning the needle 506 prior to deployment and in inserting the needle 506 into the patient. The needle guide loop 324 may be U-shaped and may be hingedly coupled to the base 310. When the needle 506 is placed in the proper position for insertion into the patient, the needle 506 may be positioned in the hook of the needle guide loop 324. In some embodiments, the needle guide loop 324 is spring-loaded such that, when the lever 312 is raised up towards the raised position, the needle guide loop 324 automatically lifts up off of the base 310. The needle guide loop 324 may be biased toward a position where the needle guide loop 324 creates an angle of between 10 and 45 degrees with the base 310. This allows the needle guide loop 324 to provide better support for the needle assembly 500 and helps to prevent the needle assembly 500 from over-extending and/or moving into an undesired angle as the needle assembly 500 is inserted into the patient. Additionally, as the needle assembly 500 is inserted into the patient, the needle guide loop 324 may lower down against the base 310 to continue to provide support and guide the path of the needle assembly 500 into the patient. In such embodiments, the needle guide loop 324 and the base 310 are together configured to limit movement of the needle assembly 500 besides along the axis 510 of the needle 506 and thus help the needle assembly 500 to be inserted straight into the incision site.

Figure 45:
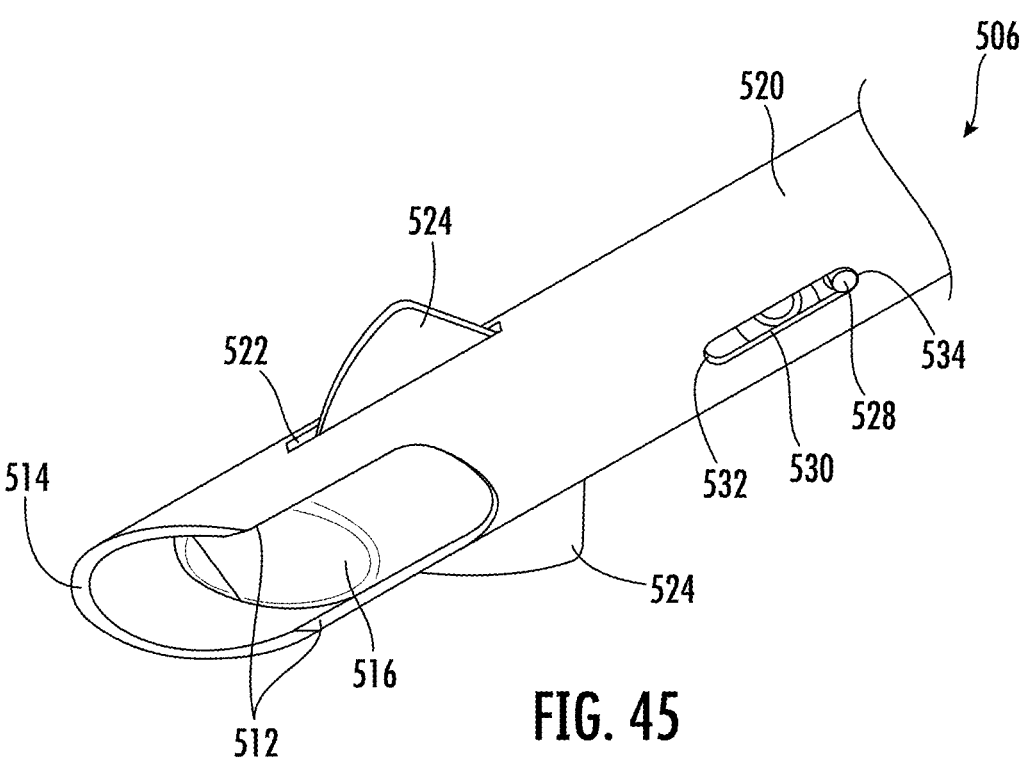
FIG. 45 is a close-up view of an end of a needle assembly with the plunger in the retracted position according to some embodiments.
Figures 86A, 86B:
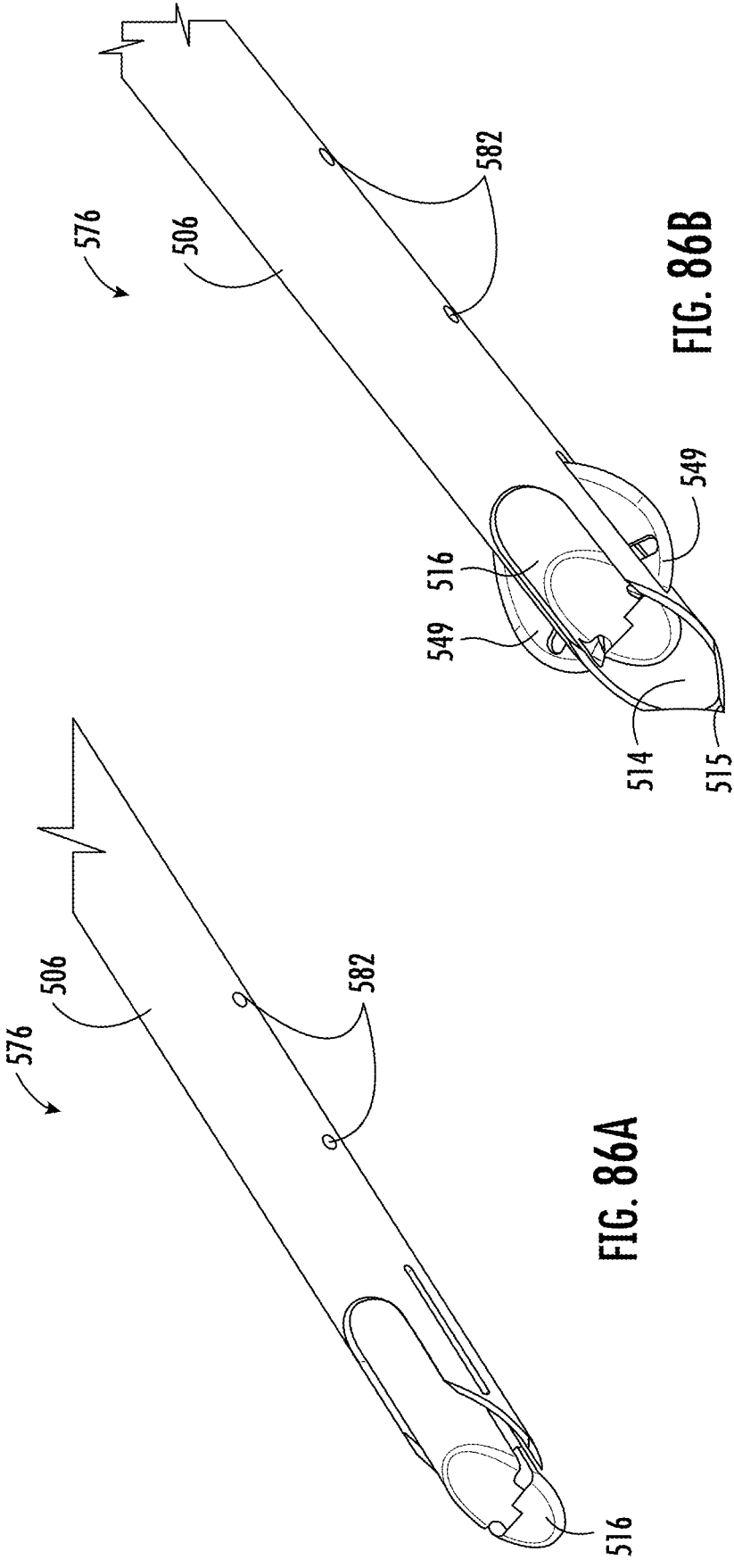
FIGS. 86A-86B show a sharpened needle point of a needle assembly according to some embodiments.

A needle end 514 of the needle 506 adjacent to the free end 504 of the needle assembly 500 may be sharpened, may be angled, and may have rails 512 that create a C-shape incision, as shown in FIG. 45. This allows additional room in the incision for the catheter 508 that follows the needle 506, thus further helping to avoid buckling of the catheter 508 and allowing for larger catheter diameters. In some embodiments, the needle end 514 of the needle 506 comprises a sharpened end with a pointed, piercing tip 515 that is configured to reduce a force required to puncture skin of a patient, as shown in FIGS. 86A-86B.

Some embodiments of the needle assembly 500 comprise a needle 506, a catheter 508, a plunger 516, and a blade assembly 518, as shown in FIGS. 41-48. The needle 506 may be positioned within the catheter 508 and the plunger 516 may be positioned within the needle 506. The needle 506 has a hollow body 520 and a needle end 514. In some embodiments, the needle end 514 of the hollow body 520 is C-shaped, as mentioned above, and is sharpened. This shape provides a benefit in creating an incision that is better able to receive and seal around the catheter 508. Other shapes for the needle end 514 may also be implemented. In some embodiments, the needle 506 also has at least one slot 522 extending through the wall of the hollow body 520. This slot 522 is configured to allow the blade assembly 518 to extend therethrough, as explained in more detail below. In some embodiments, the slot 522 is replaced with a notch. In some embodiments, the slot 522 is not included and the blade assembly 518 is configured to deploy in another manner that does not implement a slot.

The plunger 516 may be positioned within the needle 506 and is slidably coupled with the needle 506. This allows the plunger 516 to move between an extended, inactive position shown in FIGS. 44 and 47 and a retracted, active position shown in FIGS. 45 and 48. When in the inactive position, the plunger 516 extends past the needle end 514 of the needle 506. This helps to avoid unintentional injury when the needle 506 is not in use, due to the needle end 514 coming in contact with a person. When in the active position, the needle end 514 of the needle 506 extends past the plunger 516 to allow the needle 506 to be used to create an incision.

The plunger 516 can be moved from the inactive position to the active position by simply pressing the needle assembly 500 against an incision site. This pressure moves the plunger 516 further into the needle 506 to allow the needle end 514 of the needle 506 to create the incision. During a needle thoracostomy, the incision only needs to penetrate to the pleural cavity. Once the pleural cavity of the patient is reached, there is a risk of injury to the patient if the needle 506 continues cutting deeper. The plunger 516 helps to mitigate this risk because, once the pleural cavity is reached, pressure on the plunger 516 is relieved, allowing the plunger 516 to move back to the inactive position. This helps to protect internal organs such as the lungs from unintentional damage by the needle end 514 of the needle 506. In some embodiments, the plunger 516 is biased toward the extended, inactive position.

Figure 44:
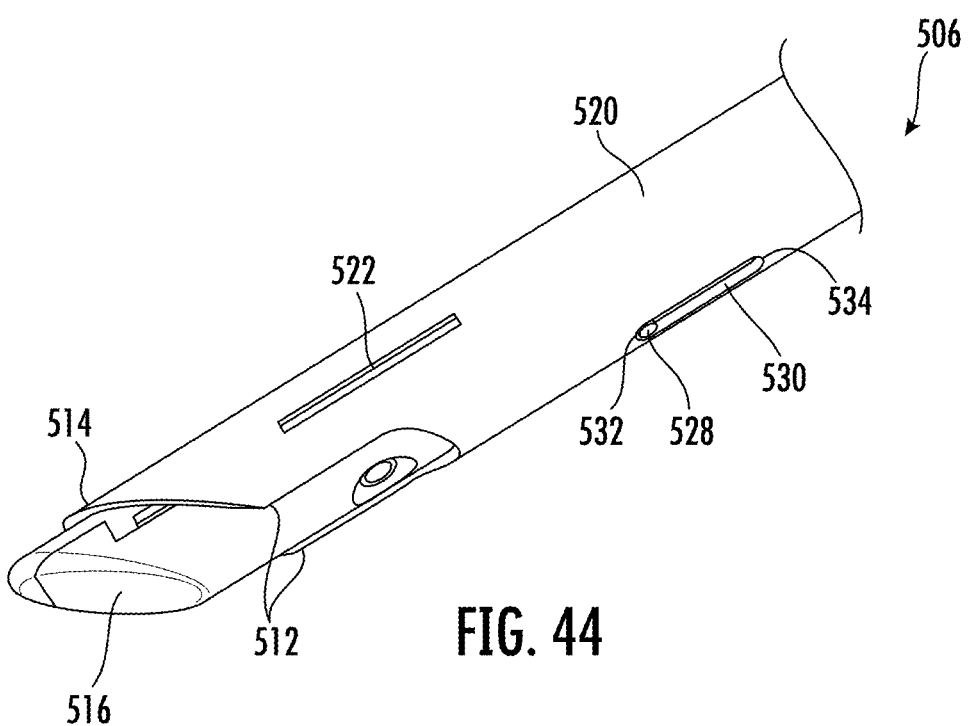
FIG. 44 is a close-up view of an end of a needle assembly with the plunger in the extended position according to some embodiments.

The blade assembly 518 is positioned within the needle 506 and is affixed to the plunger 516 and is therefore configured to generally move with the plunger 516. However, additional components allow the blade assembly 518 to also pivot and/or slide with respect to the plunger 516. In some embodiments, the blade assembly 518 is configured to automatically deploy at least one blade 524 through the at least one slot 522 of the needle 506 when the plunger 516 moves to the retracted, active position, as shown in FIG. 45. In some embodiments, the blade assembly 518 is configured to automatically retract the at least one blade 524 when the plunger 516 moves to the extended, inactive position (FIG. 44). Implementing a blade 524 in this way allows the blade 524 to widen the cut created by the needle 506. This can be done through the entire depth of the cut because, as long as the needle 506 is cutting through tissue, the plunger 516 remains depressed, and the blade 524 remains deployed. Thus, the risk of making a cut that is not deep enough is greatly reduced. This improves the ability of the catheter 508 to be inserted into the incision without damage to the catheter 508 and facilitates the process by making the widened incision at the same time that the needle 506 is inserted. Thus, in some embodiments of the present disclosure, the blades 524 are deployed automatically whenever the needle 506 is being used to make an incision and are retracted automatically when the needle 506 is not in use. The blade assembly 518 is therefore both safe and effective.

Figure 46:
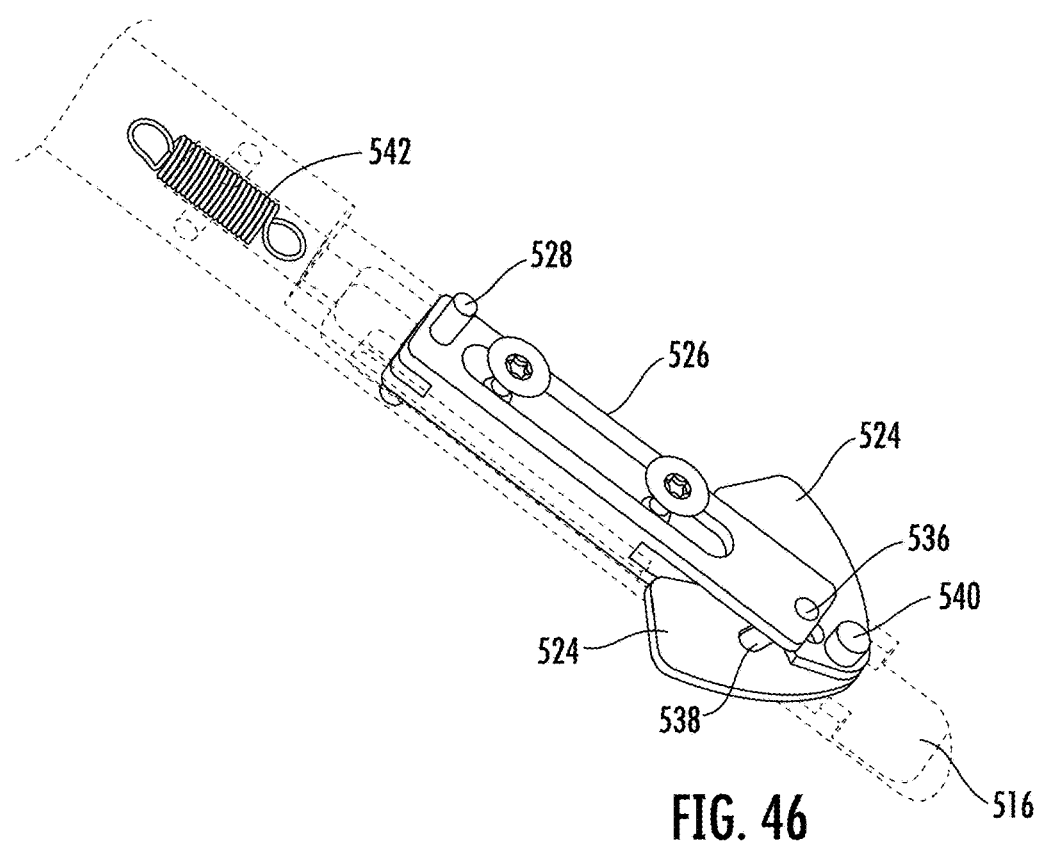
FIG. 46 is a close-up view of the interior components of a needle assembly according to some embodiments.

In some embodiments, the blade assembly 518 comprises a slider 526 and at least one blade 524, as shown in FIG. 46. In some embodiments, the slider 526 has a knob 528 that is configured to slidably couple with a needle channel 530 in the needle 506. The needle channel 530 has a first end 532 and a second end 534 opposite the first end 532. In some embodiments, the slider 526 also has a pin 536 that is configured to slidably engage with a blade channel 538 in the at least one blade 524 and the at least one blade 524 has a pivot point 540 about which the blade 524 is pivotably coupled with the plunger 516, as shown in FIG. 46. Thus, the pin 536 may be coupled to the needle 506 through the slider 526, with the pin 536 affixed to the slider 526 and the knob 528 slidably coupled with the needle channel 530. In some embodiments, the blade channel 538 is curved. The blade(s) 524 are sized to create a full-depth incision that is the proper size for the catheter 508 such that the risk of leaks around the outside of the catheter 508 is greatly reduced.

Figure 47:
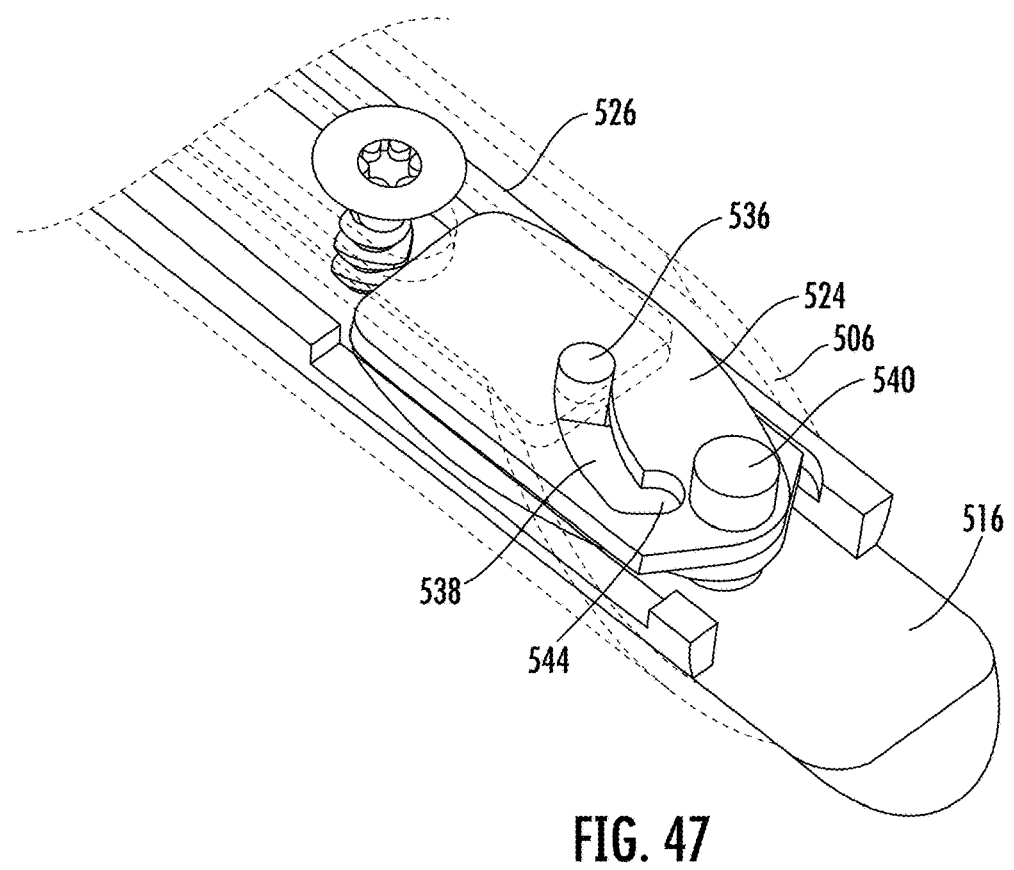
FIG. 47 is a close-up view of the blades of a needle assembly in the retracted position according to some embodiments.
Figure 48:
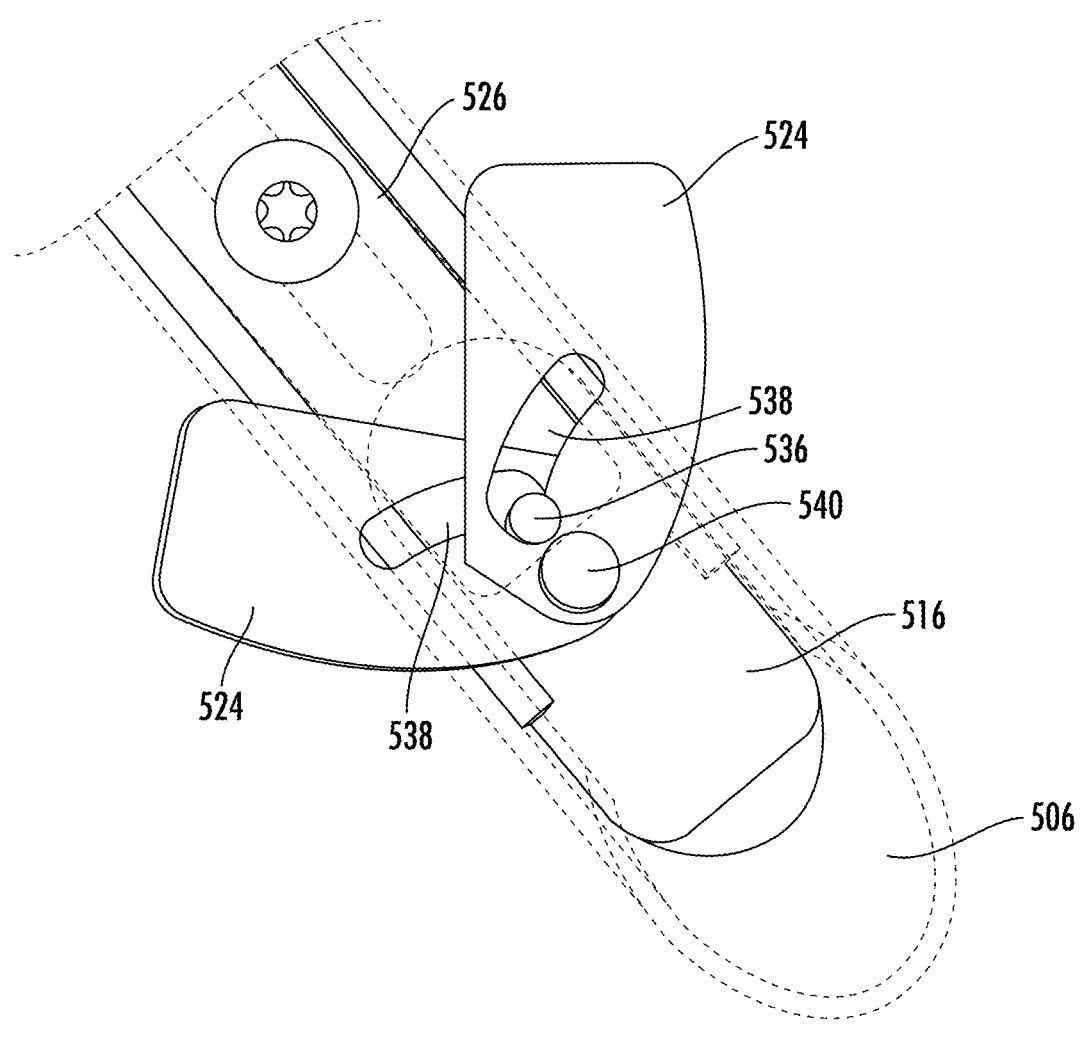
FIG. 48 is a close-up view of the blades of a needles system in the deployed position according to some embodiments.

When the plunger 516 is in the extended position, the knob 528 is adjacent to the first end 532 nearest the needle end 514 of the needle 506. When the plunger 516 moves from the extended, inactive position to the retracted, active position, the slider 526 moves with the plunger 516 until the knob 528 reaches the second end 534 of the needle channel 530. Thus, once the knob 528 reaches the second end 534 of the needle channel 530, the slider 526 is unable to slide farther with respect to the needle 506, but the plunger 516 continues due to the pressure on the plunger 516. This movement between the slider 526 and the plunger 516 causes the pivot point 540 that pivotably couples the blade(s) 524 to the plunger 516 to move toward the pin 536 as shown in FIG. 48, which in turn causes the pin 536 to slide within the blade channel 538 and the blade 524 to pivot with respect to the plunger 516. In this way, the blade assembly 518 is configured to automatically deploy the at least one blade 524 when the plunger 516 moves to the retracted, active position. A movement of the plunger 516 in the opposite direction reverses this motion, causing the at least one blade 524 to retract back into the needle 506, as shown in FIG. 47. In some embodiments, the slider 526 is biased away from the pivot point 540 of the blades 524, such as with a spring 542.

In some embodiments, the blade channel 538 has a notch 544 at the end of the blade channel 538. When the plunger 516 reaches the retracted, active position, the blade 524 is fully deployed, and the pin 536 of the slider 526 inserts into the notch 544. This puts the walls of the notch 544 in a perpendicular position to any forces being applied to the blades 524 and helps to keep the blades 524 from being pushed back into the needle 506. Thus, the notch 544 is configured to help maintain the blades 524 in the deployed position. However, once the plunger 516 begins moving back towards the extended, inactive position, the pin 536 slides out of the notch 544 and allows the blades 524 to rotate back into the needle 506 as the plunger 516 moves to the extended, inactive position.

In some embodiments, the slider 526 provides a delay between when the plunger 516 begins moving within the needle 506 and when the blades 524 are deployed. This delay provides a safety feature by avoiding premature deployment of the blades 524 before they are needed for the incision. Instead, the blades 524 are deployed as the slots 522 enter the skin. In addition, this delay may stop the blades 524 from retracting prematurely because the blades will not retract until the plunger 516 has completely moved to the extended, inactive position. Thus, the incision created is more precisely formed and is more likely to effectively form a seal around the catheter 508 without causing the catheter 508 to buckle and fail.

Figure 49A:
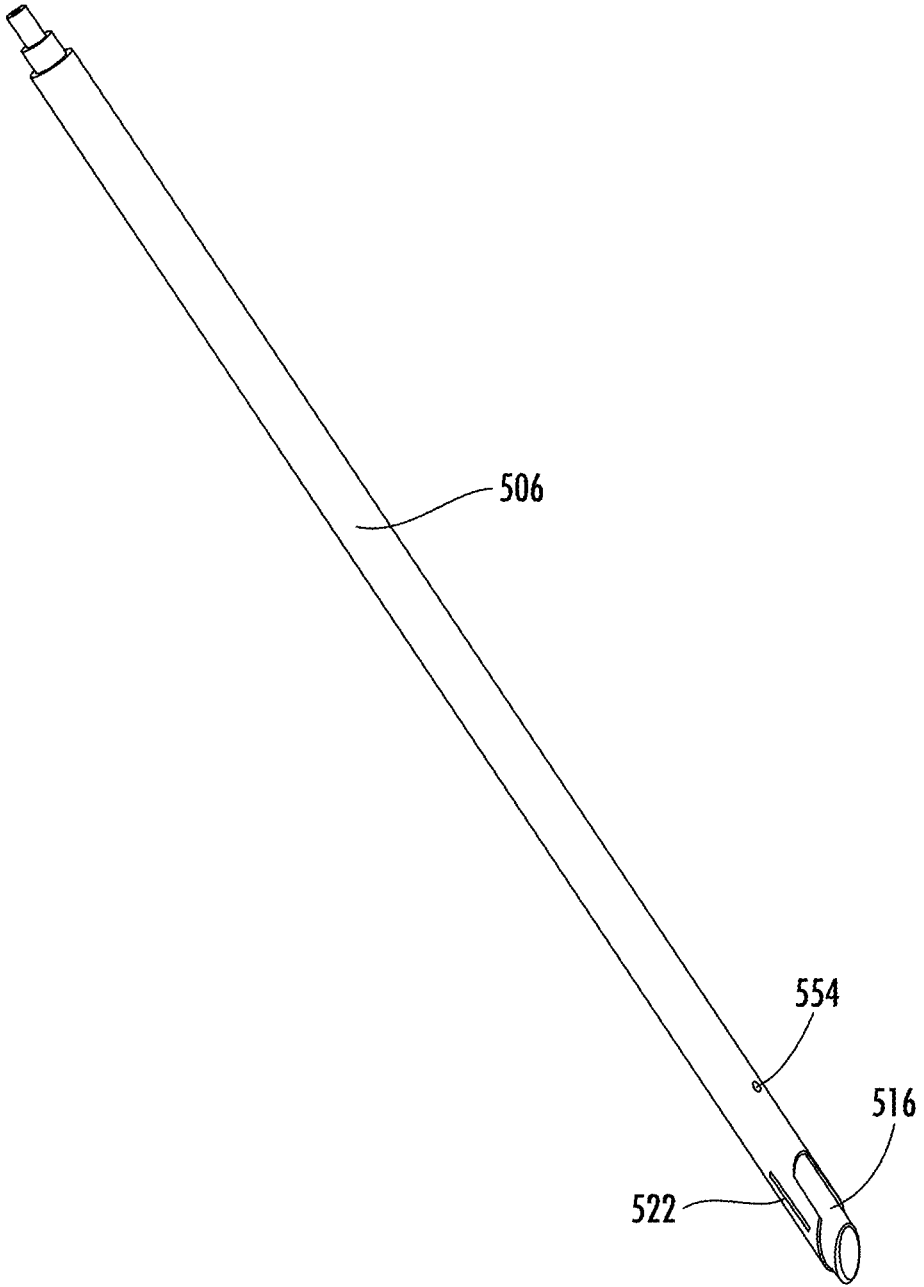
FIG. 49A is a perspective view of a needle assembly with the plunger in the extended position according to some embodiments.
Figure 49B:
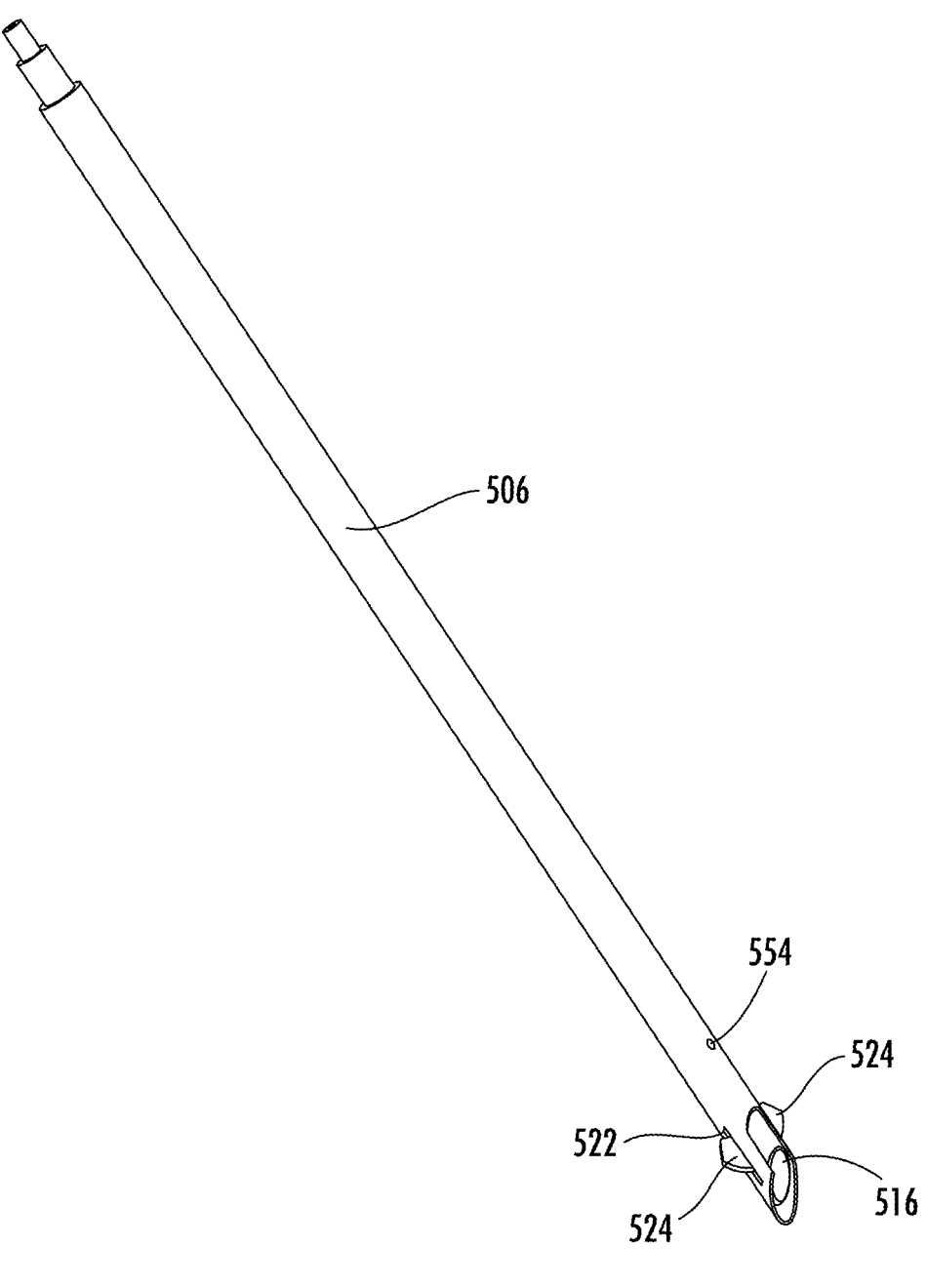
FIG. 49B is a perspective view of a needle assembly with the plunger in the retracted position according to some embodiments.

The needle assembly 500 may comprise a blade assembly 546 in place of the blade assembly 518, shown in FIGS. 49A-54B. Any of the features, aspects, or benefits of the blade assembly 518 described above may equally be applied in the blade assembly 546. The blade assembly 546 may include fewer components than the blade assembly 518 and may involve a simpler construction. FIGS. 49A and 49B illustrate the needle assembly 500 implemented with the blade assembly 546.

Figure 50:
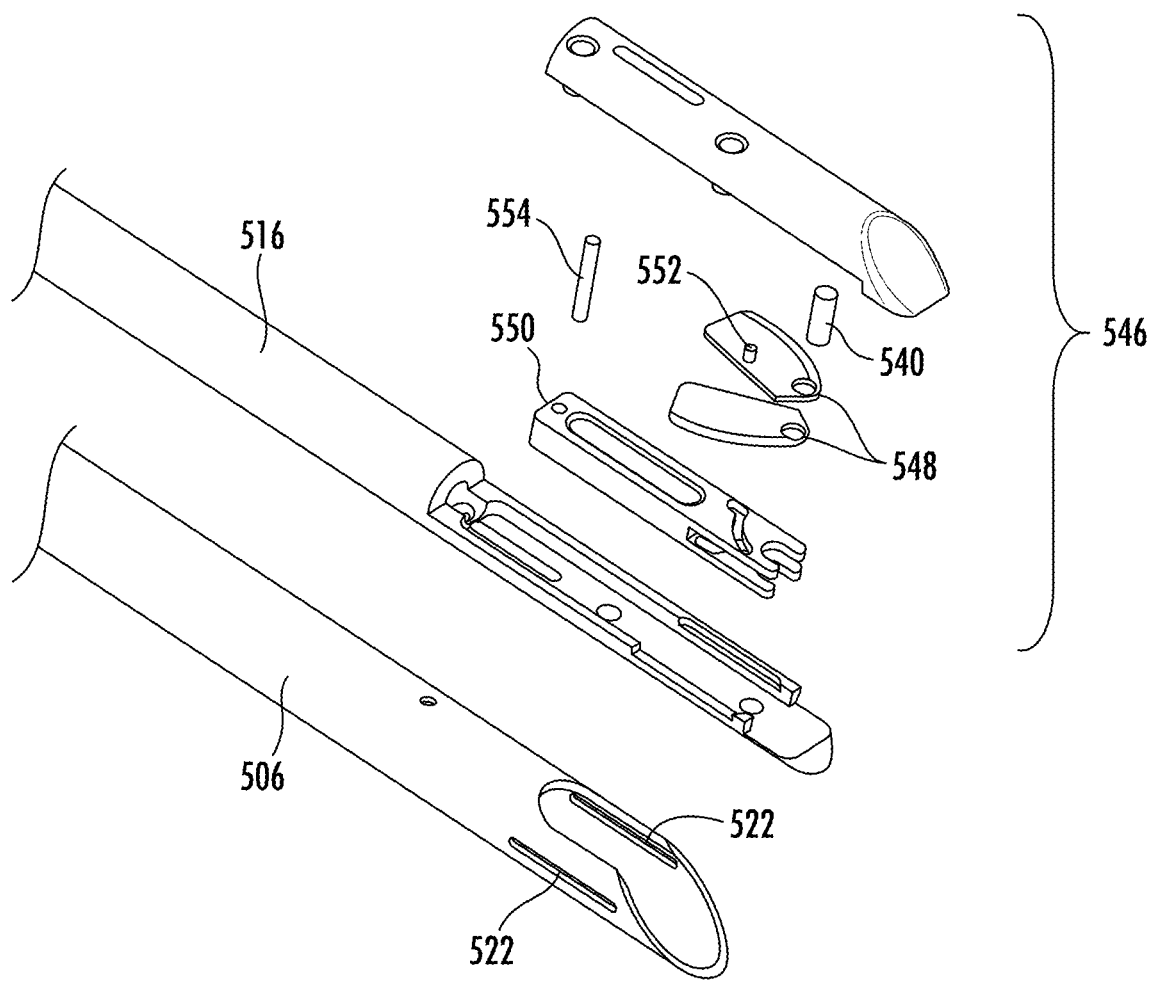
FIG. 50 is an exploded view of a blade assembly according to some embodiments.
Figure 51:
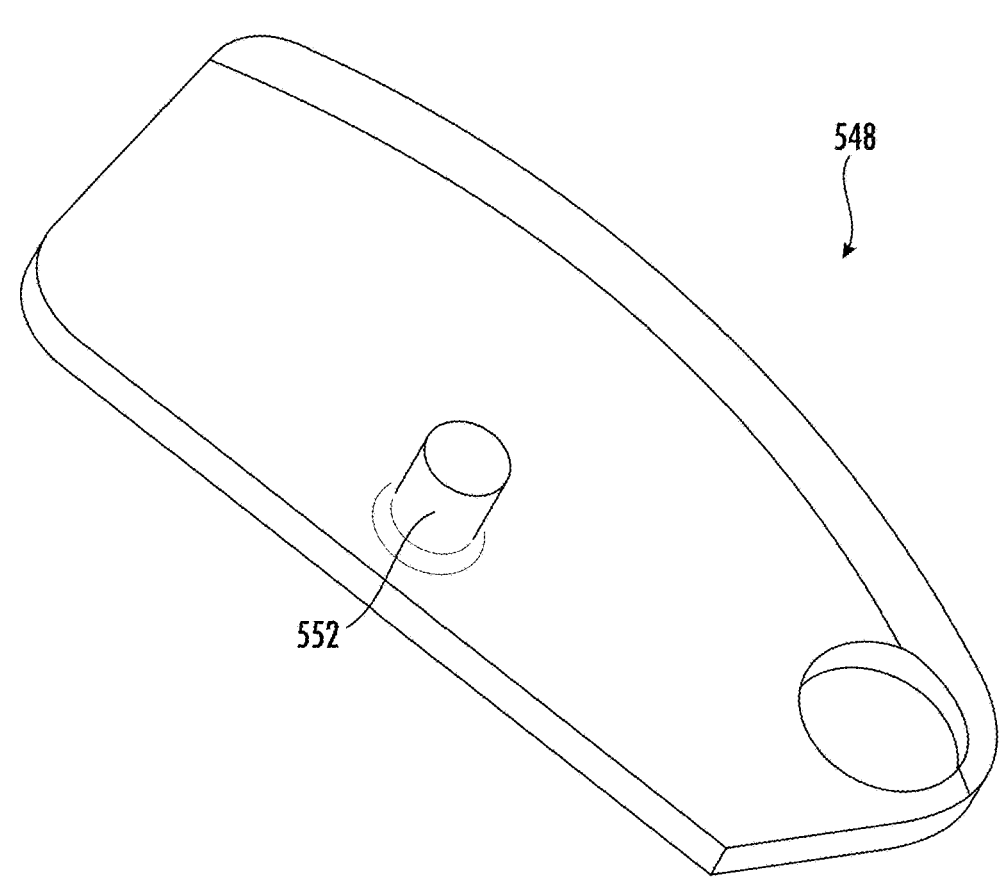
FIG. 51 is a perspective view of a blade of a blade assembly according to some embodiments.
Figure 52:
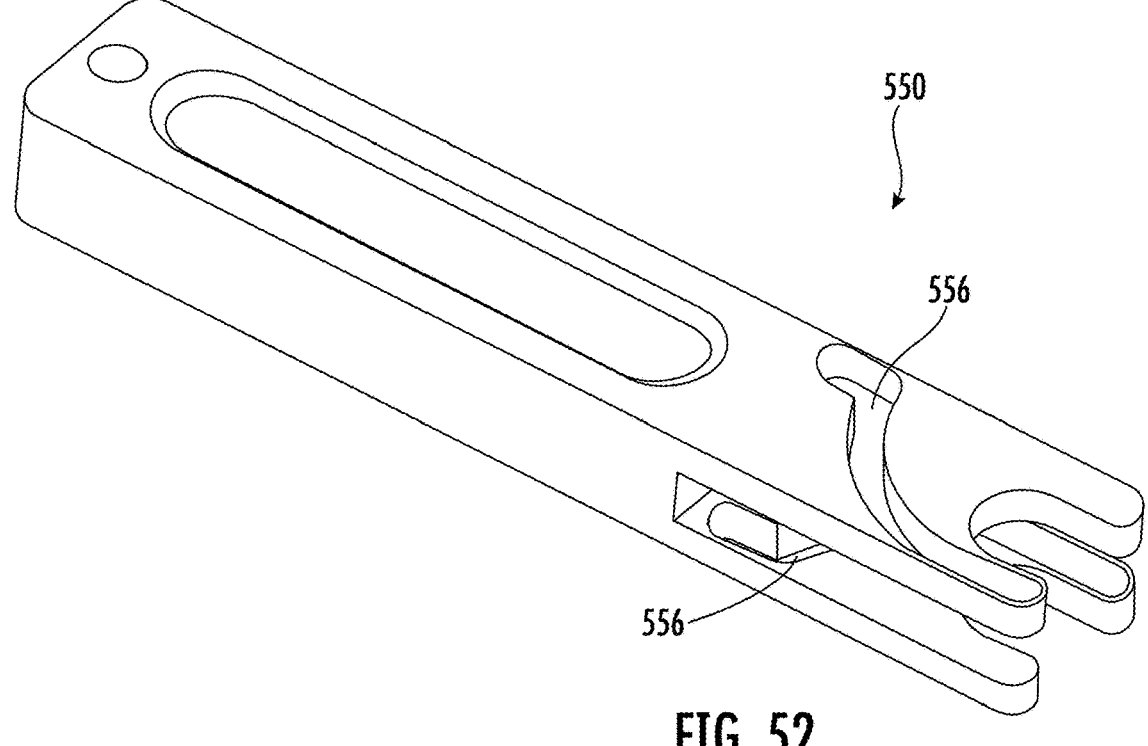
FIG. 52 is a perspective view of a slider of a blade assembly according to some embodiments.
Figures 53A, 53B:
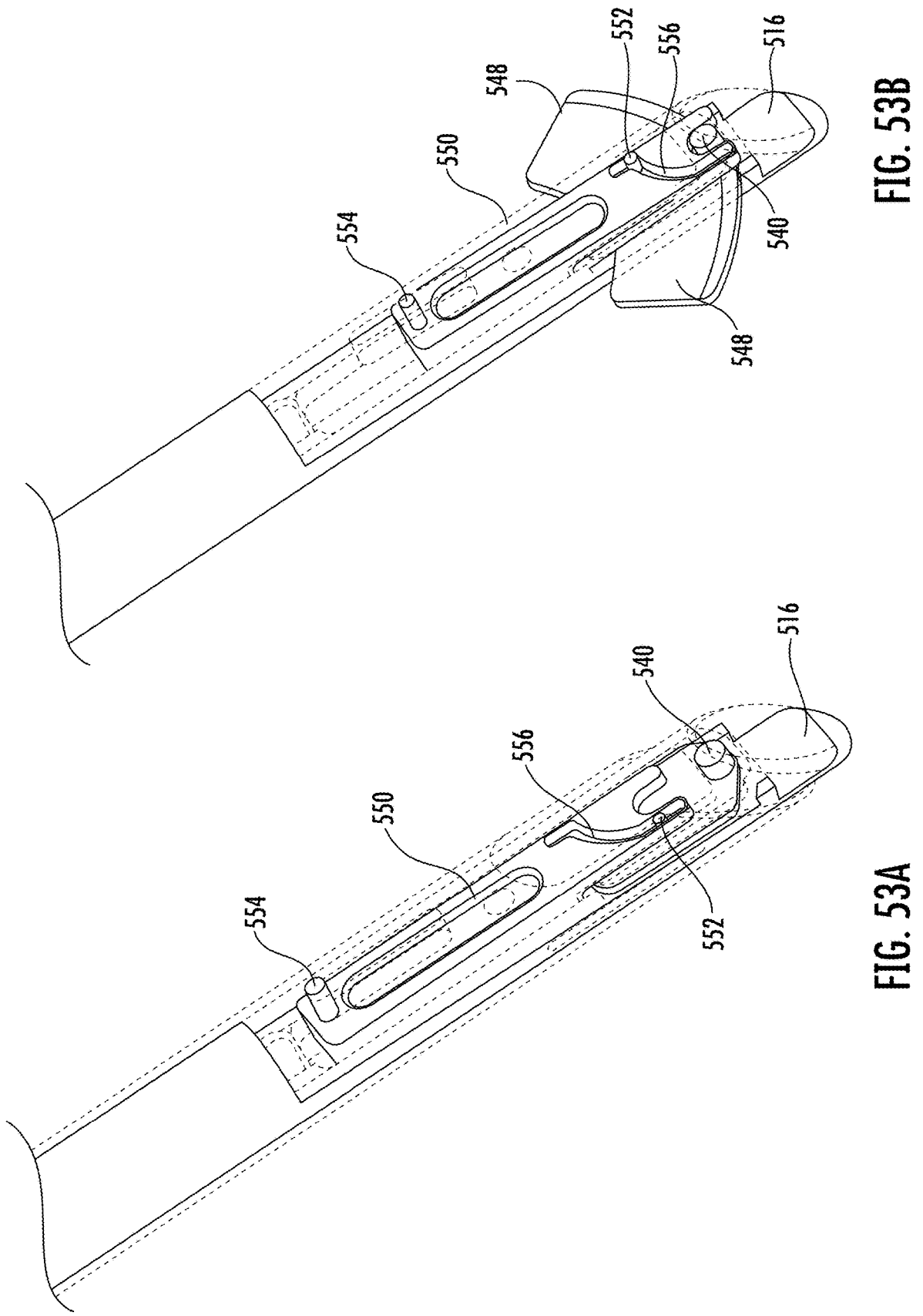
FIG. 53A is a close-up view of an end of a needle assembly with the plunger in the extended position according to some embodiments.
FIG. 53B is a close-up view of an end of a needle assembly with the plunger in the retracted position according to some embodiments.
Figure 54A:
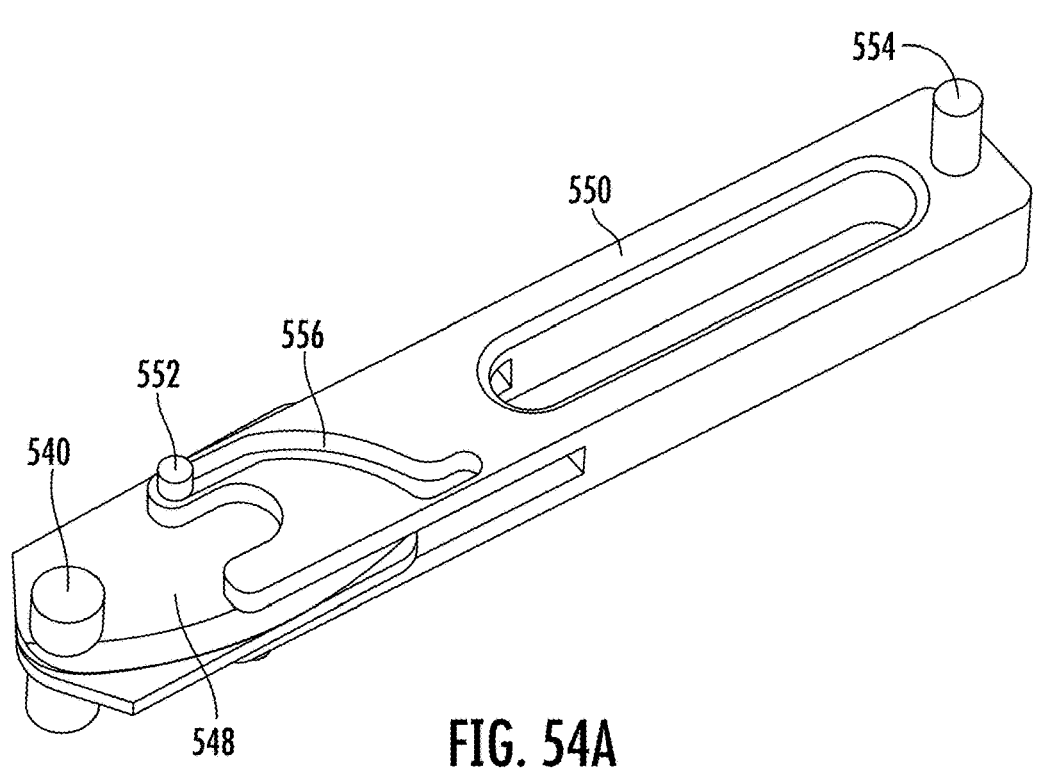
FIG. 54A is a close-up view of a blade assembly in the retracted position according to some embodiments.
Figure 54B:
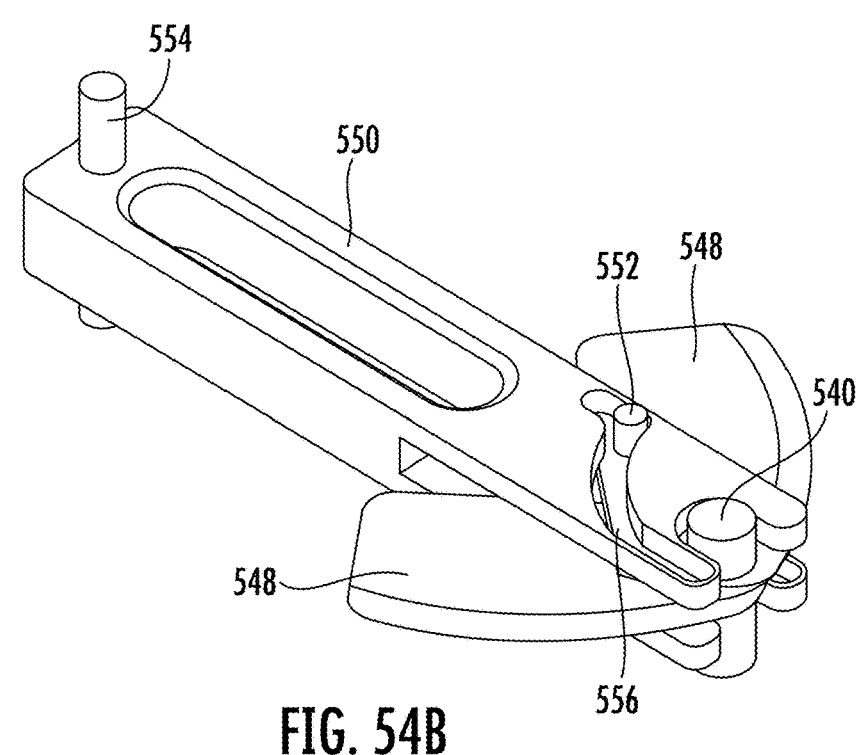
FIG. 54B is a close-up view of a blade assembly in the deployed position according to some embodiments.

As shown in FIGS. 50-52, the blade assembly 546 may comprise one or more blades 548 and a slider 550. Each blade 548 includes a guide pin 552 and is pivotably coupled to the plunger 516 about a pivot point 540. The slider 550 has a knob 554 that is similar to the knob 528, but instead of coupling with the needle 506 through a needle channel 530 like the knob 528, the knob 554 fixedly couples with the needle 506. Thus, the slider 550 is fixed with respect to the needle 506. Each blade 548 is configured to couple with the slider 550 through a slider track 556 of the slider 550. The guide pin 552 of each blade 548 is slidably coupled with one of the slider tracks 556 of the slider 550.

When the plunger 516 moves from the extended, inactive position to the retracted, active position, the pivot point 540 moves inward within the needle 506. This pushes the pivot point 540 toward the slider 550 and moves the guide pin 552 of each blade 548 along the slider track 556, which directs each blade 548 in its motion from the retracted position to the deployed position, as shown in FIGS. 53A-54B. The slider track 556 may be shaped, configured, or designed to delay, accelerate, decelerate, and/or lock the motion of the blade 548 as desired by changing the shape of the slider track 556. As with the notch 544 described above, the slider track 556 is configured to provide a wall that is perpendicular to forces applied to the blade 548 while in the deployed position, helping to keep the blade 548 from being pushed back into the needle 506. The slider track 556 is therefore configured to help maintain the blade 548 in the deployed position. However, once the plunger 516 begins moving back towards the extended, inactive position, the guide pin 552 allows the blade 548 to rotate back into the needle 506 as the plunger 516 moves to the extended, inactive position.

As will be apparent to one of skill in the art, having the blade assembly 518 or the blade assembly 546 be a part of the needle assembly 500, the user does not need to separately cut an incision before inserting the needle 506. Additionally, the blade assembly 518 and the blade assembly 546 automatically cut the incision to the correct width, depth, and location and help make sure the catheter 508 does not buckle or accordion.

In some embodiments, the blade assembly 546 is replaced by a blade assembly 576, illustrated in FIGS. 85A-85D, 86A-86B, and 87A-87B. Any of the features, aspects, or benefits of the blade assembly 518 and the blade assembly 546 described above may equally be applied in the blade assembly 576. The blade assembly 576 may include fewer components than the other blade assemblies and may involve a simpler construction.

Figure 85B:
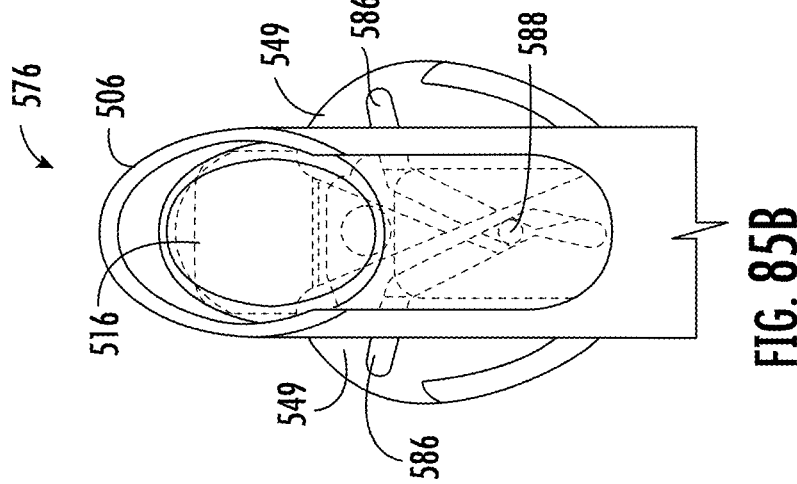
FIGS. 85A-85D illustrate blade deployment of a blade assembly as the plunger moves from an extended, inactive position to a retracted, active position according to some embodiments.
Figure 85A:
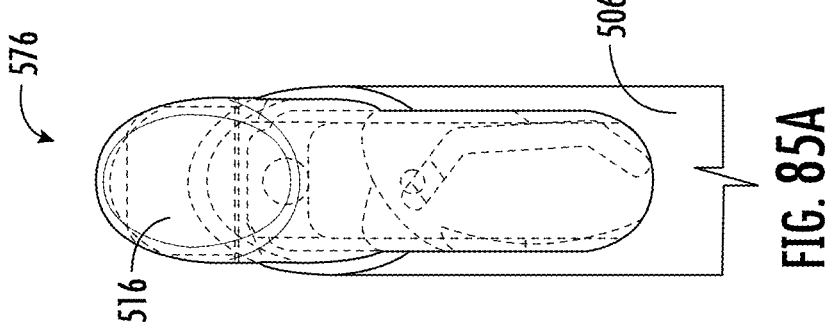
Figure 85D:
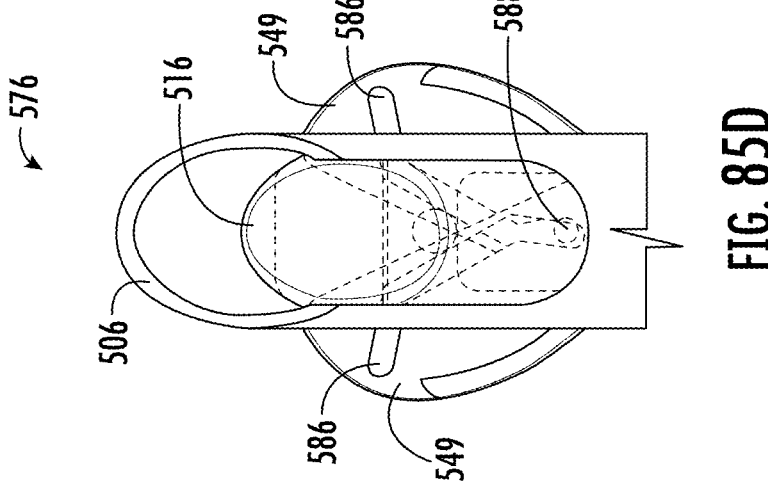
Figure 85C:
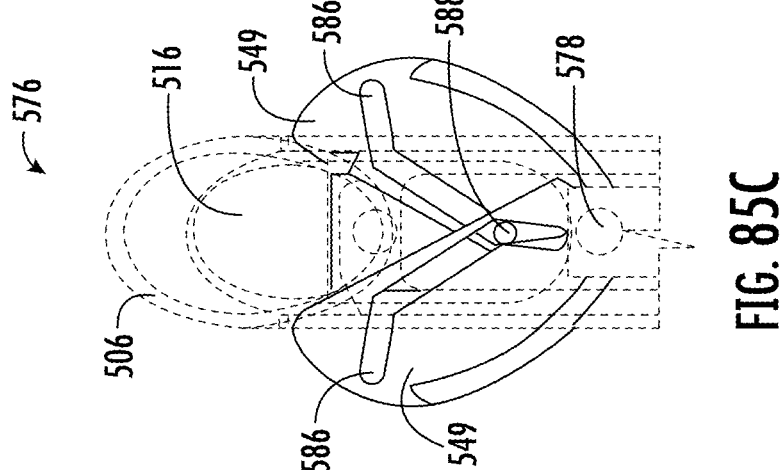
Figures 87A, 87B:
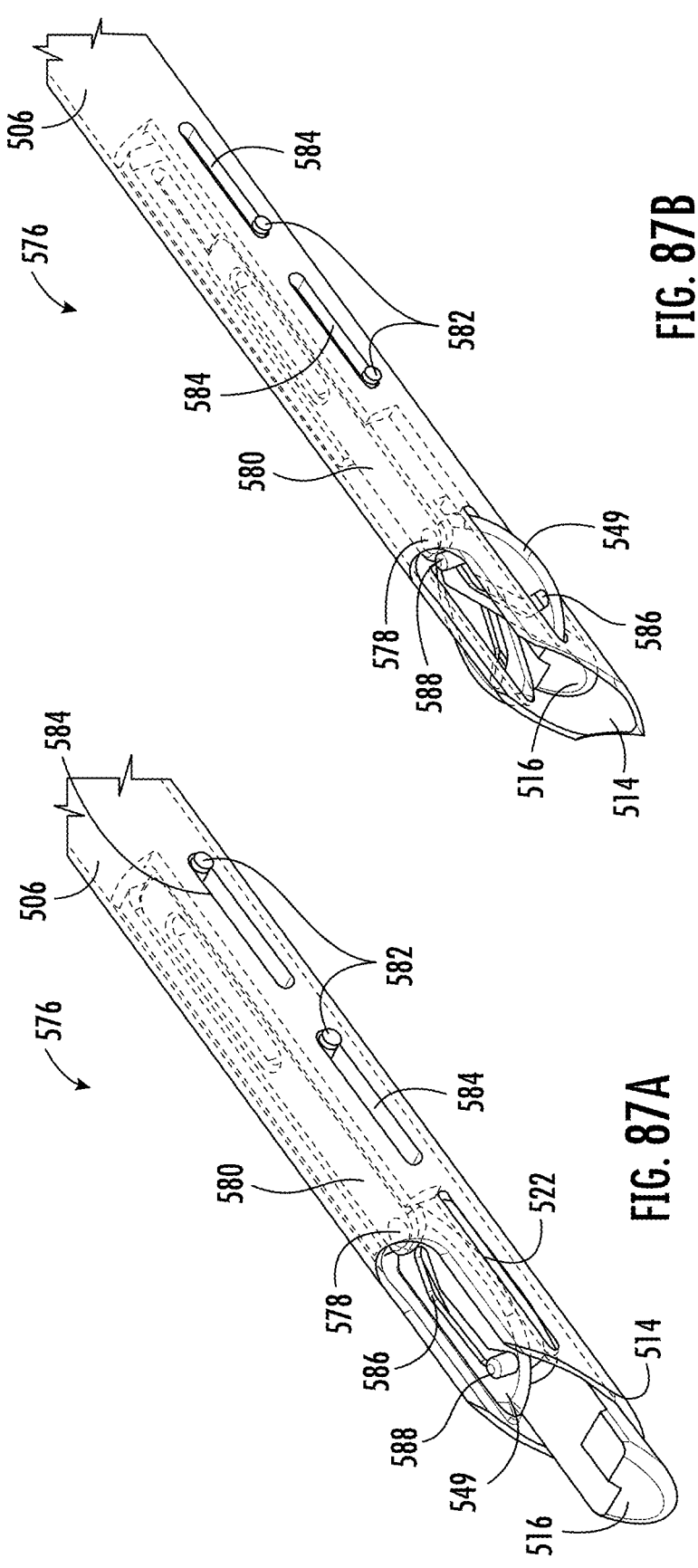
FIGS. 87A-87B illustrate blade deployment of a blade assembly according to some embodiments.

In some embodiments, the blade assembly 576 is pivotably coupled to the needle 506 about a pivot point 578 (shown in FIG. 85C and in FIGS. 87A-87B). This pivot point 578 may be fixed with respect to the needle 506. For example, the pivot point 578 may be positioned on an internal beam 580 inside of the needle 506. The internal beam 580 may be fixed with respect to the needle 506, such as through the use of at least one transverse pin 582 that extends through the needle 506 and through the internal beam 580. Thus, in some embodiments, when the plunger 516 moves back and forth between the extended, inactive position and the retracted, active position, the internal beam 580, and therefore the pivot point 578, remains fixed in place with respect to the needle 506. This allows the blades 549 to be positioned closer to the needle end 514 of the needle 506 and prevents them from travelling backward as the plunger 516 moves back within the needle 506. In some embodiments, the blades 549 are shaped and configured to aid in travel and cut in both directions.

The plunger 516 may be moveable between an extended, inactive position and a retracted, active position, as described above. In some embodiments, the plunger 516 comprises at least one transverse pin track 584. The transverse pin track 584 is configured to slidably couple with the at least one transverse pin 582 that fixes the internal beam 580 described above with respect to the needle 506. The transverse pin track 584 allows the plunger 516 to move within the needle 506. In some embodiments, the transverse pin track 584 is configured to control a range of motion of the plunger 516 with respect to the needle 506. This occurs because when the transverse pin 582 reaches either end of the transverse pin track 584, the plunger 516 is prevented from moving further in that direction within the needle 506. In some embodiments, the transverse pin track 584 allows clearance for the transverse pin 582, and the plunger travel is limited by an end stop located at the end of the plunger 516, opposite the plunger end that is equipped with blades 549. This end stop configuration can limit both the extended, inactive position and the retracted, active position of the plunger.

The blade assembly 576 may have a blade channel 586 that is configured to slidingly engage with a plunger pin 588 coupled to the plunger 516, shown in FIGS. 85A-85D and 87A-87B. Thus, in some embodiments, while the pivot point 578 is fixed with respect to the needle 506, the plunger pin

588 is positioned on the plunger 516 and is configured to move with the plunger 516. When the plunger 516 moves away from the extended, inactive position toward the retracted, active position, the plunger pin 588 moves toward the pivot point 578, and therefore moves along the blade channel 586. As shown in FIGS. 85A-85D, in some embodiments, when the plunger 516 moves to the retracted, active position, the plunger pin 588 moves towards the pivot point 578 to deploy the at least one blade 549 through the at least one slot 522. In some embodiments, when the plunger 516 moves to the extended, inactive position, the plunger pin 588 moves away from the pivot point 578 to retract the at least one blade 549.

Thus, in some embodiments, the blade channel 586 is shaped to move the at least one blade 549 in and out of the deployed position. In some embodiments, the blade channel 586 is shaped to create a nonlinear relationship between a position of the plunger 516 within the needle 506 and deployment of the at least one blade 549 through the at least one slot 522. For example, in some embodiments, by the time that the plunger 516 reaches a position where the plunger 516 is flush with the needle end 514 of the needle 506, the at least one blade 549 is at least 75% deployed compared to a maximum deployment of the at least one blade 549. In some embodiments, maximum deployment of the blade 549 occurs when the plunger 516 reaches the retracted, active position. In particular embodiments, when the plunger 516 reaches the position flush with the needle end 514 of the needle 506, the blade 549 is at least 90% deployed compared to the maximum deployment. Thus, the rate of open, the distance or width of the blades created, and the travel dwell (where the plunger travels but the blade position does not change) may all be designed into the shape of the blade channel 586 within the blades 549.

Thus, in some embodiments, the needle assembly 500 for placing a catheter 508 comprises: a needle 506 positioned within the catheter 508 and having a hollow body 520 and a sharpened end 515; a plunger 516 positioned within and slidably coupled with the needle 506, wherein the plunger 516 is configured to move between an extended, inactive position and a retracted, active position, wherein, when in the extended, inactive position, the plunger 516 extends past the sharpened end 515 of the needle 506 and, when in the retracted, active position, the sharpened end 515 of the needle 506 extends past the plunger 516 and wherein the plunger 516 is biased toward the extended, inactive position; and a blade assembly 576 positioned within the needle 506 and coupled to the plunger 516, wherein the blade assembly 576 is configured to automatically deploy at least one blade 549 when the plunger 516 moves to the retracted, active position and automatically retract the at least one blade 549 when the plunger 516 moves to the extended, inactive position.

In some embodiments, the needle assembly 500 comprises: a needle 506 having a hollow body 520 and a sharpened end 515; a plunger 516 positioned within and slidably coupled with the needle 506, wherein the plunger 516 is configured to move between an extended, inactive position and a retracted, active position, wherein, when in the extended, inactive position, the plunger 516 extends past the sharpened end 515 of the needle 506 and, when in the retracted, active position, the sharpened end 515 of the needle 506 extends past the plunger 516; and a blade assembly 576 positioned within the needle 506 and coupled to the plunger 516, wherein the blade assembly 576 is configured to automatically deploy at least one blade 549 when the plunger 516 moves to the retracted, active position.

In some embodiments, the needle assembly 500 comprises: a needle 506 having a hollow body 520; a plunger 516 positioned within and slidably coupled with the needle 506, wherein the plunger 516 is configured to move between an extended, inactive position and a retracted, active position; and a blade assembly 576 positioned within the needle 506 and coupled to the plunger 516, wherein the blade assembly 576 is configured to automatically deploy at least one blade 549 when the plunger 516 moves to the retracted, active position.

The needle 506 may be positioned within a catheter 508. The plunger 516 may be biased toward the extended, inactive position. The blade assembly 576 may be configured to automatically retract the at least one blade 549 when the plunger 516 moves to the extended, inactive position. The blade 549 may be pivotably coupled to the needle 506 about a pivot point 578. The pivot point 578 may be fixed with respect to the needle 506. The blade 549 may have a blade channel 586 configured to slidably engage with a plunger pin 588 coupled to the plunger 516. The blade channel 586 may be shaped to create a nonlinear relationship between a position of the plunger 516 within the needle 506 and deployment of the blade 549. When the plunger 516 moves to the retracted, active position, the plunger pin 588 may move towards the pivot point 578 to deploy the at least one blade 549 and when the plunger 516 moves to the extended, inactive position, the plunger pin 588 may move away from the pivot point 578 to retract the at least one blade 549. The pivot point 578 may be positioned on an internal beam 580 inside of the needle 506. The internal beam 580 may be fixed with respect to the needle 506 with at least one transverse pin 582 extending through the needle 506 and the internal beam 580. The plunger 516 may comprise at least one transverse pin track 584 configured to slidably couple with the at least one transverse pin 582. The at least one transverse pin track 584 may be configured to control a range of motion of the plunger 516 with respect to the needle 506. The sharpened end of the needle 506 may comprise a pointed, piercing tip 515 configured to reduce a force required to puncture skin of a patient. When the plunger 516 reaches a position where the plunger 516 is flush with the sharpened end of the needle 506, the at least one blade 549 may be at least 75% deployed compared to a maximum deployment of the at least one blade 549.

Figure 55:
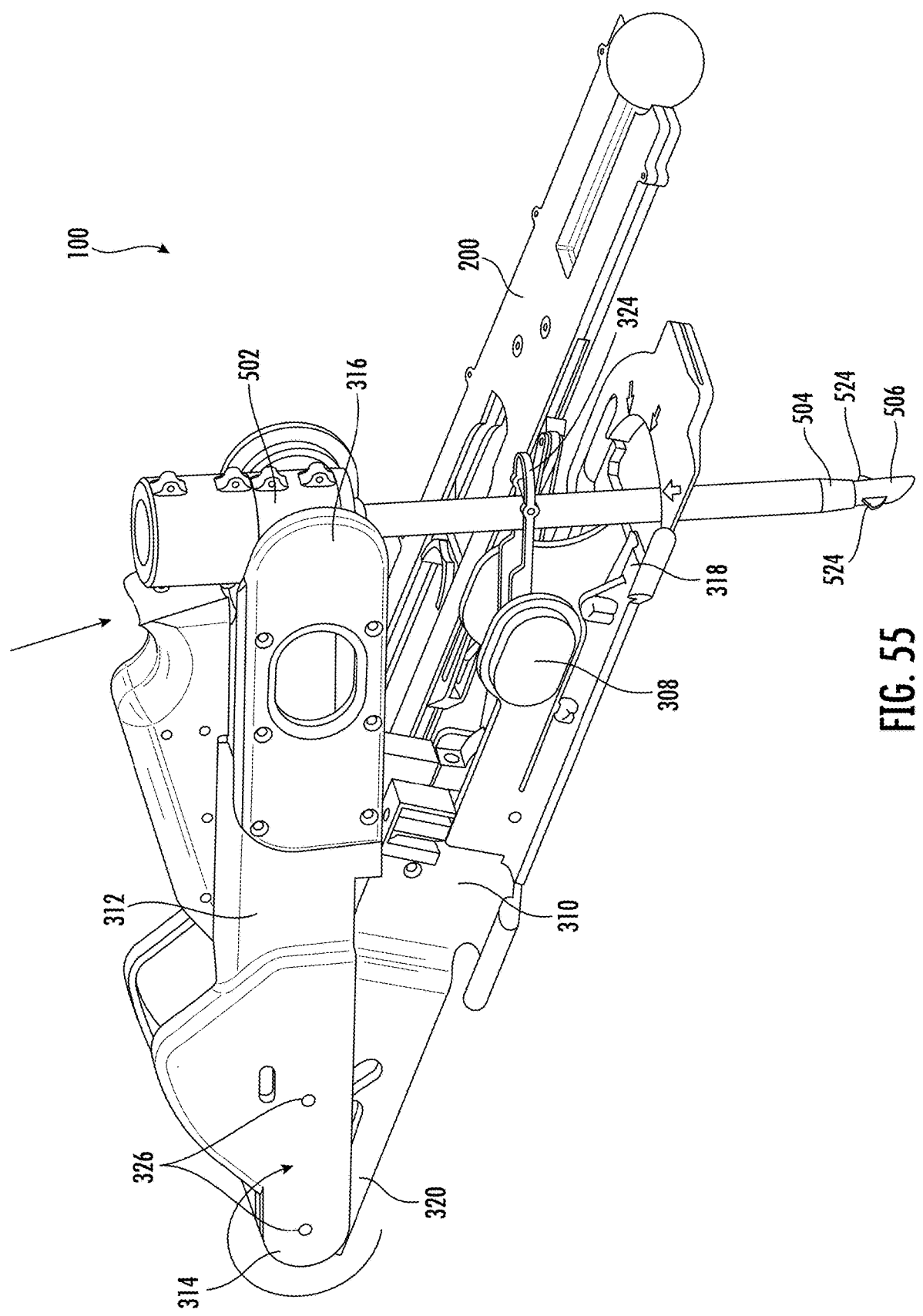
FIG. 55 is a perspective view of a needle thoracostomy device in between the raised position and the deployed position according to some embodiments.
Figure 56:
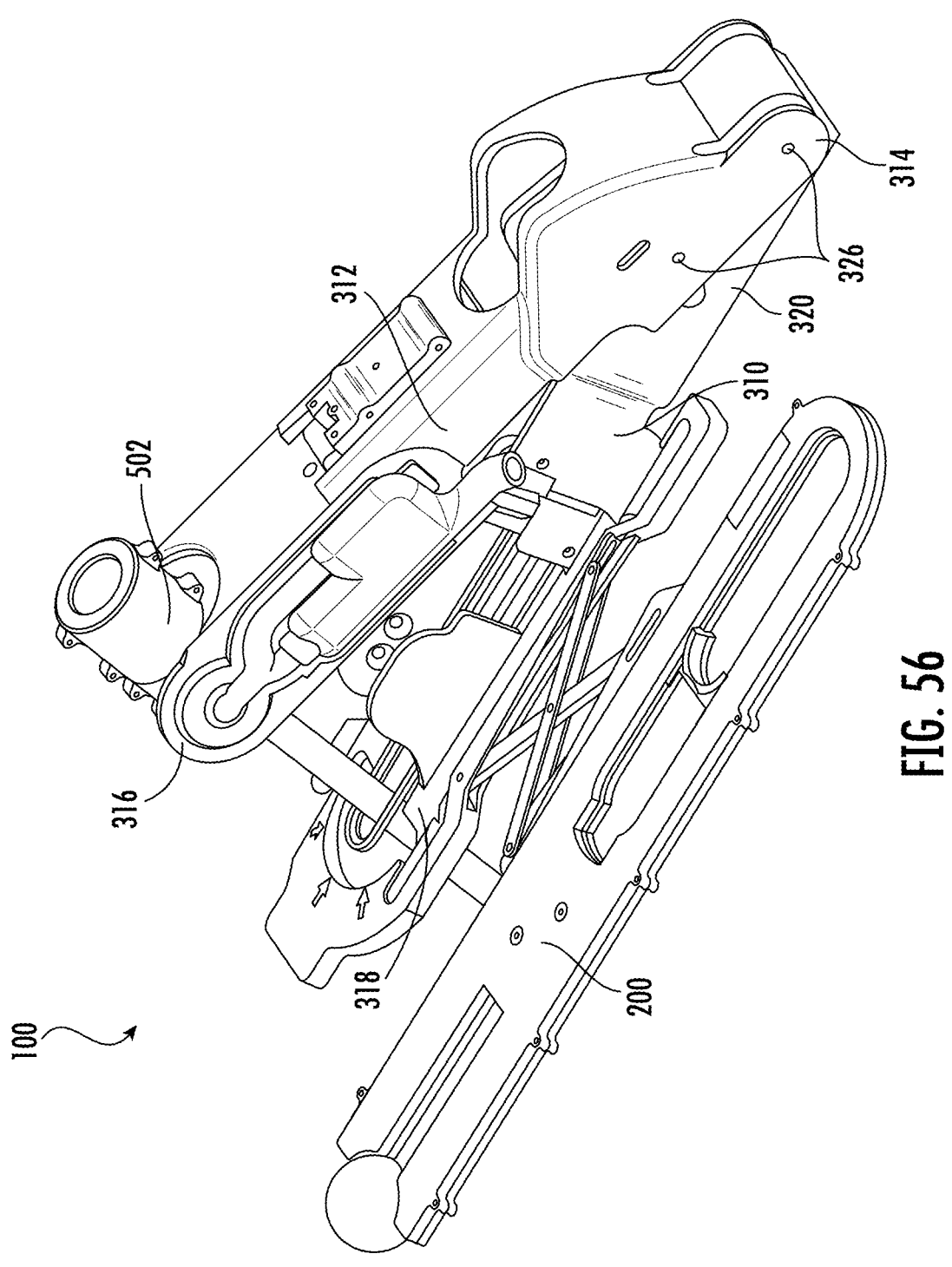
FIG. 56 is a perspective view of a needle thoracostomy device in between the raised position and the deployed position according to some embodiments.

Once the needle thoracostomy device 100 is in the raised position with the lever 312 raised and the needle assembly 500 set, the needle thoracostomy device 100 can be moved towards the deployed position by lowering the lever 312 back toward the base 310 to insert the needle 506 and the catheter 508 into the patient (see FIGS. 55-56). In some embodiments, the hinge between the base 310 and the lever 312 is a simple hinge that allows rotation of the lever 312 with respect to the base 310 without allowing for any linear motion. However, in such embodiments, as the lever 312 lowers, inserting the needle 506 into the patient, the angle of the needle 506 changes drastically. To avoid this drastic change in needle angle, in some embodiments, a curved or arched needle may be used so that the needle 506 enters the patient at the same angle throughout the motion of the lever 312. In some embodiments, a needle 506 is used that is straight and a hinge 326 between the base 310 and the lever 312 is implemented that allows for both rotation and linear motion of the lever 312 with respect to the base 310. The rotation and linear motion are constrained by the hinge 326, shown in FIG. 31, so that the needle 506 is maintained at the desired angle throughout the motion of the lever 312 from the raised position to the deployed position. This is accomplished through the combination of two connection points, one being linear and the other being curved, as shown in FIGS. 57-58. Other methods of achieving motion along the axis 510 of the needle 506 with a constant angle will be apparent to one of skill in the art. Thus, the needle assembly 500 is axially restrained through a combination of linear motion of the second end 316 of the lever 312 as the needle thoracostomy device 100 moves from the raised position to the deployed position and maintaining the needle assembly 500 at a constant point along the base 310, as supported by the needle guide loop 324. The deployment device 300 may be configured to move the needle assembly 500 along the axis 510 of the needle 506 and may be configured to maintain the needle assembly 500 at a constant angle while moving from the raised position to the deployed position, as shown in FIGS. 57-58.

As has been explained above, during a needle thoracostomy, it is important for the needle 506 to reach the pleural cavity and then stop. If the needle 506 does not penetrate far enough, the air or blood in the pleural cavity cannot be drained, but if the needle 506 goes in too far, this could result in a punctured lung. The needle assembly 500 described herein is designed to penetrate to the correct depth and then stop to avoid further penetration. Further to this end, in some embodiments, a portion of the needle assembly 500 is configured to automatically decouple or detach from the lever 312 once the needle 506 has penetrated to the correct depth (FIGS. 55-58). When the needle assembly 500 detaches from the lever 312, the needle 506 is no longer attached to the deployment device 300 and therefore does not get pushed further into the patient as the catheter 508 is inserted the rest of the way into the patient and the needle thoracostomy device 100 reaches the deployed position.

Figure 32:
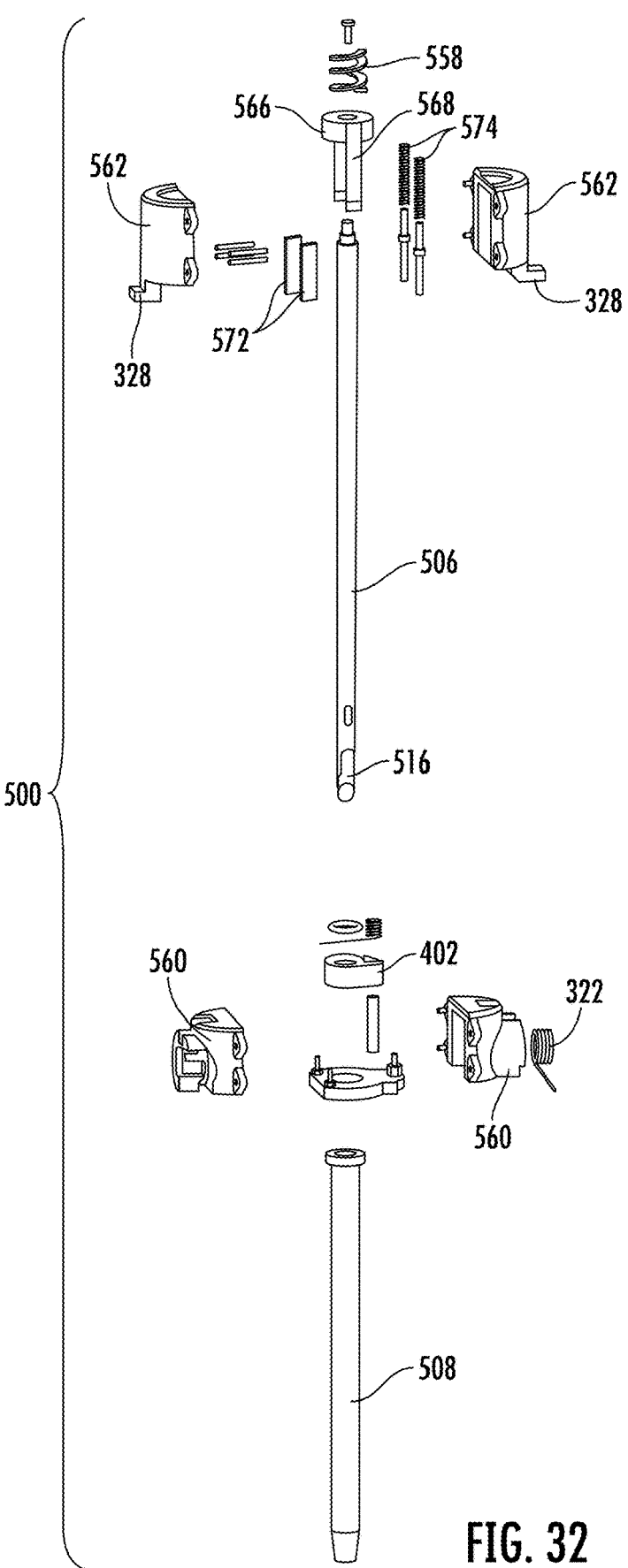
FIG. 32 is an exploded view of a needle assembly of a needle thoracostomy device according to some embodiments.
Figure 33:
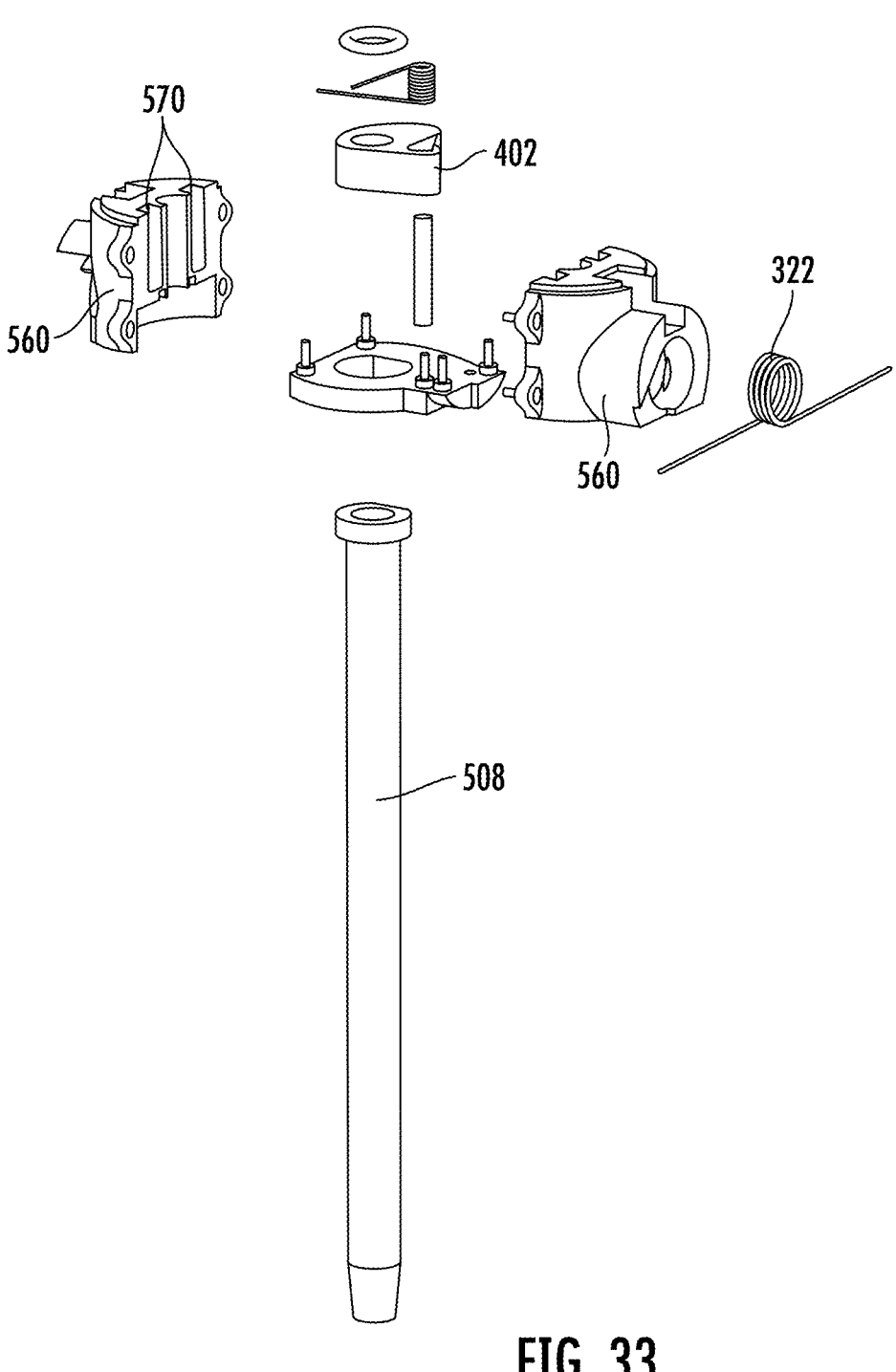
FIG. 33 is an exploded view of a catheter and valve head of a needle thoracostomy device according to some embodiments.

The needle assembly 500 is configured to automatically detach from the lever (FIG. 61) when two conditions are met. First, once the needle end 514 of the needle 506 is at least a predetermined distance below the base 310 and therefore the needle 506 has penetrated to a desired depth into the patient (FIGS. 57-58), and second, once the plunger 516 inside of the needle 506 moves out of the needle 506 to the extended, inactive position (FIG. 60A). The depth of penetration of the needle 506 may be determined by a rotational position of the needle assembly 500 with respect to the lever 312, as shown in more detail in FIGS. 57-58. Specifically, the hinged end 502 of the needle assembly 500 may have a pivot feature 328 (FIG. 59) that is positioned within the boundaries of a circular wall 330 on the lever 312 (FIGS. 31-32). As the needle assembly 500 is inserted into the patient and therefore rotates with respect to the lever 312, the pivot feature 328 moves along the circular wall 330, but is retained within the circular wall 330, holding the needle assembly 500 to the lever 312. The circular wall 330 may have a break 332 in the circular wall 330 that allows the needle assembly 500 to release from the lever 312 (see FIG. 31). This break 332 may be located so that the pivot feature 328 reaches the break 332 only when the needle assembly 500 has rotated to the angle that corresponds with the desired depth of penetration by the needle 506 into the patient, shown in FIG. 58. The desired depth may be at least 2 inches, or between 1 and 3 inches, or any other desired depth. The desired depth may be selected to correspond with an expected thickness of the chest wall. As will be described in more detail below, even if the pivot feature 328 reaches the break 332, the needle assembly 500 does not release from the lever 312 unless the plunger 516 extends out of the needle 506. The pivot feature 328 and circular wall 330 are configured to prevent early release of the needle assembly 500 from the deployment device 300 if the user reverses needle direction before the procedure is complete.

Figure 59:
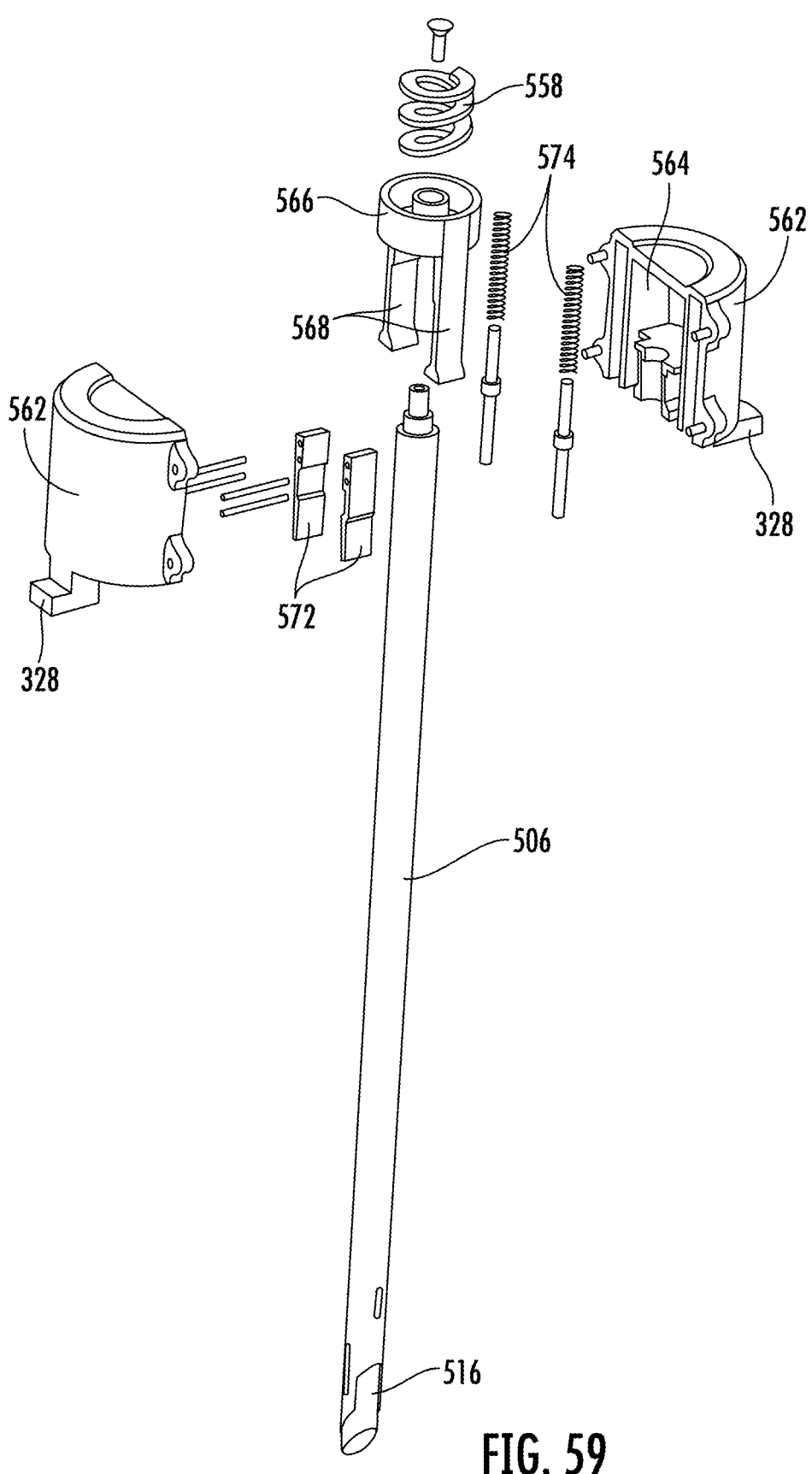
FIG. 59 is an exploded view of a needle assembly according to some embodiments.
Figure 60B:
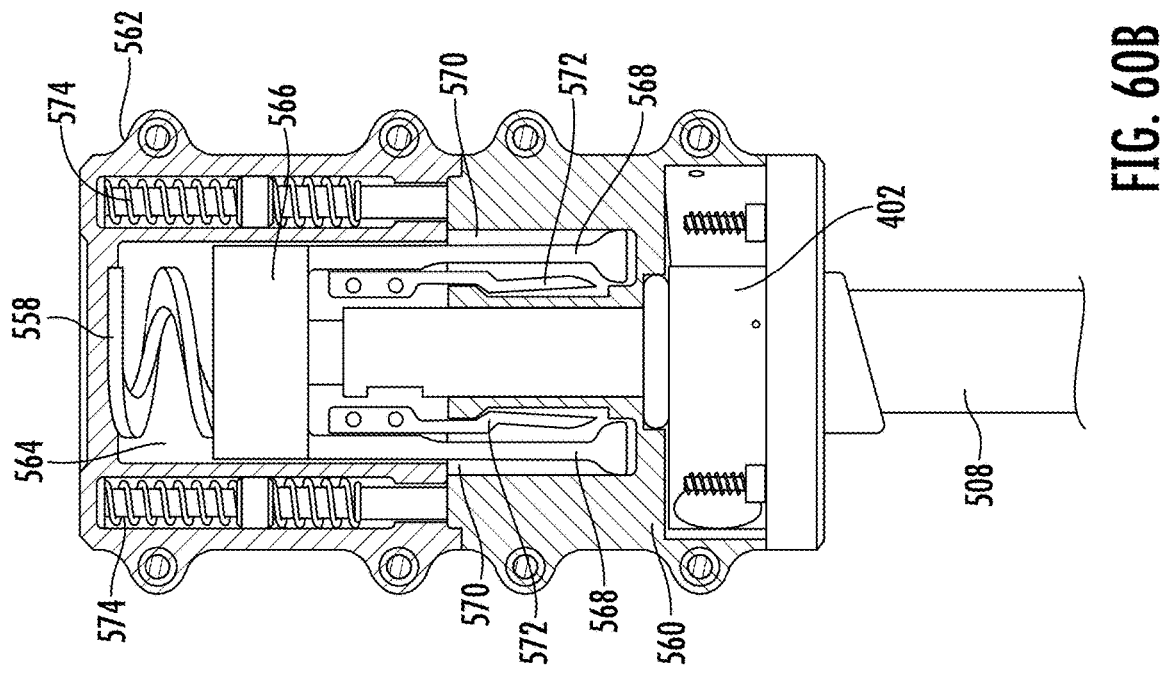
FIG. 60B is a close-up section view of a needle assembly showing the interior of the removable head and the valve head according to some embodiments.
Figure 60A:
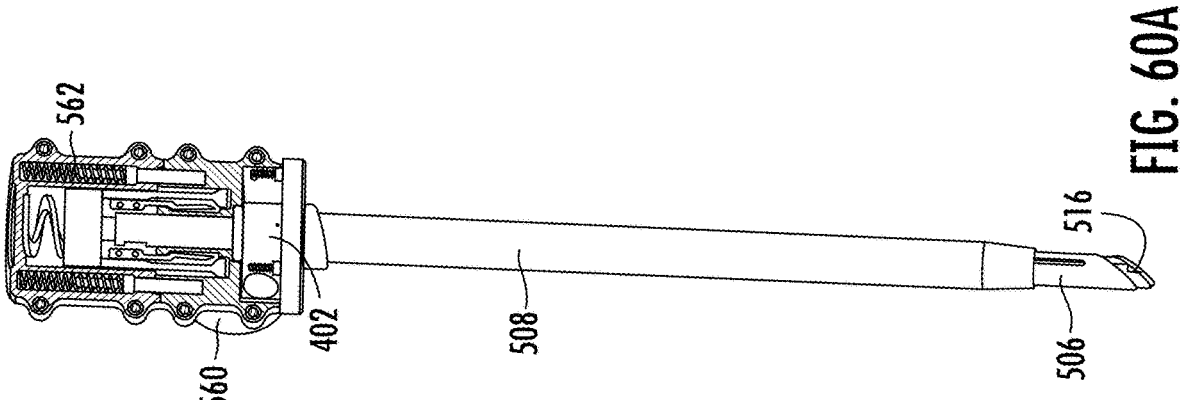
FIG. 60A is a section view of a needle assembly showing the interior of the removable head and the valve head according to some embodiments.

Turning to FIGS. 59, 60A, and 60B and as mentioned above, the plunger 516 is positioned within the needle 506 and is free to move within the needle 506. The plunger 516 may be biased toward the free end 504 of the needle assembly 500 and away from the hinged end 502 of the needle assembly 500. A spring 558 may be used to create this bias.

At the hinged end 502 of the needle assembly 500, the needle assembly 500 may have a valve head 560 that hingedly couples with the lever 312 as described above. The valve head 560 is configured to remain attached to the lever 312 even after the needle assembly 500 is removed, along with the catheter 508. The needle assembly 500 also has a removable head 562 that sits on the valve head 560 and is attached to the valve head 560 through the pivot feature 328 as described above. In addition, the removable head 562 has an interior cavity 564 that contains a plunger lock 566 with at least one feature stem 568 that extends into the valve head 560 through an opening 570 in the valve head 560. The feature stem 568 may be any shape, including a ball, a cylinder, triangular, or any other shape. The removable head 562 also has at least one tail 572 that extends through the same opening 570 into the valve head 560. When the plunger 516 moves toward the hinged end 502 of the needle assembly 500, the feature stem 568 engages with the tail 572, pushing the tail 572 outward and making the combination of the feature stem 568 and tail 572 larger than can fit out through the opening 570. In this way, while the plunger 516 is pushed toward the hinged end 502 of the needle assembly 500, such as when the needle 506 is actively entering the patient chest wall, the needle assembly 500 is unable to release from the lever 312. However, once the pressure on the end of the plunger 516 is relieved such that the plunger 516 is no longer pushed toward the hinged end 502 of the needle assembly, the bias of the plunger 516 causes the plunger 516 to return to the extended, inactive position, which causes the feature stem 568 to disengage from the tail 572 and both the feature stem 568 and the tail 572 can individually fit through the opening 570, allowing the needle assembly 500 to release from the lever 312, as long as the pivot feature 328 has rotated to the angle where the break 332 occurs in the circular wall 330. The removable head 562 may be biased away from the valve head 560 by one or more springs 574 such that, once the two conditions for release are met, the removable head 562 automatically pops out of the valve head 560. This helps to notify the user that both conditions have been met.

The plunger 516 helps determine when the needle end 514 of the needle 506 has cleared the chest wall and entered the pleural cavity. However, if the user were to start to pull the needle 506 back out of the patient, this would also trigger the release of the needle 506, and would do so prematurely. For this reason, the needle 506 must also have penetrated to the desired depth, as determined by the pivot feature 328 and circular wall 330 described above. Thus, the combination of the plunger 516 with the pivot feature 328 and circular wall 330 makes it so that the needle assembly 500 is not released prematurely, but also ensures that the needle assembly 500 releases before reaching the lungs, thus helping to avoid puncture of the lungs.

In some embodiments, the tail 572 is elongated such that it reaches through nearly the entire depth of the opening 570 into the valve head 560. Thus, when the plunger 516 is in any position that is even partially retracted, the feature stem 568 is engaged with the tail 572, and the plunger 516 cannot be removed. However, once the plunger 516 is completely extended, the tail 572 is no longer engaged with the feature stem 568, and both the feature stem 568 and the tail 572 can fit through the opening 570 in the valve head 560, allowing the needle assembly 500 to release from the lever 312, as long as the pivot feature 328 has rotated to the angle where the break 332 occurs in the circular wall 330, as described above.

Figures 88A, 88B:
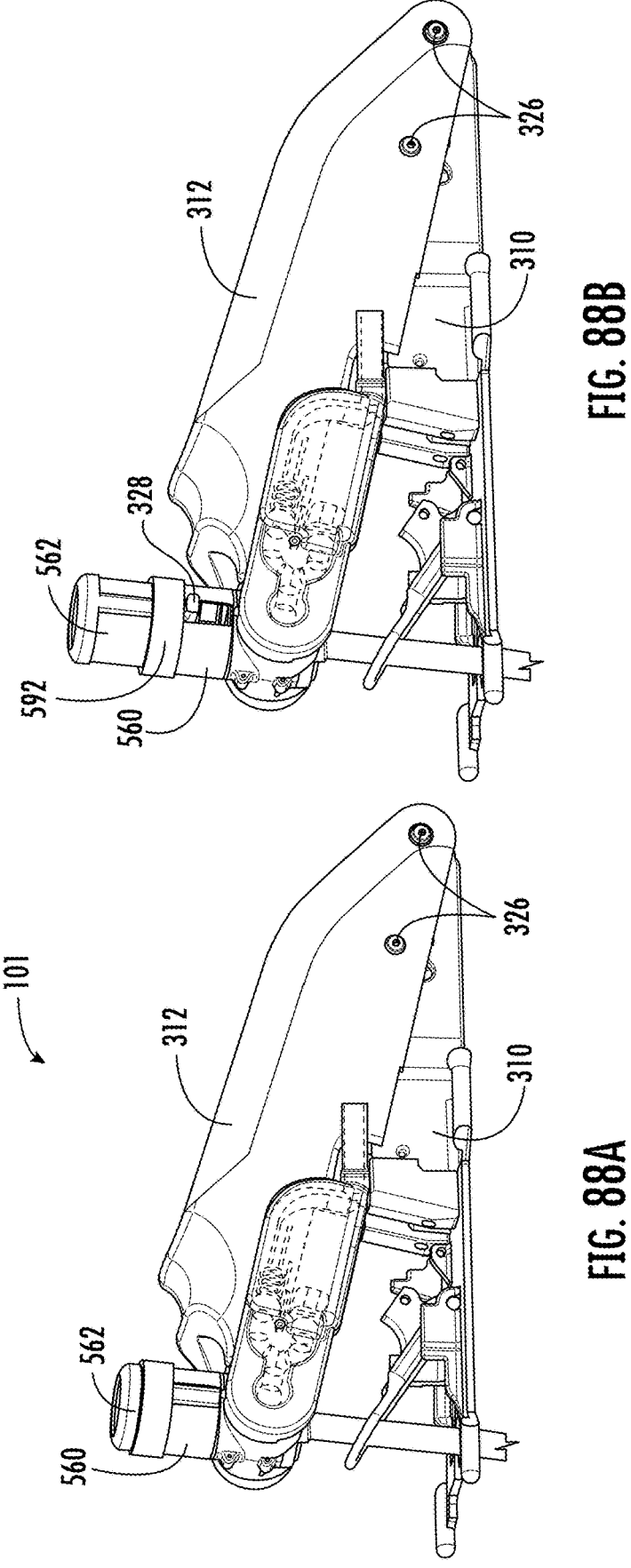
FIGS. 88A-88C illustrate a removable head of a needle assembly according to some embodiments.
Figure 88C:
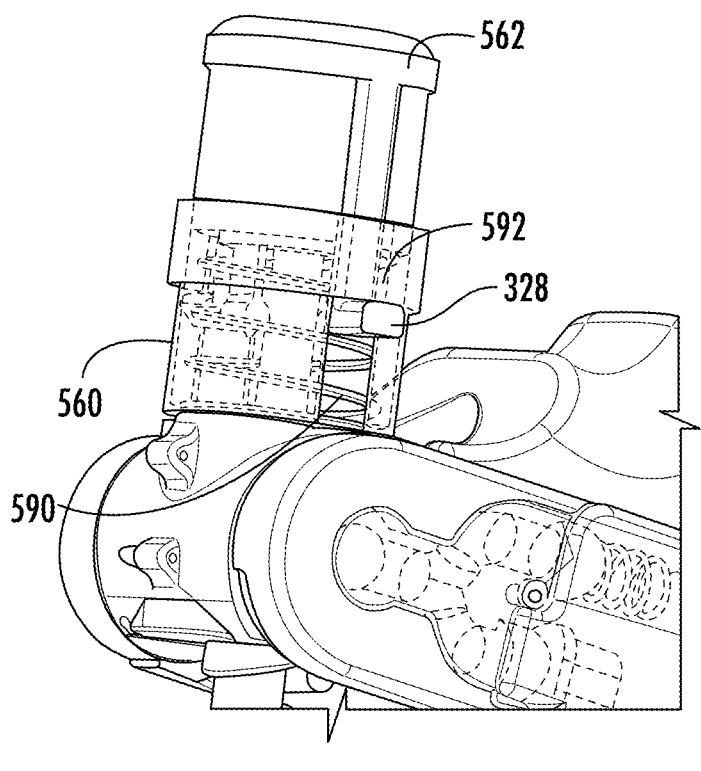

In some embodiments, springs 574 are replaced with a spring 590. The spring 590 may have any of the features discussed above with respect to the springs 574. Thus, the spring 590 may bias the removable head 562 away from the valve head 560 to eject the removable head 562 once the two conditions discussed above are met. The spring 590 may be sized to fill the valve head 560, as shown in FIGS. 88A-88C. This larger spring size allows a greater bias to be applied to the removable head 562 so that the user more easily notices when the removable head 562 disengages from the valve head 560. In other words, this allows the ejection of the removable head 562 to be finely tuned to set the eject pressure with both the spring preload and the spring rate. The removable head 562 may have a visual indicator, such as a red coloring, to show that the needle 506 has been ejected. The removable head 562 may also have a stop 592 at a max eject position to prevent the removable head 562 from ejecting in an uncontrolled manner. This may be accomplished by having the stop 592 positioned in the path of travel of the pivot feature 328 as the pivot feature 328 moves away from the valve head after passing through the break 332.

Figure 61:
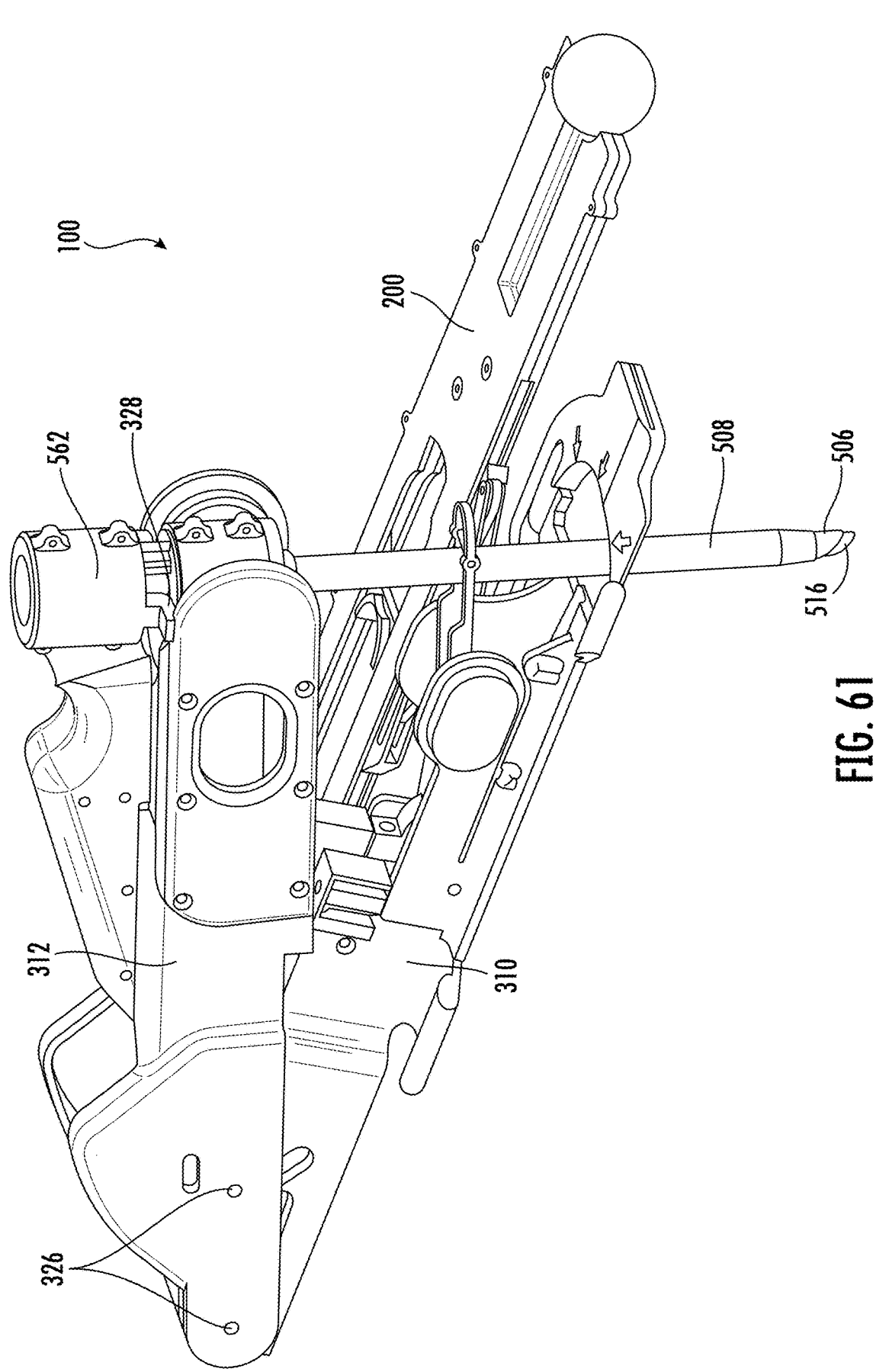
FIG. 61 is a perspective view of a needle thoracostomy device with the removable head being removed according to some embodiments.
Figure 62:
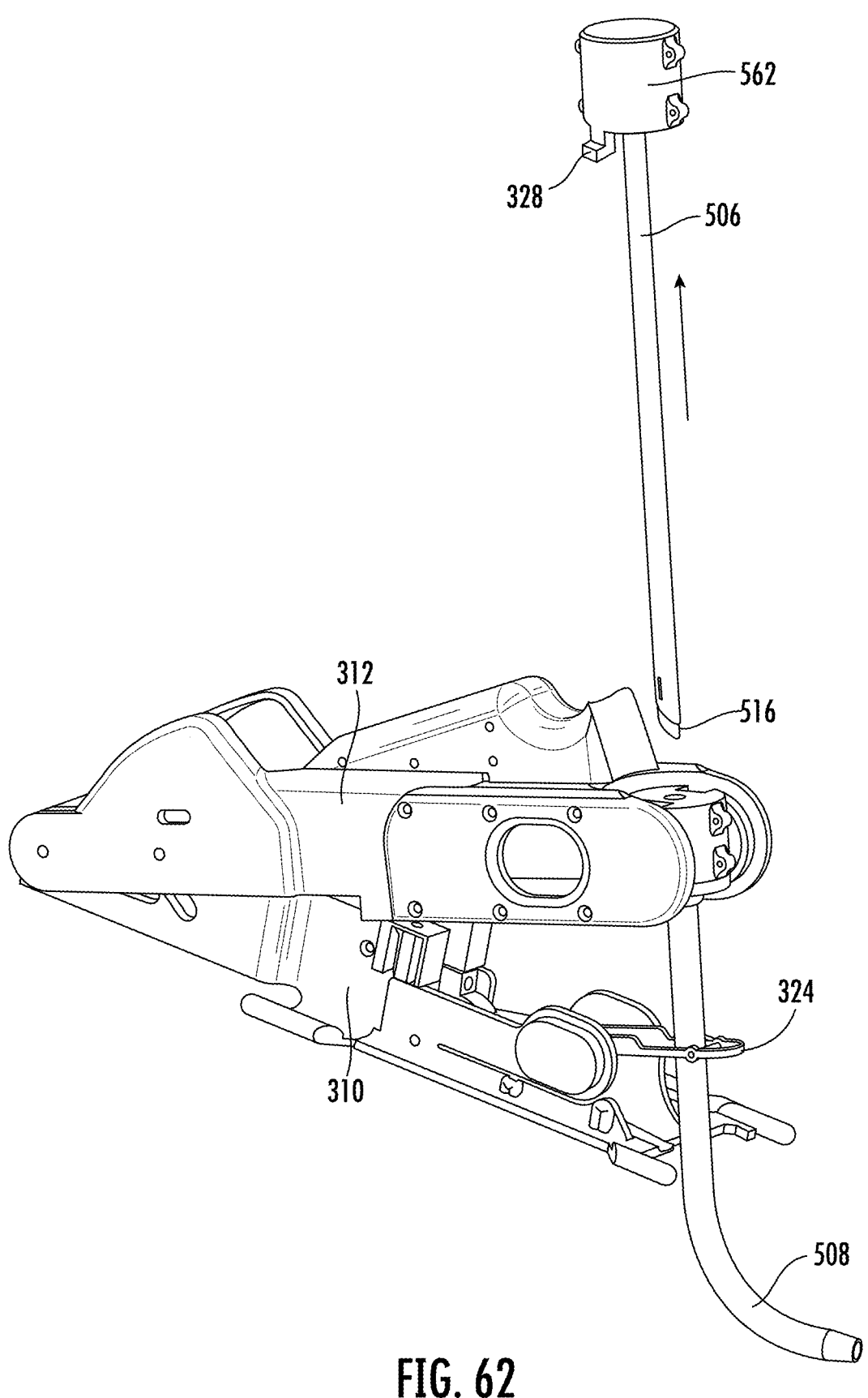
FIG. 62 is a perspective view of a needle thoracostomy device with the needle assembly removed according to some embodiments.
Figure 63:
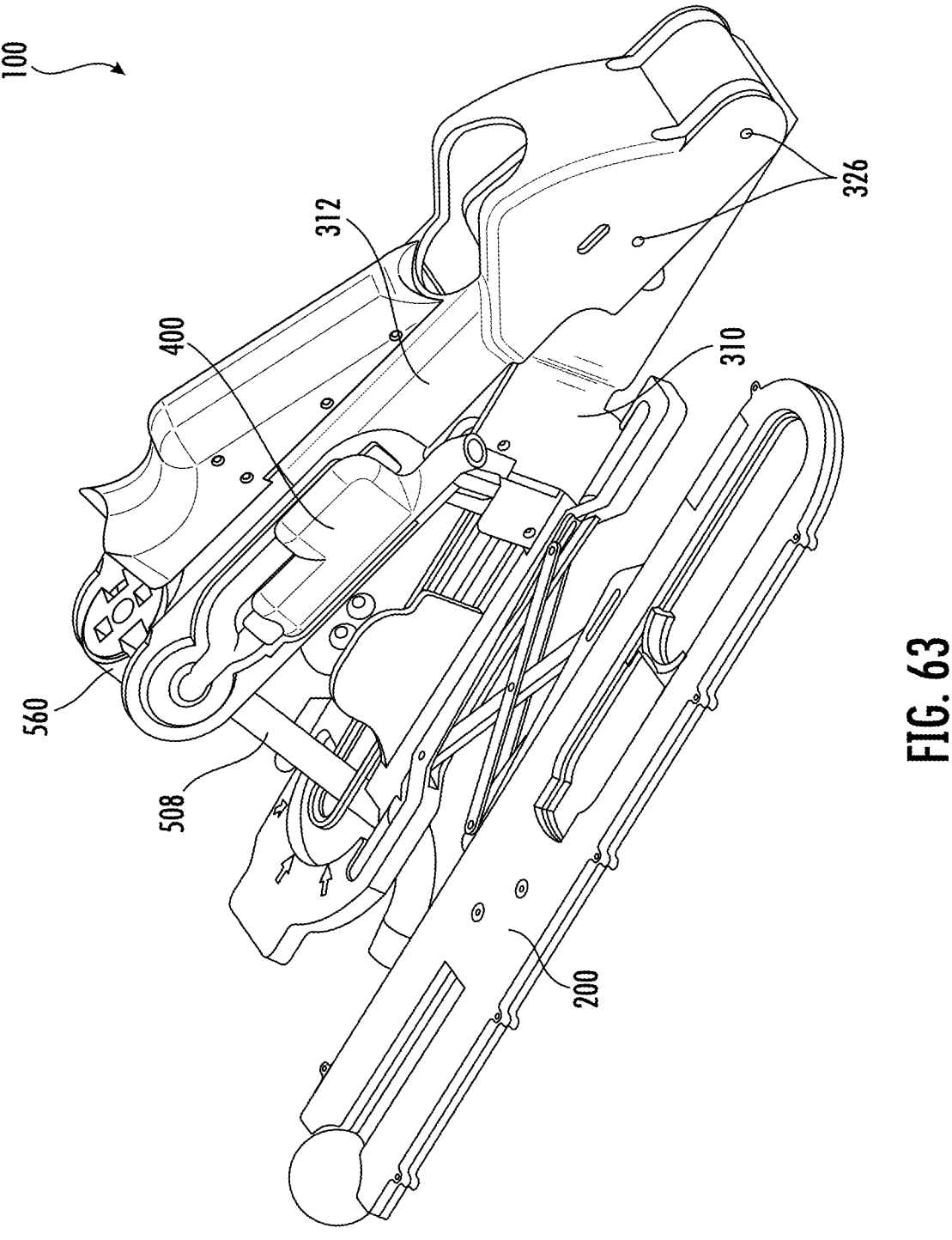
FIG. 63 is a perspective view of a needle thoracostomy device in between the raised position and the deployed position according to some embodiments.
Figure 64:
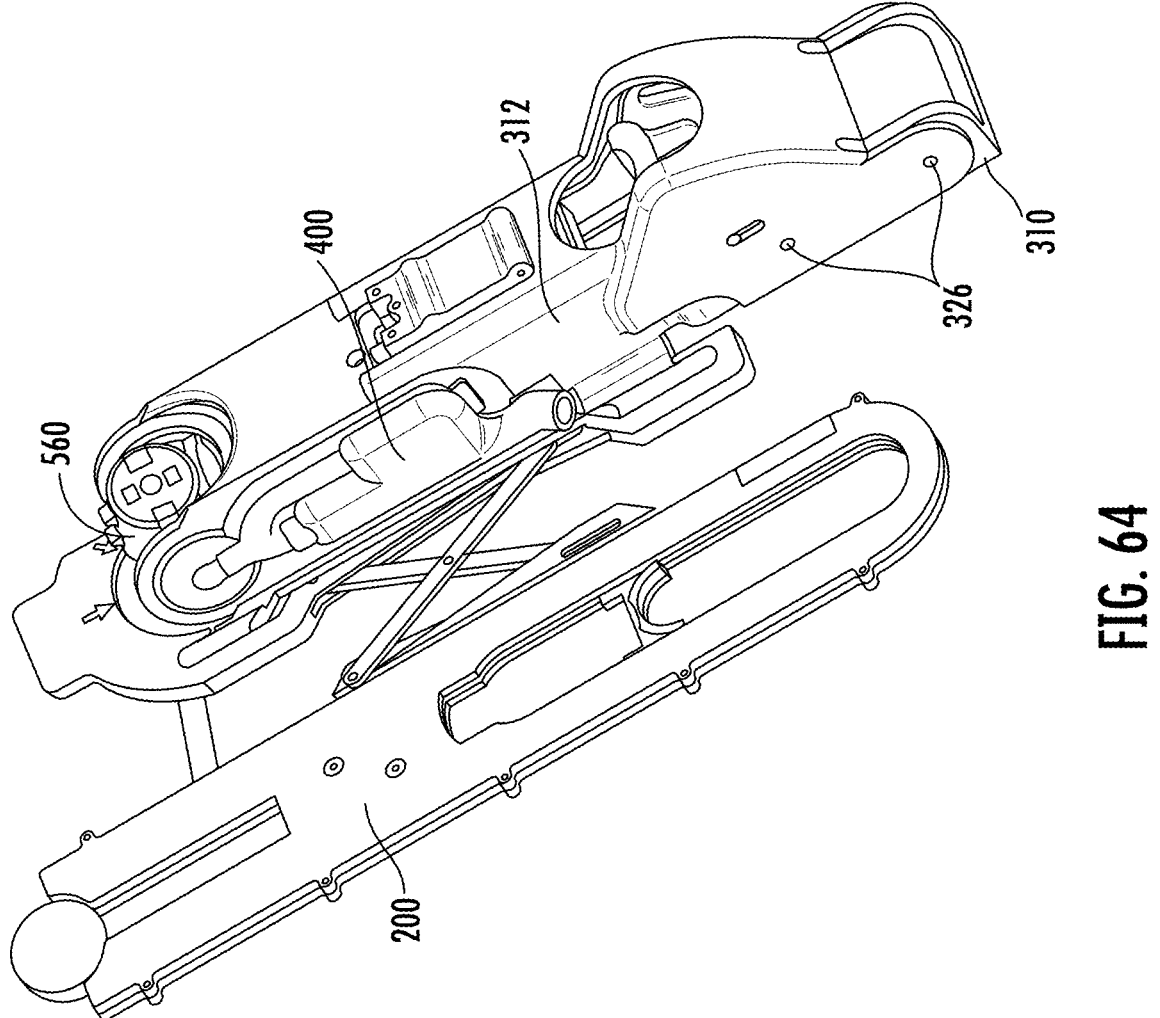
FIG. 64 is a perspective view of a needle thoracostomy device in the deployed position according to some embodiments.
Figure 65:
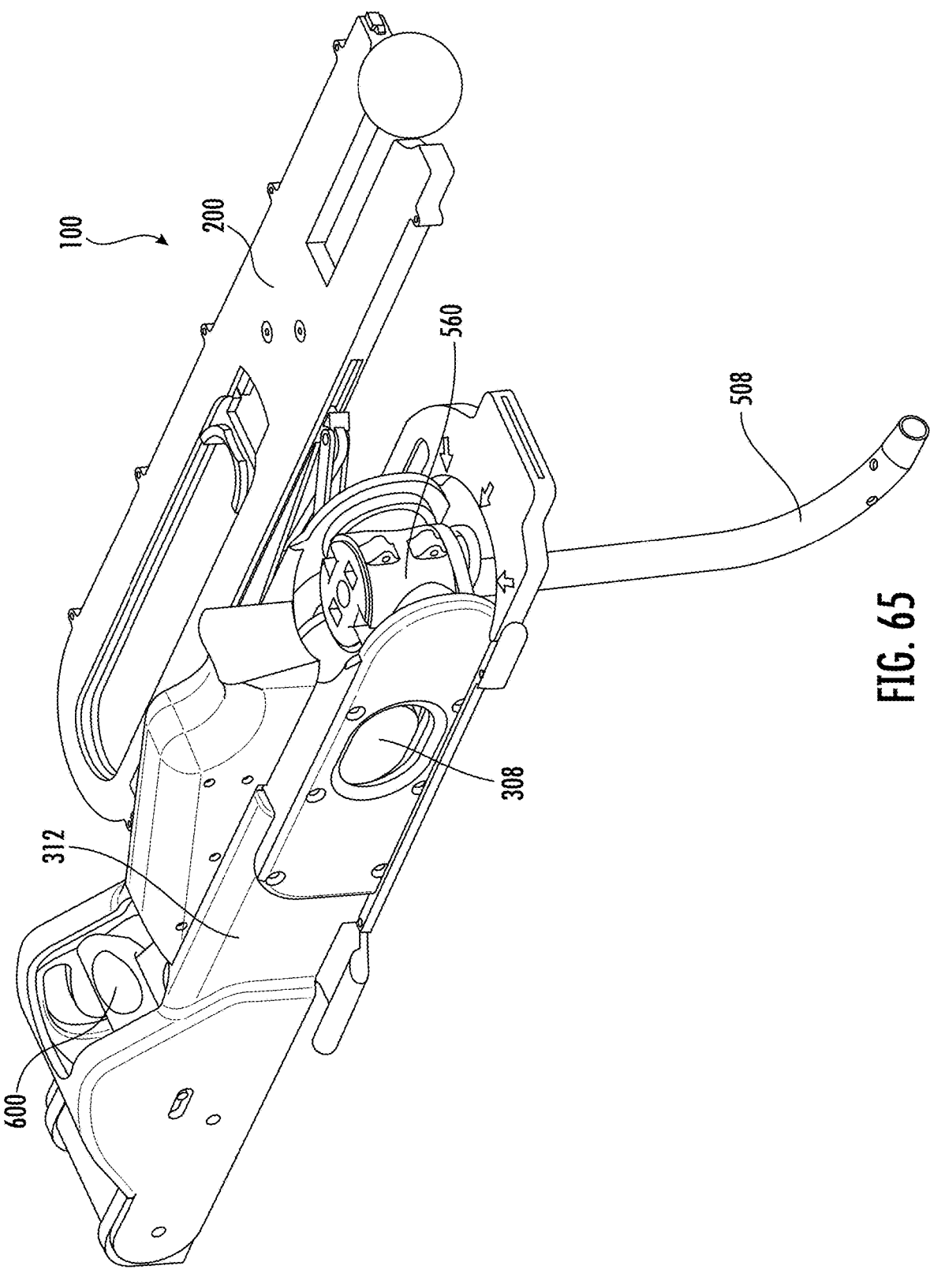
FIG. 65 is a perspective view of a needle thoracostomy device in the deployed position according to some embodiments.

Once the needle assembly 500 releases from the lever 312, the needle 506 can be removed from the patient (FIGS. 61 and 62). Additionally, the automatic release of the needle assembly 500 caused by the bias of the needle assembly 500 away from the needle thoracostomy device 100 indicates to the user that the procedure was successful when the needle assembly 500 pops out of the needle thoracostomy device. The needle thoracostomy device 100 can then continue to be moved to the deployed position, inserting the catheter 508 the rest of the way into the patient (FIGS. 63-65). At this point, there is no longer a concern that the needle thoracostomy device 100 will cause internal damage to the patient because the catheter 508 can bend and is not sharp. Once the needle thoracostomy device 100 is in the deployed position, with the lever 312 adjacent to the base 310 and the catheter 508 extending below the base 310 into the patient, the release button 308 may lock the lever 312 to the base 310 to prevent the catheter 508 from being unintentionally removed from the patient. Additionally, when in the deployed position, the needle thoracostomy device 100 is configured to have a low profile to help avoid accidental removal of the needle thoracostomy device 100 from the patient. This lateral low profile also allows for CPR to be continued if needed. The catheter 508 may be a molded pigtail catheter, which means that it is naturally curved in a way that directs the catheter 508 upward toward the patient's head. This helps to drain more air from the patient because generally the patient will be reclining, causing the air to be positioned toward the front upper area of the pleural cavity.

In some embodiments, the needle thoracostomy device 100 comprises a venting valve 402 positioned in the valve head 560 and/or adjacent the second end 316 of the lever 312, as shown in FIGS. 32, 33, 73, 74A, and 74B. The venting valve 402 is configured to remain with the needle thoracostomy device 100 upon removal of the needle assembly 500 and is configured to fluidly couple the catheter 508 to a venting device 400 once the needle assembly 500 is removed. The venting valve 402 may have a first port 404 and a second port 406 and may be configured to rotate between a needle position in which the first port 404 is aligned with the catheter 508 and a draining position in which the second port 406 is aligned with the catheter 508. The venting valve 402 may also be configured to rotate about an axis that substantially parallel with the needle 506 before the needle assembly 500 is removed. When the needle assembly 500 is installed, the needle 506 extends through the first port 404 of the venting valve 402, holding the venting valve 402 in the needle position. The venting valve 402 may be biased toward the draining position such that the venting valve 402 automatically rotates to the draining position upon removal of the needle 506 from the first port 404. Thus, the needle 506 is removable from the needle thoracostomy device 100 through the first port 404. When the needle assembly 500 is released and removed, the venting valve 402 automatically moves to the draining position, aligning the second port 406 with the catheter 508 and fluidly coupling the catheter 508 with the venting device 400, described in more detail below. When the venting valve 402 moves to the draining position, the first port 404 becomes misaligned with the catheter 508 and may therefore be sealed off from allowing any fluid to pass through the first port 404.

Figure 66:
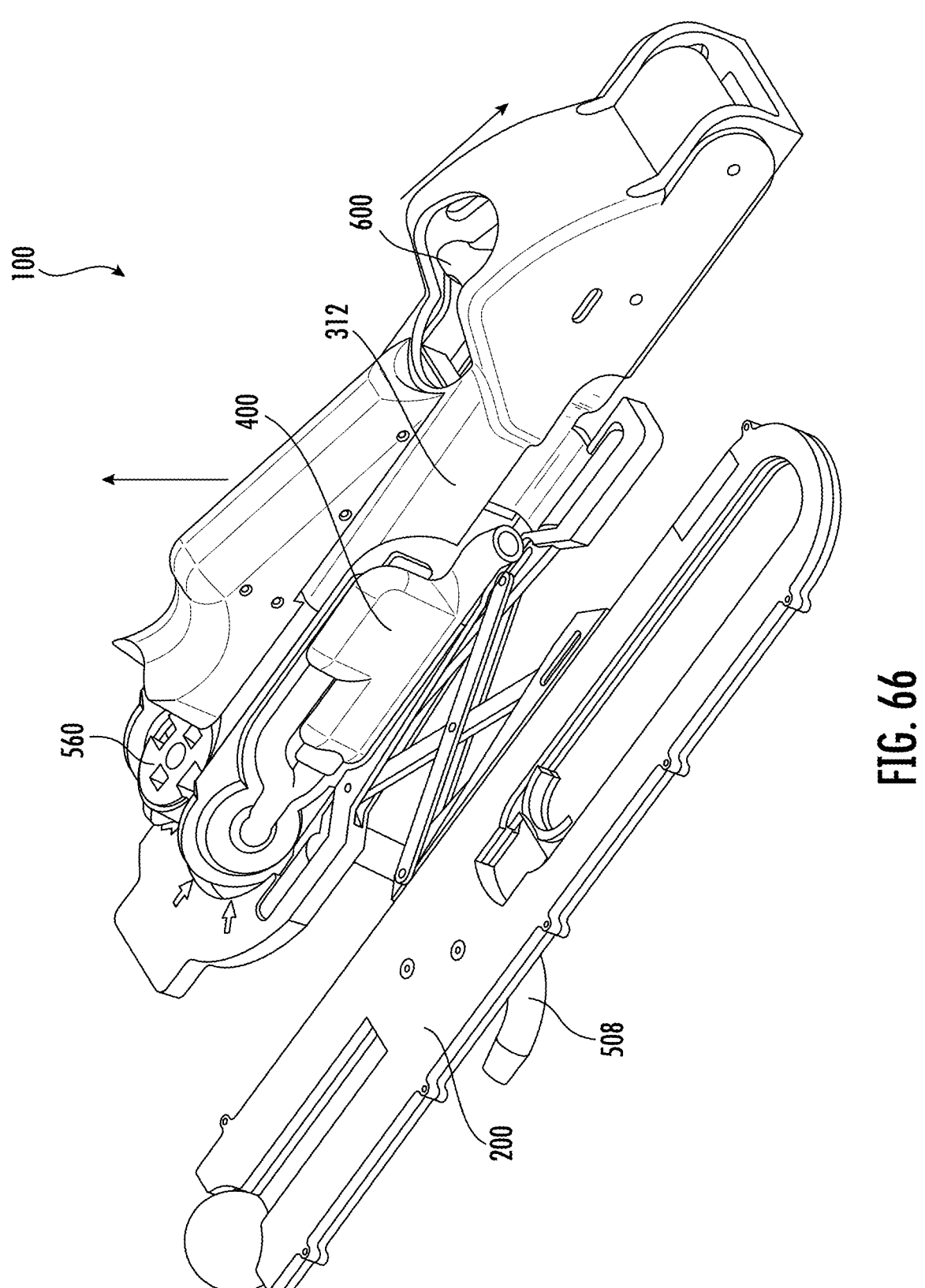
FIG. 66 is a perspective view of a needle thoracostomy device in the deployed position according to some embodiments.
Figure 67:
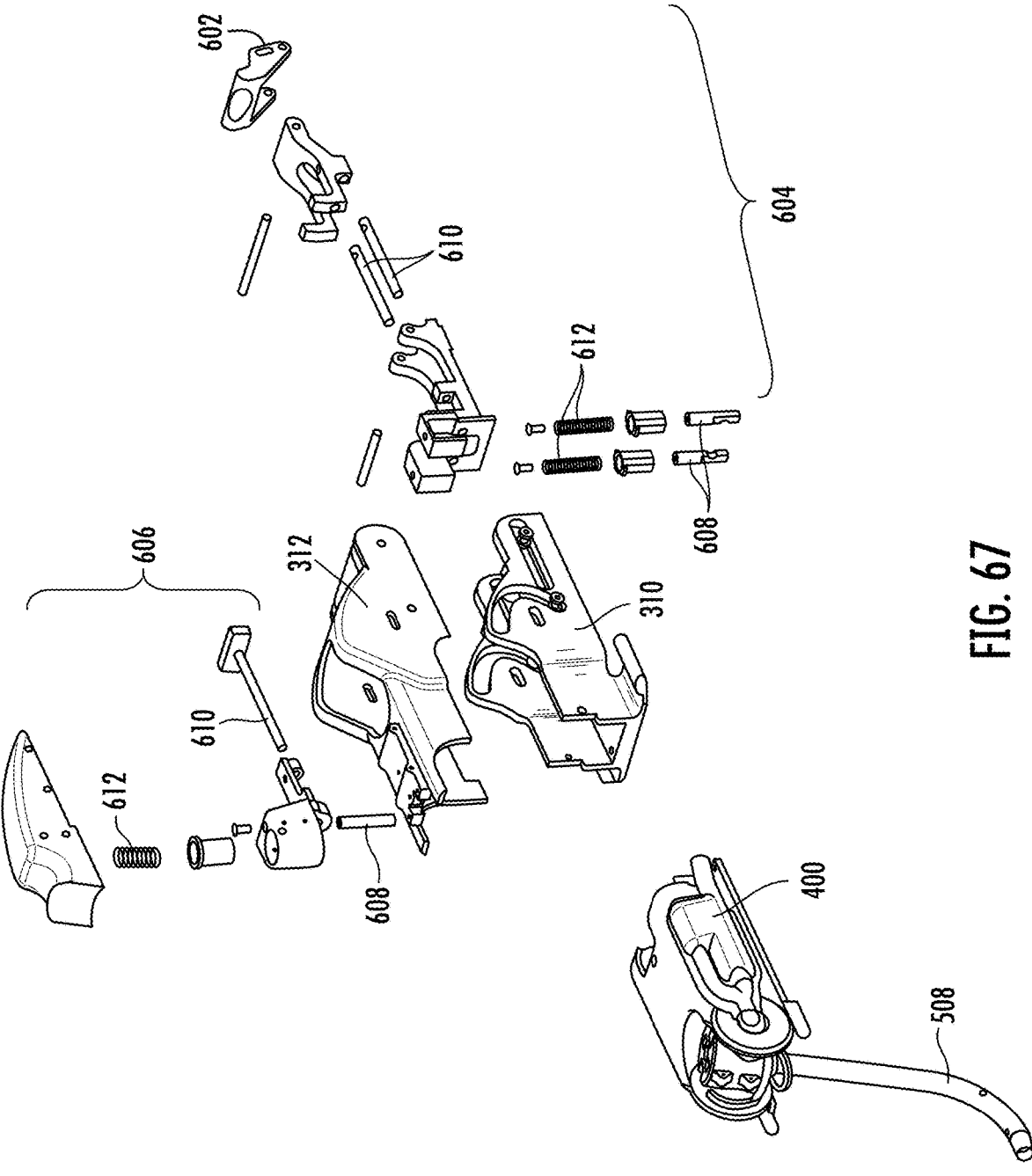
FIG. 67 is an exploded view of the release system of a needle thoracostomy device according to some embodiments.
Figure 68:
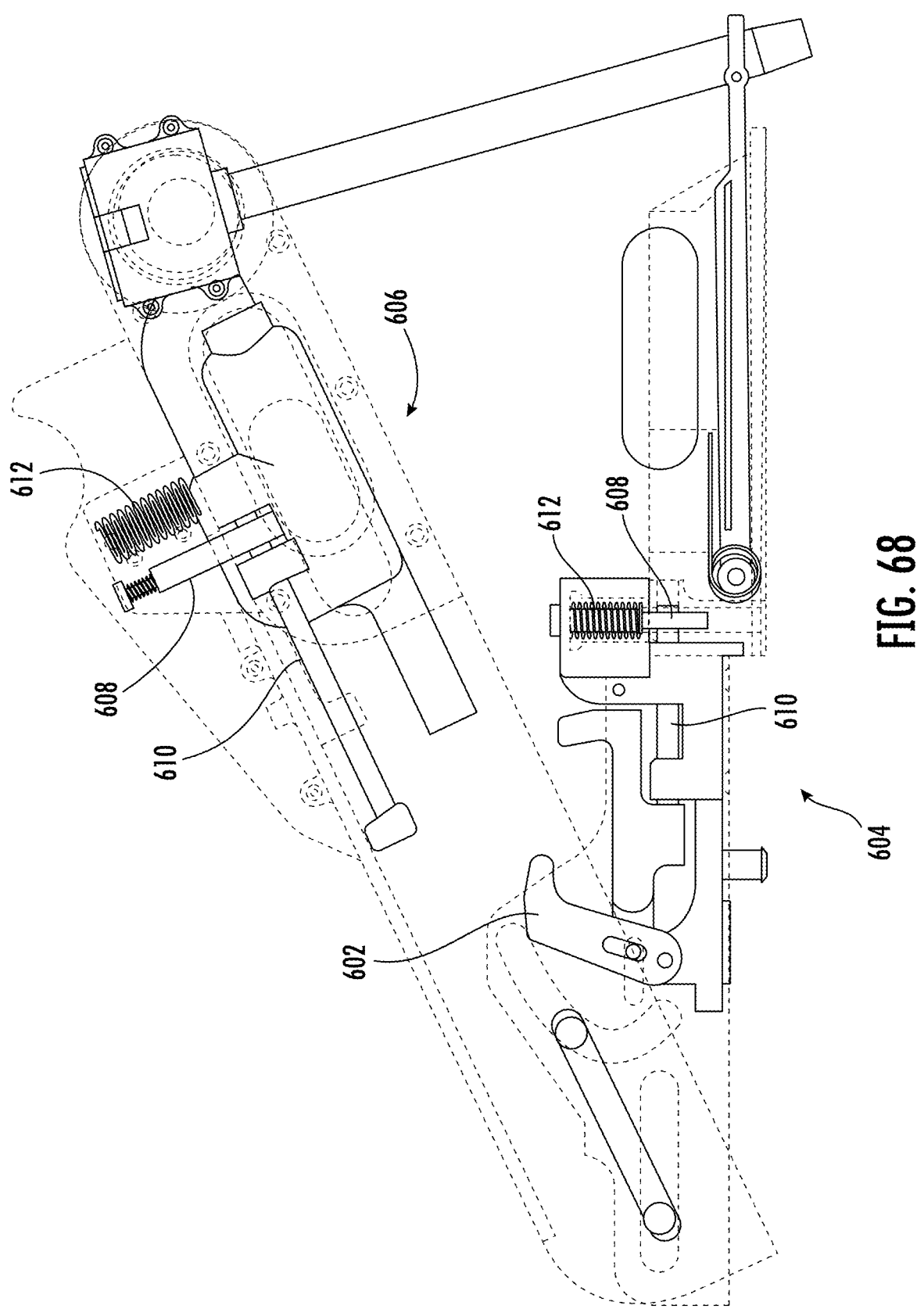
FIG. 68 is a side view of the release system of a needle thoracostomy device in between the raised position and the deployed position according to some embodiments.
Figure 69:
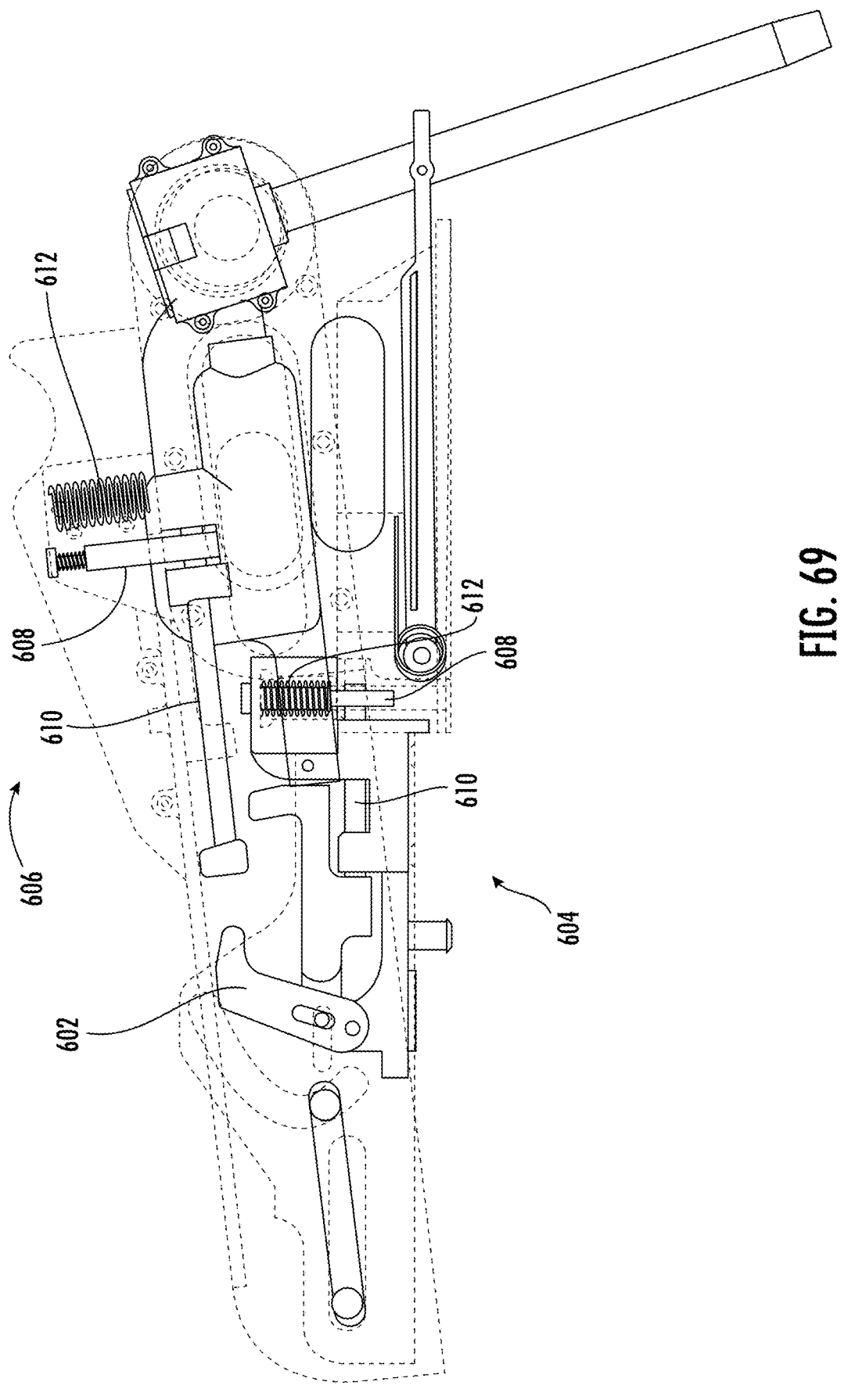
FIG. 69 is a side view of the release system of a needle thoracostomy device in between the raised position and the deployed position according to some embodiments.
Figure 70A:
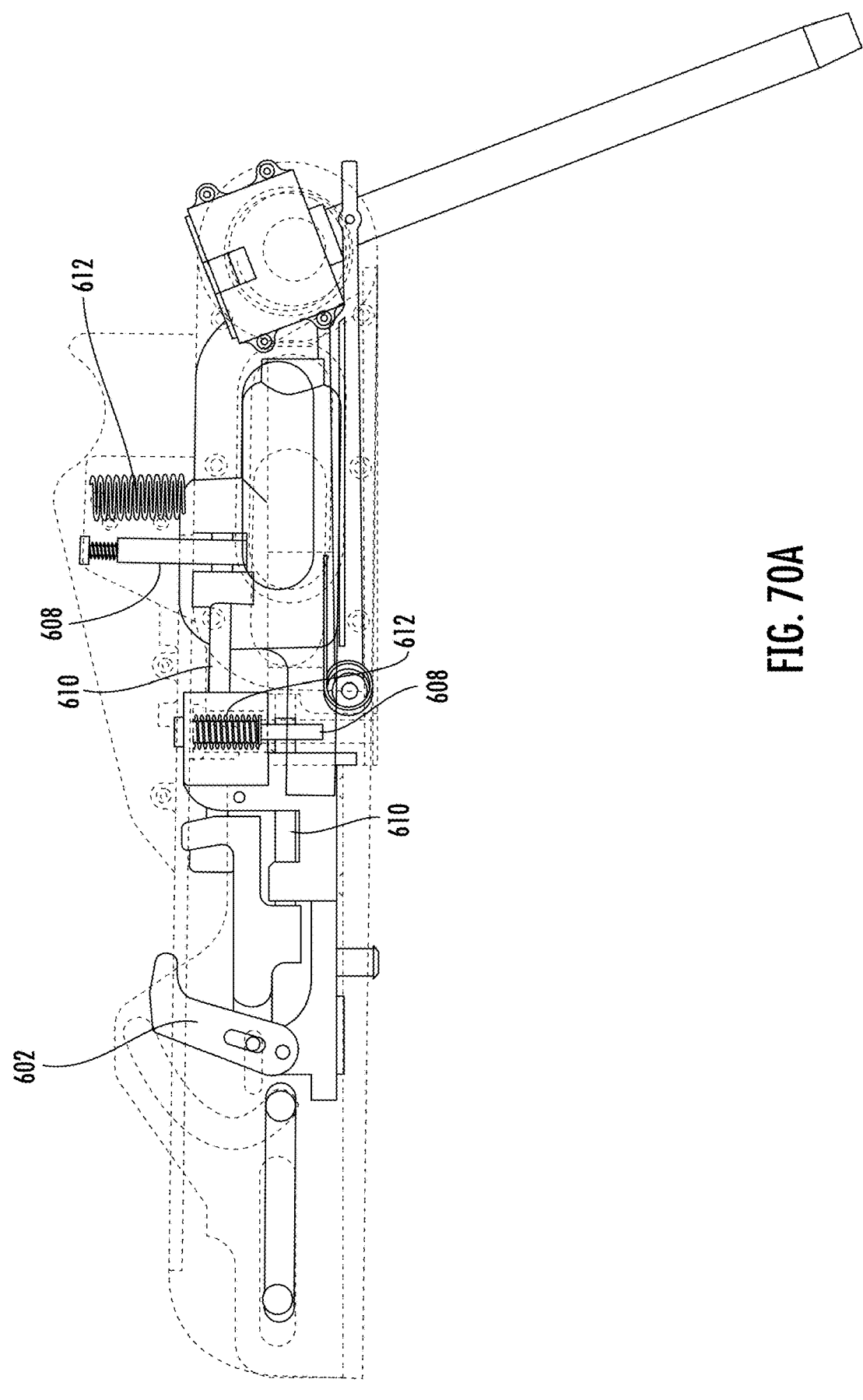
FIG. 70A is a side view of the release system of a needle thoracostomy device in the deployed position prior to engaging the release mechanism according to some embodiments.
Figure 70B:
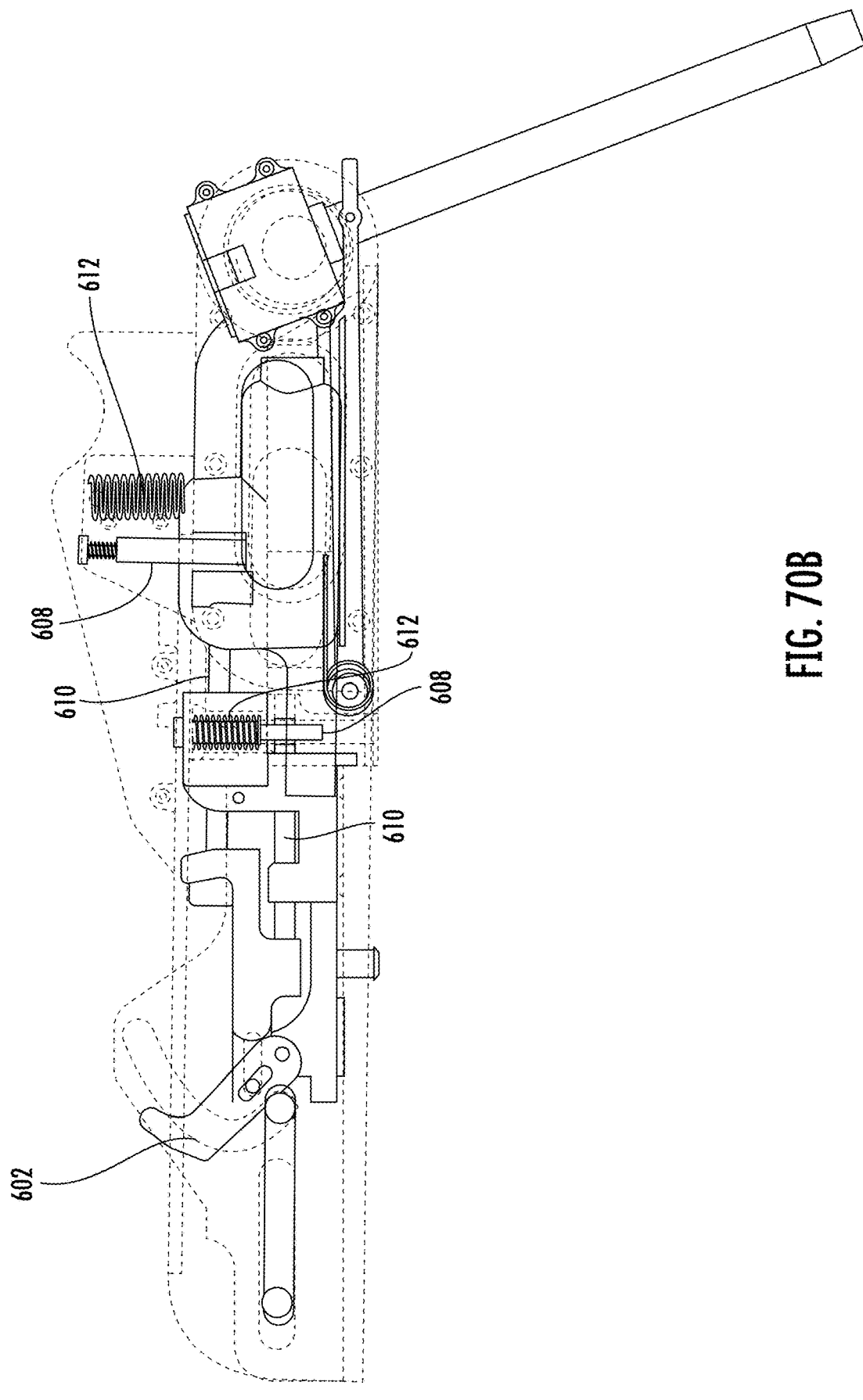
FIG. 70B is a side view of the release system of a needle thoracostomy device in the deployed position after engaging the release mechanism according to some embodiments.
Figure 72:
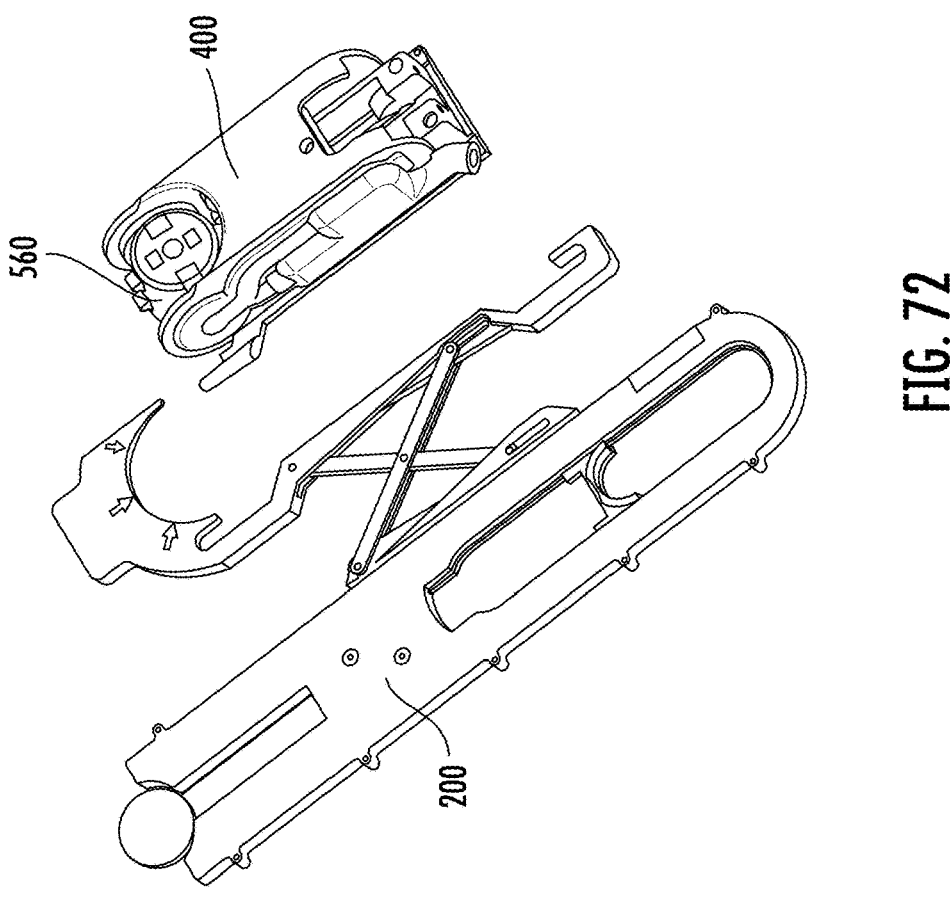
FIG. 72 is a perspective view of a venting system of a needle thoracostomy device according to some embodiments.
Figure 71:
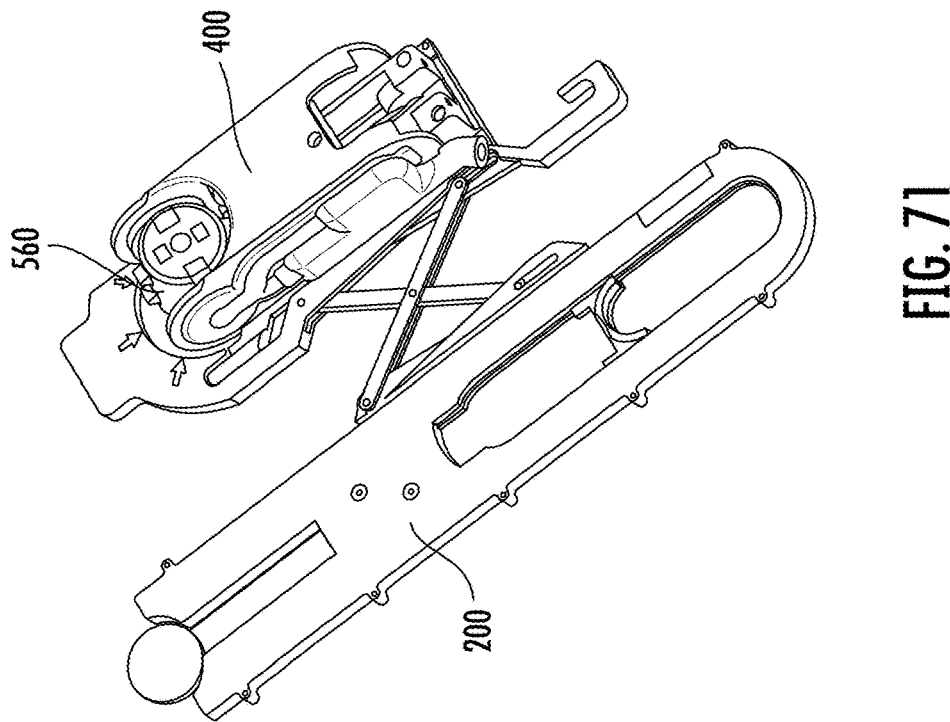
FIG. 71 is a perspective view of a venting system of a needle thoracostomy device according to some embodiments.
Figure 73:
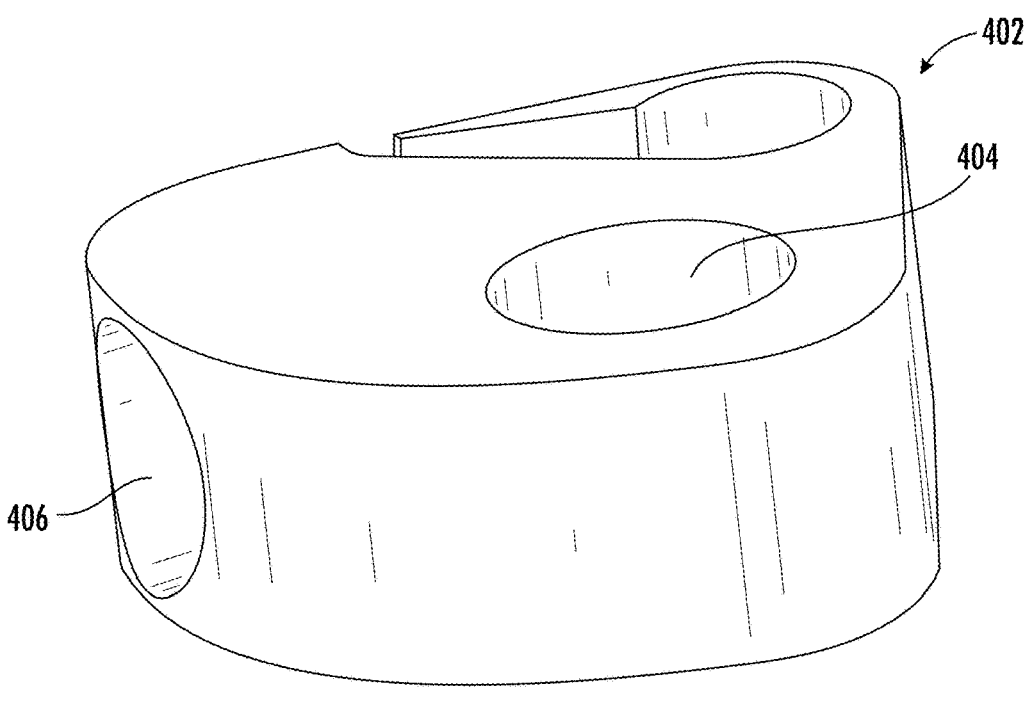
FIG. 73 is a perspective view of a venting valve of a needle thoracostomy device according to some embodiments.
Figure 74A:
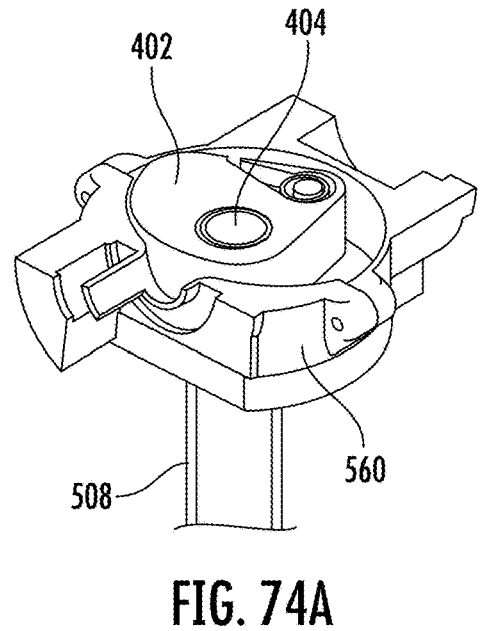
FIG. 74A is a perspective view of a venting valve of a needle thoracostomy device in the needle position according to some embodiments.
Figure 74B:
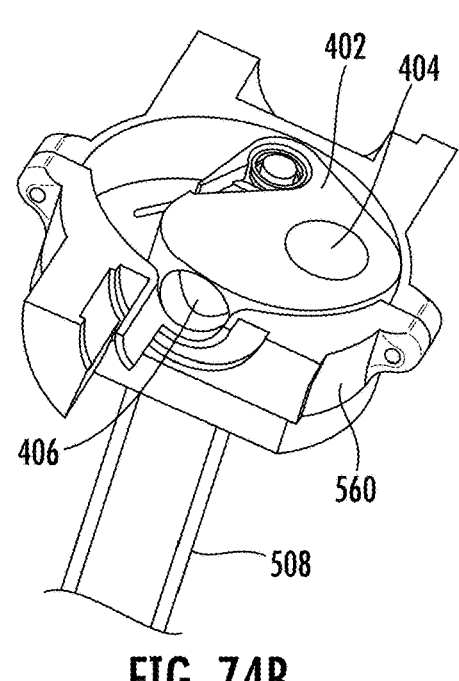
FIG. 74B is a perspective view of a venting valve of a needle thoracostomy device in a draining position according to some embodiments.

In some embodiments, the venting device 400 mentioned above is incorporated into the deployment device 300. After the needle thoracostomy device 100 is in the deployed position, the venting device 400 may be separable from the remainder of the needle thoracostomy device 100. As shown in FIGS. 66, 71, and 72, the venting device 400 may include portions from the lever 312, the base 310, and/or the needle assembly 500. The venting device 400 is separated by engaging or activating a release mechanism 600, illustrated in FIGS. 67-70B. To engage the release mechanism 600, the release mechanism 600 may be configured to move from an attached position to a released position. When the release mechanism 600 is in the attached position, the release mechanism 600 secures the deployment device 300 to the venting device 400. When the release mechanism 600 is moved to the released position, the deployment device 300 can be lifted away from the venting device 400.

The release mechanism 600 may comprise a projection 608 and a lock 610 each extending into the venting device 400. When the release mechanism 600 is in the attached position, the projection 608 and the lock 610 are mated within the venting device 400. When the release mechanism 600 is in the released position, the lock 610 is removed from the projection 608. This allows the release mechanism 600 and therefore the deployment device 300 to release the venting device 400 to separate the deployment device 300 from the venting device 400. In some embodiments, the release mechanism 600 also comprises a spring 612 aligned with the projection 608. When the release mechanism 600 is in the released position, the spring 612 is configured to bias the deployment device 300 to detach from the venting device 400 by lifting the projection 608 out of the venting device 400.

The release mechanism 600 may have a release lever 602 mechanically coupled to a first internal release mechanism 604 in the base 310. In addition, when the needle thoracostomy device 100 is in the stored position or in the deployed position, the first internal release mechanism 604 in the base 310 may be operatively linked with a second internal release mechanism 606 in the lever 312 such that the second internal release mechanism 606 interlocks with the first internal release mechanism 604. When the needle thoracostomy device 100 is in the raised position, the first internal release mechanism 604 may be disengaged from the second internal release mechanism 606. This allows the base 310 and the lever 312 to function normally without interference from the separate mechanisms of the first internal release mechanism 604 and the second internal release mechanism 606.

In some embodiments, each of the first internal release mechanism 604 and the second internal release mechanism 606 has a projection 608 and a lock 610. In some embodiments, the projection 608 extends down into the venting device 400 and the lock 610 extends horizontally into the venting device 400. The projection 608 and the lock 610 of each of the first internal release mechanism 604 and the second internal release mechanism 606 mate within the venting device 400 to lock the deployment device 300 to the venting device 400. When the release lever 602 is engaged while the needle thoracostomy device 100 is in the deployed position, the release mechanism 600 pulls the lock 610 of the first internal release mechanism 604 out of the venting device 400, thus decoupling the lock 610 of the first internal release mechanism 604 from the projection 608 of the first internal release mechanism 604. In addition, because the first internal release mechanism 604 is operatively coupled to the second internal release mechanism 606, this motion also pulls the lock 610 of the second internal release mechanism 606 out of the venting device 400, thus also decoupling the lock 610 of the second internal release mechanism 606 from the projection 608 of the second internal release mechanism 606. This frees the deployment device 300 from the venting device 400, allowing the deployment device 300 to be lifted away from the venting device 400, as shown in FIG. 66. Thus, once the needle thoracostomy has been completed, the positioning device 200 and a majority of the needle thoracostomy device 100 can be removed, leaving only the venting device 400 attached to the patient (FIG. 72) to vent the pleural cavity and prevent the pneumothorax or other conditions from recurring. This significantly reduces the size and profile of the medical equipment attached to the patient, making space for other procedures to be performed as needed, such as CPR or other procedures. In addition, the reduced size and profile decreases the risk of dislodgment of the venting device 400 due to accidental contact with the venting device 400. The suture holes 306 mentioned above may be part of the venting device 400 so that, once the deployment device 300 has been removed, the venting device 400 can still be stitched to the patient through the suture holes 306.

Figure 75:
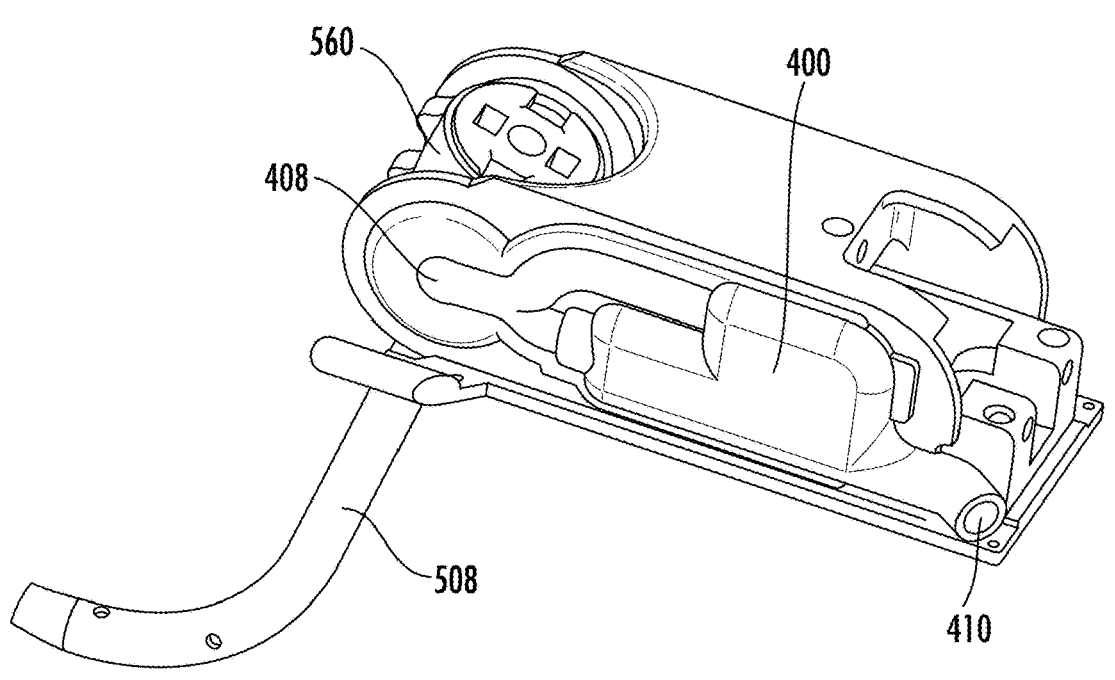
FIG. 75 is a perspective view of a venting system of a needle thoracostomy device according to some embodiments.
Figure 76:
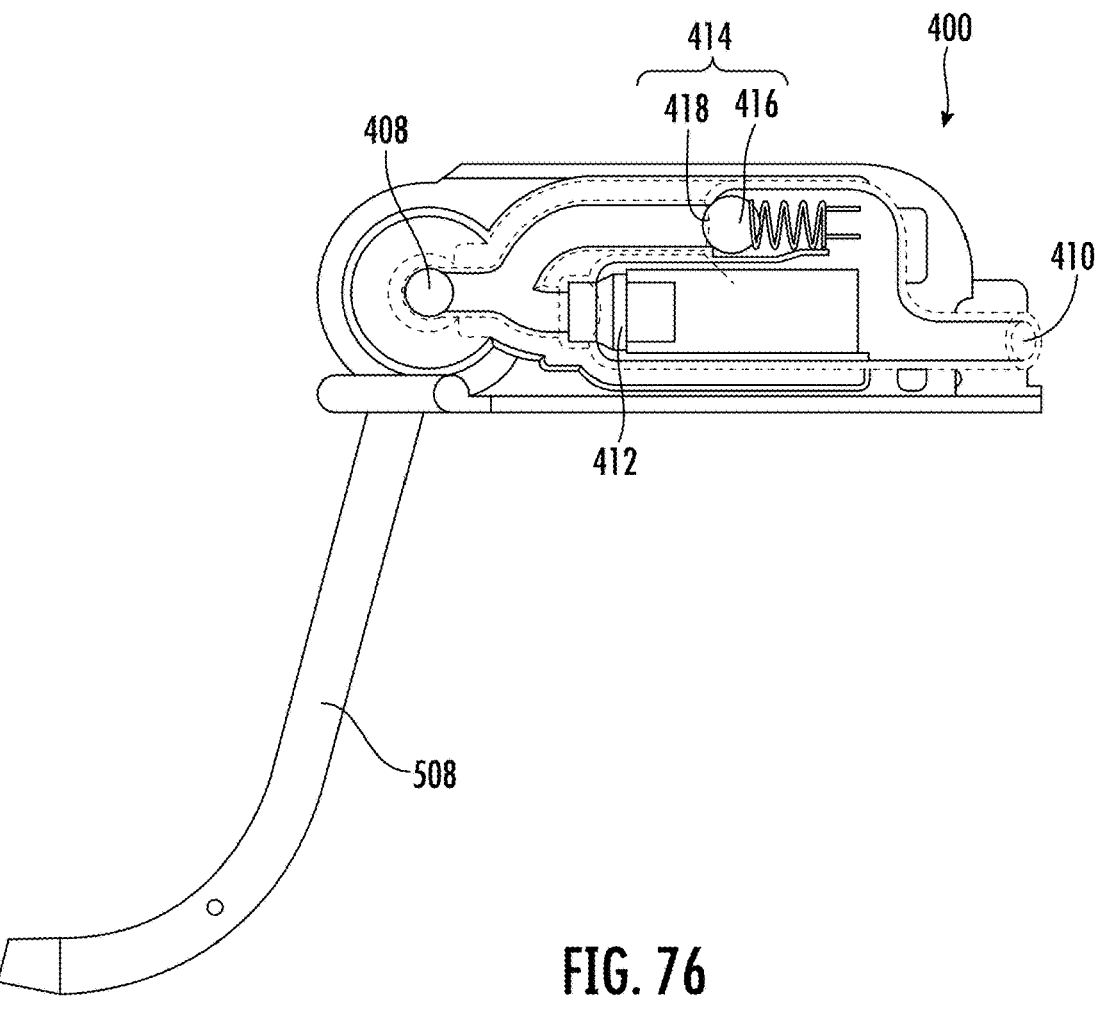
FIG. 76 is a side section view of a venting valve of a needle thoracostomy device according to some embodiments.
Figure 77:
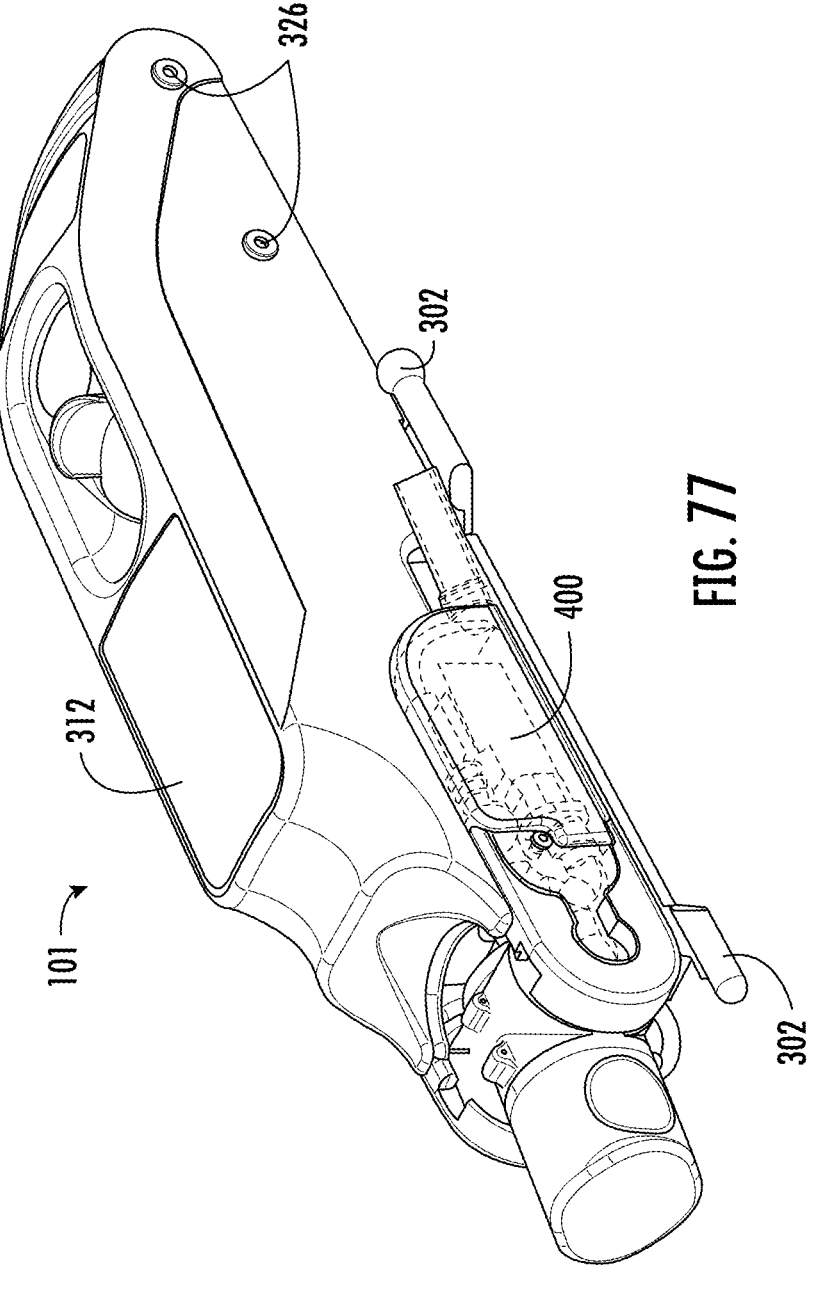
FIG. 77 is a perspective view of a needle thoracostomy device according to some embodiments.
Figure 78:
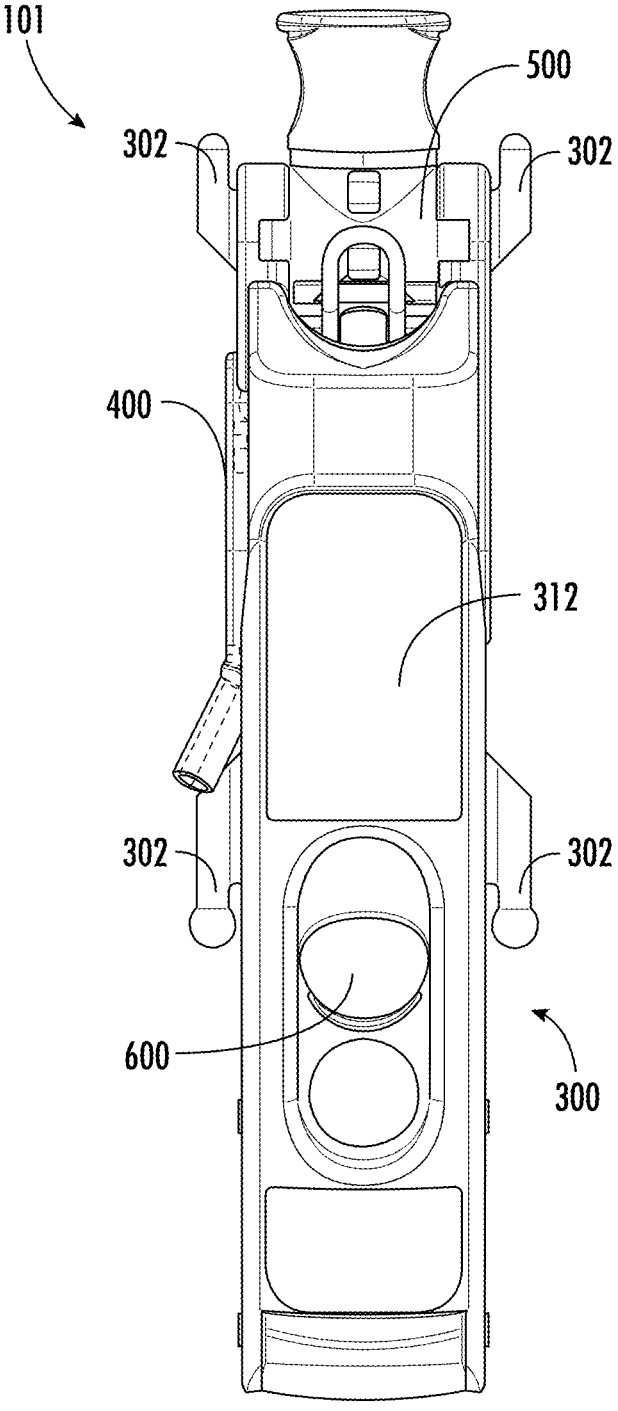
FIG. 78 is a top view of a needle thoracostomy device according to some embodiments.
Figure 79:
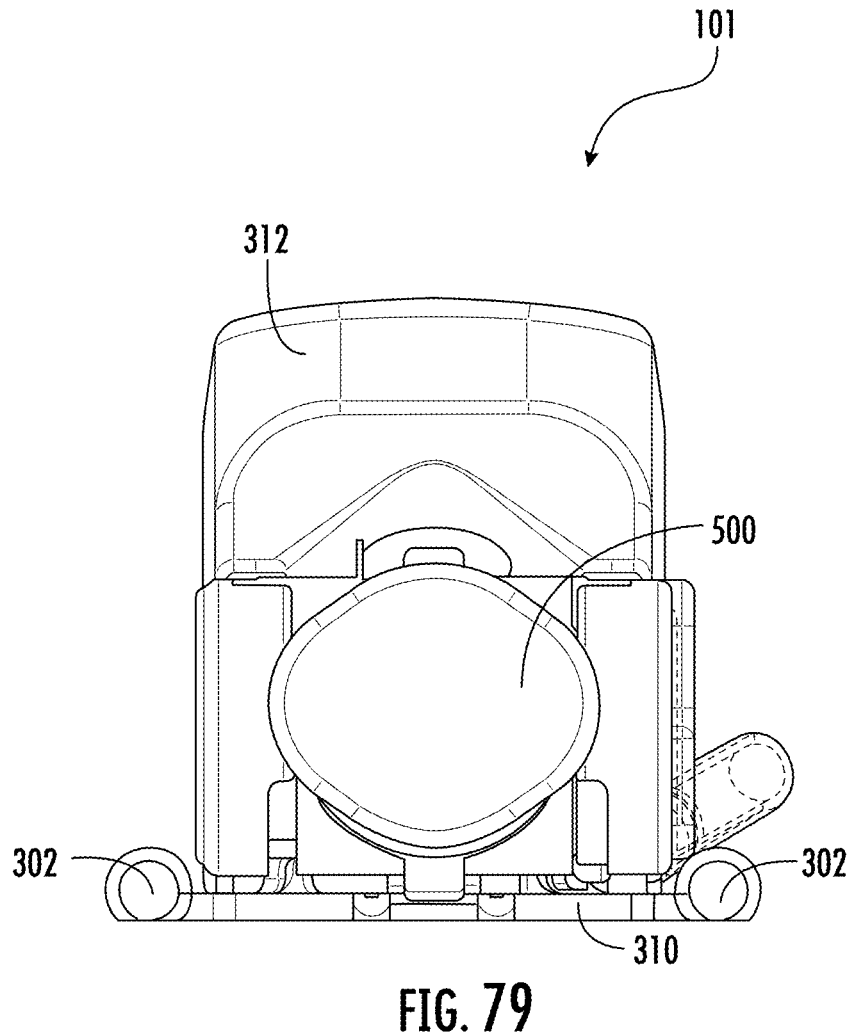
FIG. 79 is a front view of a needle thoracostomy device according to some embodiments.
Figure 80:
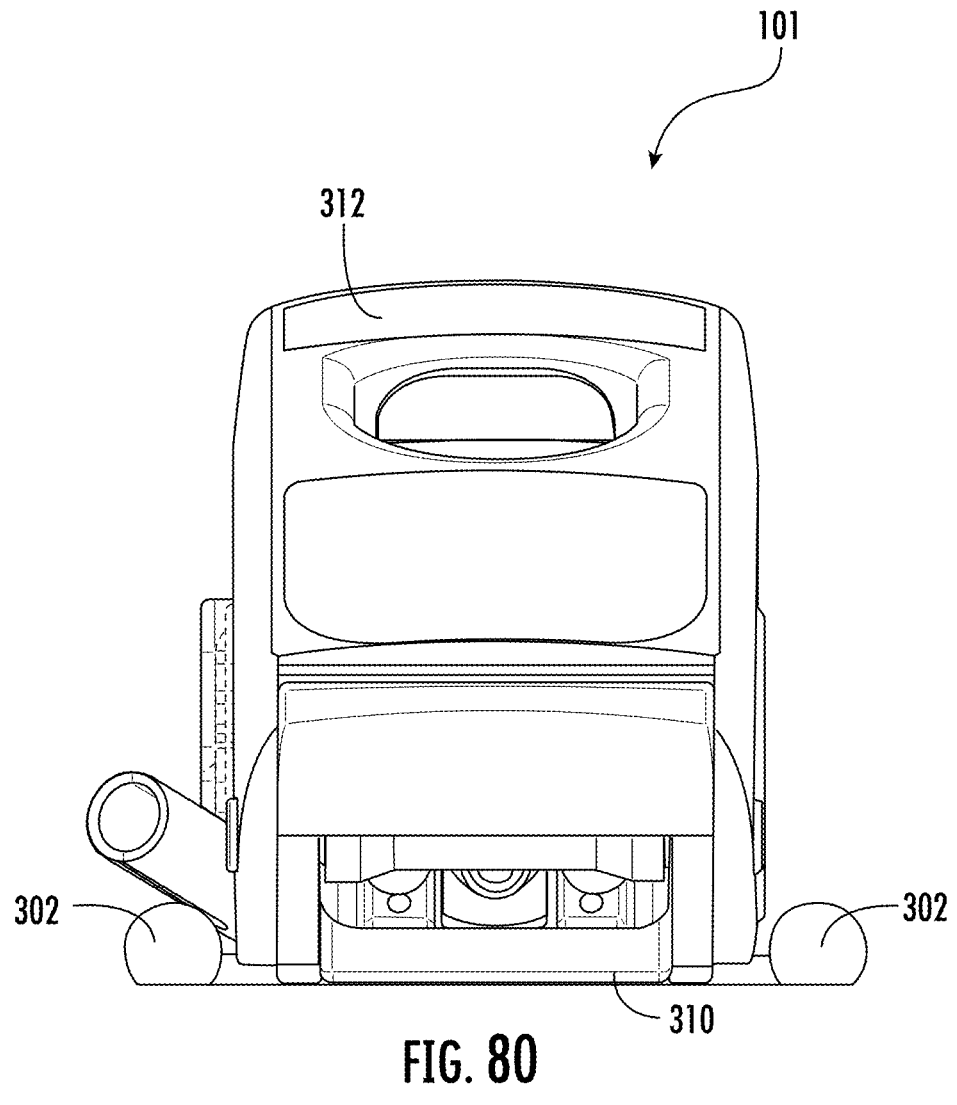
FIG. 80 is a rear view of a needle thoracostomy device according to some embodiments.
Figure 81:
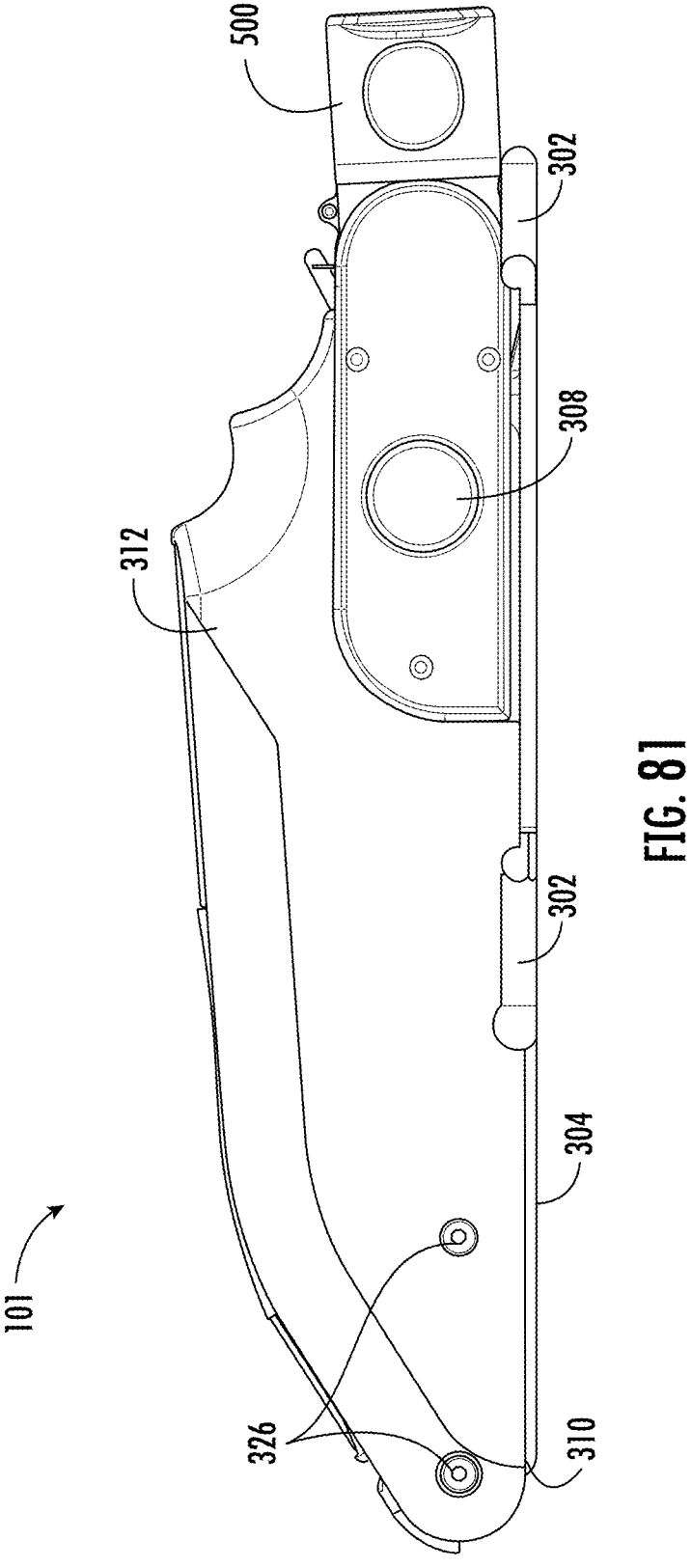
FIG. 81 is a side view of a needle thoracostomy device according to some embodiments.
Figure 82:
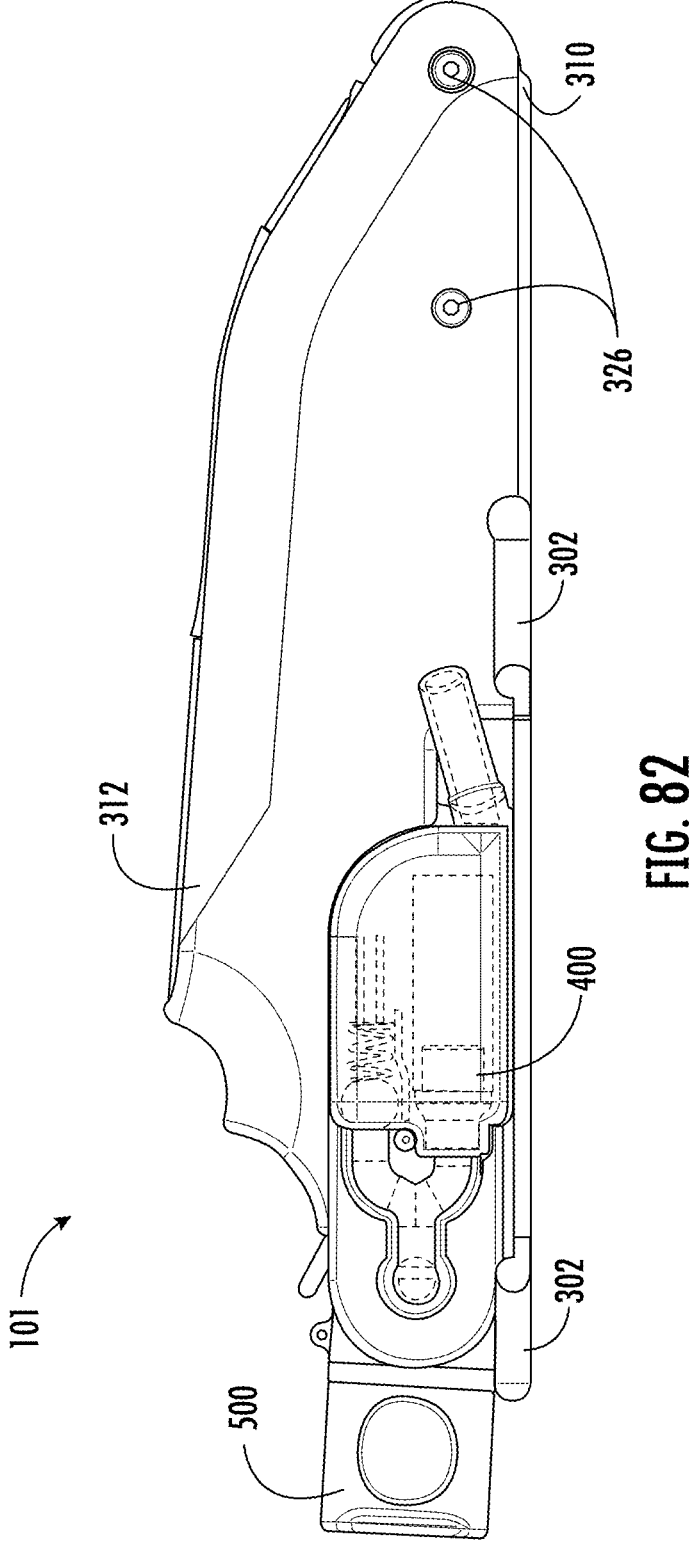
FIG. 82 is a side view of a needle thoracostomy device according to some embodiments.
Figure 83:
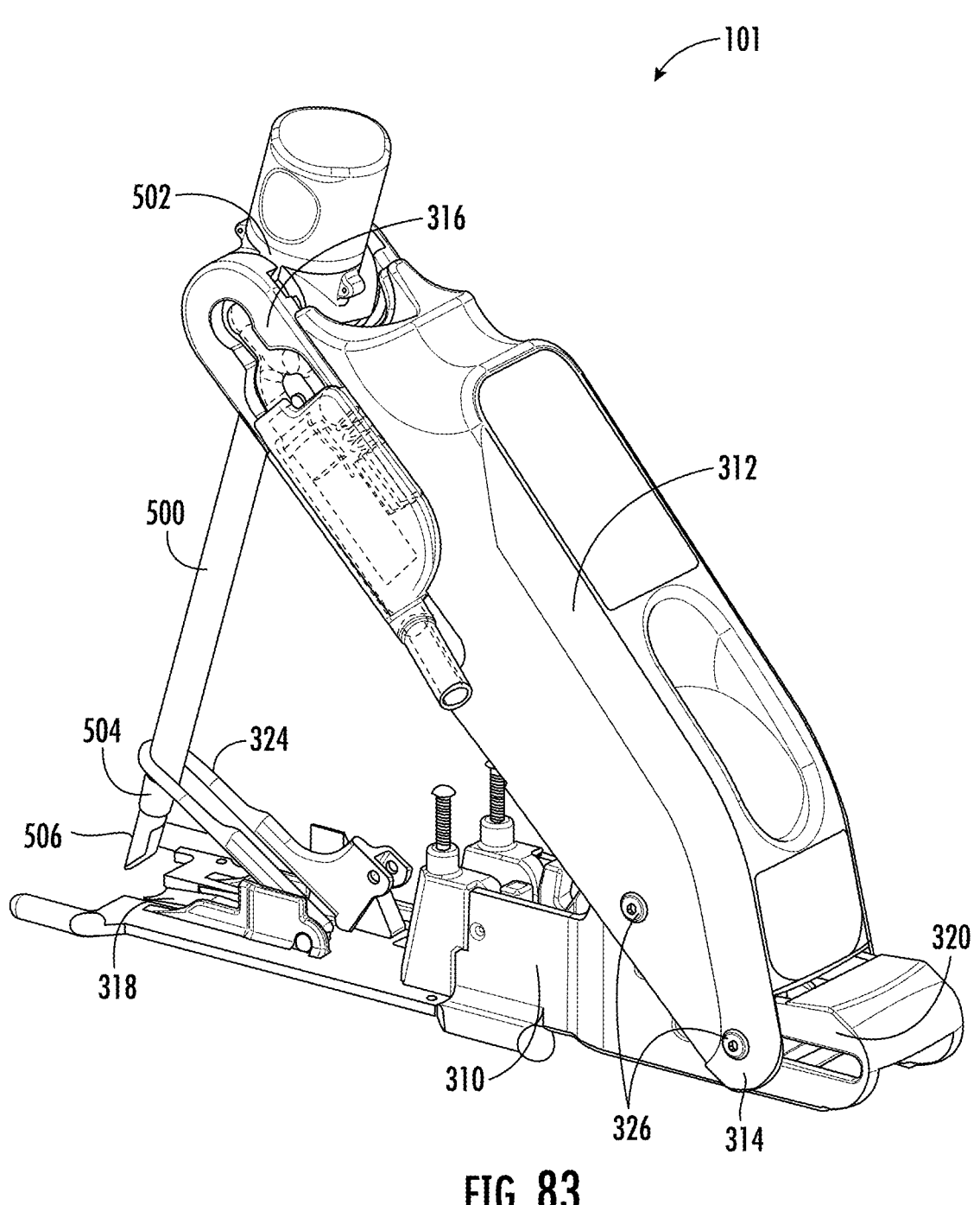
FIG. 83 is a perspective view of a needle thoracostomy device in a raised position according to some embodiments.
Figure 84:
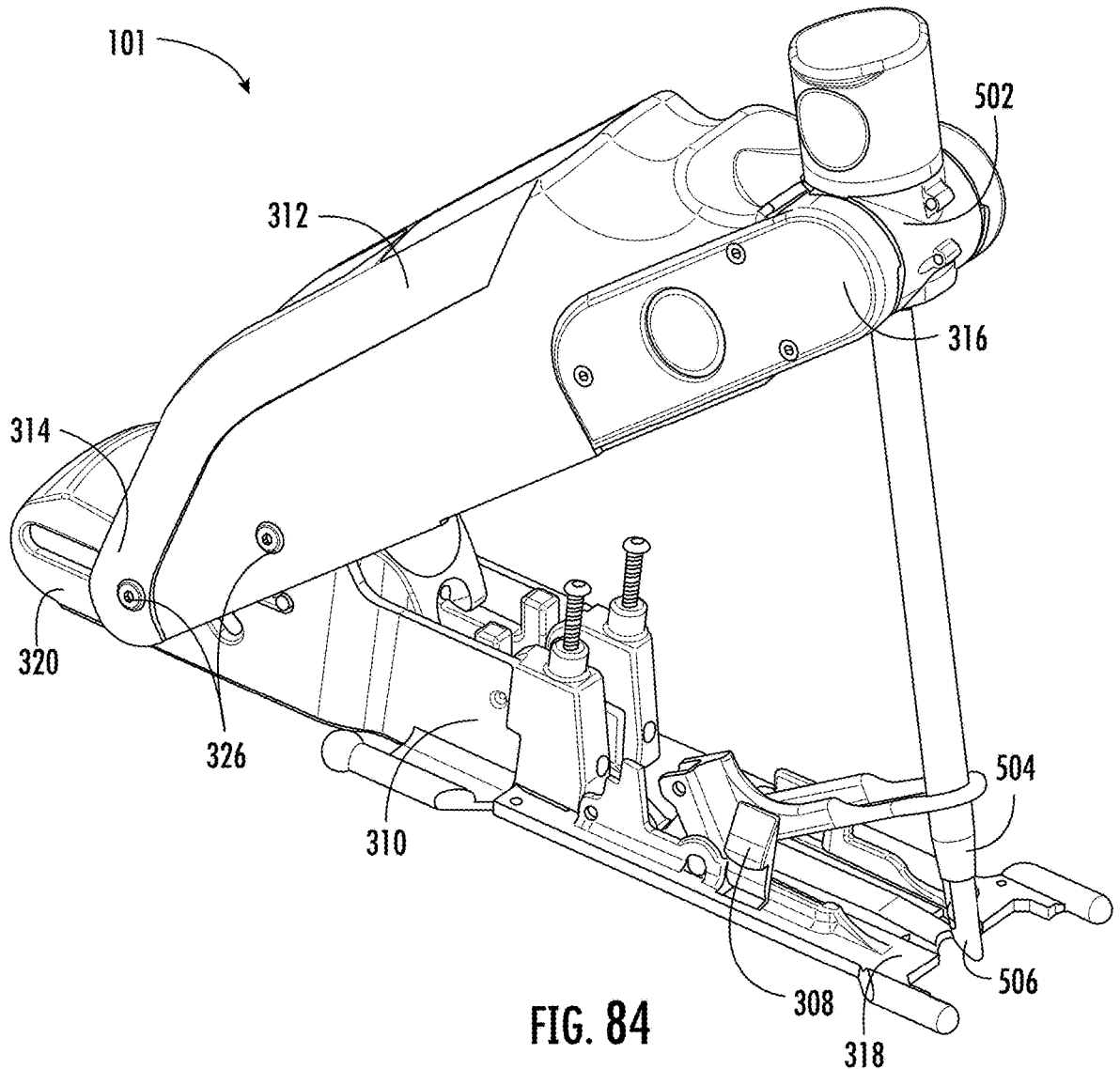
FIG. 84 is a perspective view of a needle thoracostomy device in a raised position according to some embodiments.

As described above, the venting device 400 is configured to automatically fluidly couple with the catheter 508 upon removal of the needle 506 from the needle assembly 500. As shown in FIGS. 75 and 76, in some embodiments, the venting device 400 has an inlet 408 that couples with the second port 406 of the venting valve 402, an outlet 410 that is accessible to the user and can either be connected to suction, to a drainage receptacle, and/or to open air, and a primary valve 412 positioned between the inlet 408 and the outlet 410. The primary valve 412 is configured to drain fluid, including air, from the catheter 508 to the outlet 410 and restrict fluid flow from the outlet 410 to the catheter 508. In this way, the pleural cavity can be vented without allowing outside air to travel through the catheter 508 and into the pleural cavity. The primary valve 412 may be a low-pressure valve, a low-flow valve, a Heimlich style valve, and/or a flutter style valve. In some embodiments, suction can be applied to the outlet 410 to evacuate fluid, including air, out of the pleural cavity of the patient.

As shown in FIG. 76, in some embodiments, the venting device 400 also comprises a secondary valve 414. The secondary valve 414 is configured to allow fluid from the catheter 508 to bypass the primary valve 412. The secondary valve 414 may be a high-flow valve such as a ball valve. Thus, in some embodiments, the needle thoracostomy device 100 is configured with multiple paths for fluid drainage. This is particularly useful for situations where the venting device 400 is used for longer periods of time because the primary valve 412 may clog due to fluid clotting. The secondary valve 414 is helpful to allow bypass of the primary valve 412 and any clotting there. In some embodiments, to allow flow through the secondary valve 414, suction may be applied to the outlet 410 to pull the ball 416 of the secondary valve 414 off the valve seat 418 of the secondary valve 414 to allow fluid to bypass the clogged primary valve 412. The primary valve 412 and the secondary valve 414 may make use of the same inlet 408 from the catheter 508 and the same outlet 410 from the venting device 400. The venting device 400 may also have a viewing window to allow a user to see if there is flow, when there is no flow, and when the secondary valve 414 opens.

The venting device 400 as described avoids the use of tubing in the venting device 400 itself. This is an improvement over current technology because tubing tends to get pinched and kinked. Additionally, the motion of the lever 312 with respect to the base 310 and the motion of the needle assembly 500 with respect to the lever 312 described above would be much more complicated if tubing were included in the needle thoracostomy device 100.

The needle thoracostomy device 100 is configured to fit into a small container and be highly portable. For example, it is sized to easily fit into the Individual First Aid Kit (IFAK) of a military member. In some embodiments, the needle thoracostomy device 100 is configured for use by military personnel. For example, the needle thoracostomy device 100 may be visible while using military night vision or thermal vision devices to allow the device to be useful in a variety of circumstances, such as when visibility is low. As described in detail above, when the needle thoracostomy device 100 is in the stored position, the needle thoracostomy device is compact. In addition, the venting device 400 is compact. This makes the needle thoracostomy device 100 easy to carry on the body prior to use and keeps a low profile on the body after the needle thoracostomy has been performed. This is important for uses when the patient must be transported quickly with sometimes rough, rapid movement, such as may occur during military operations.

The needle thoracostomy device 100 is a safety device that is designed to increase the confidence of the user and improve the success rate of needle thoracostomies. As described above, the needle thoracostomy device 100 protects against penetrating into the patient too far, ejects the needle 506 once the desired depth is reached, provides protection to the lungs of the patient with the plunger 516, and increases the safety of the procedure by providing a positioning device 200 that correctly positions the deployment device 300 such that arteries and vasculature are avoided. The success rate is improved by improving the positioning of the procedure and the depth of the procedure, and by allowing for larger catheters that have incisions cut to the correct size.

Based on the needle thoracostomy device 100 described above, the present disclosure is also related to a method of performing a needle thoracostomy. This method may comprise positioning a needle thoracostomy device 100 on a patient, moving the needle thoracostomy device 100 from a stored position to a raised position, setting the needle assembly 500 at a desired angle, and lowering the needle thoracostomy device 100 from the raised position to a deployed position. The desired angle may be oblique with respect to the base 310 of the needle thoracostomy device 100. Lowering the needle thoracostomy device 100 from the raised position to the deployed position may comprise inserting a needle 506 and a catheter 508 into a pleural cavity of the patient. The method may also comprise maintaining the needle assembly 500 at the desired angle while lowering the needle thoracostomy device 100 from the raised position to the deployed position, detaching the needle assembly 500 from the needle thoracostomy device 100, and removing the needle 506 from the patient. The method may also comprise moving the needle assembly 500 along an axis 510 of the needle 506 while lowering the needle thoracostomy device 100 from the raised position to the deployed position, determining when the needle 506 reaches the pleural cavity and automatically detaching the needle assembly 500 from the needle thoracostomy device 100 in response to the needle reaching the pleural cavity, and/or automatically fluidly coupling the catheter 508 to the venting device 400 in response to removing the needle 506 from the patient.

The present disclosure is also related to a method of performing a needle thoracostomy that comprises positioning the needle thoracostomy device 100 on a patient, moving the needle thoracostomy device 100 from the stored position to the raised position, lowering the needle thoracostomy device 100 from the raised position to the deployed position, moving the needle assembly 500 along the axis 510 of the needle 506 while lowering the needle thoracostomy device 100 from the raised position to the deployed position, detaching the needle assembly 500 from the needle thoracostomy device 100 and removing the needle 506 from the patient. The method may further comprise determining when the needle 506 reaches the pleural cavity and automatically detaching the needle assembly 500 from the needle thoracostomy device 100 in response to the needle 506 reaching the pleural cavity and/or automatically fluidly coupling the catheter 508 to the venting device 400 in response to removing the needle 506 from the patient.

The present disclosure is also related to a method of performing a needle thoracostomy that comprises positioning the needle thoracostomy device 100 on the patient, moving the needle thoracostomy device 100 from the stored position to the raised position, lowering the needle thoracostomy device 100 from the raised position to the deployed position, determining when the needle 506 reaches the pleural cavity, automatically detaching the needle assembly 500 from the needle thoracostomy device 100 in response to the needle 506 reaching the pleural cavity, and removing the needle 506 from the patient. In some embodiments, determining when the needle 506 reaches the pleural cavity comprises simultaneously inserting the needle 506 into the patient past a minimum depth and sensing decreased resistance to penetration by the needle 506.

The present disclosure is also related to a method of performing a needle thoracostomy that comprises positioning a needle thoracostomy device 100 on a patient, inserting the needle 506 and the catheter 508 into a pleural cavity of the patient, detaching the needle assembly 500 from the needle thoracostomy device 100, removing the needle 506 from the patient, and automatically fluidly coupling the catheter 508 to the venting device 400 in response to removing the needle 506 from the patient.

The present disclosure is related to a method of performing a needle thoracostomy that comprises providing a positioning device 200, a deployment device 300, and a venting device 400 attached to the deployment device 300. The positioning device 200 may be used to determine an optimal position on the patient for the deployment device 300. The deployment device 300 may be attached to the positioning device 200, the deployment device 300 may be positioned in the optimal position. A catheter 508 of the venting device 400 may be inserted into the patient using the deployment device 300. The venting device 400 may be attached to the patient. The positioning device 200 and the deployment device 300 may be removed from the patient while leaving the venting device 400 on the patient.

Attaching the venting device 400 to the patient may comprise suturing the venting device 400 to the patient or may comprise attaching the venting device 400 to the patient with adhesive. Attaching the deployment device 300 to the positioning device 200 may comprise inserting a docking prong 302 on at least one of the deployment device 300 and the venting device 400 into a docking port 236 on the positioning device 200. The method may comprise detaching the venting device 400 from the deployment device 300. Detaching the venting device 400 from the deployment device 300 may comprise moving the release mechanism 600 to a released position. Moving the release mechanism 600 to the released position may comprise removing the lock 610 from the projection 608. The method may further comprise automatically lifting the deployment device 300 away from the venting device 400 in response to moving the release mechanism 600 to the released position.

The present disclosure is also related to a method of performing a needle thoracostomy that comprises providing a positioning device 200 and a deployment device 300, using the positioning device 200 to determine an optimal position on the patient for the deployment device 300, attaching the deployment device 300 to the positioning device 200, positioning the deployment device 300 in the optimal position, and inserting a catheter 508 into the patient using the deployment device 300. Attaching the deployment device 300 to the positioning device 200 may comprise inserting a docking prong 302 on the deployment device 300 into a docking port 236 on the positioning device 200.

The present disclosure may also comprise a method of performing a needle thoracostomy that comprises providing a deployment device 300 and a venting device 400 attached to the deployment device 300, positioning the deployment device 300 and the venting device 400 on the patient, inserting a catheter 508 of the venting device 400 into the patient using the deployment device 300, attaching the venting device 400 to the patient, and removing the deployment device 300 from the patient while leaving the venting device 400 on the patient. Attaching the venting device 400 to the patient may comprise suturing the venting device 400 to the patient and/or attaching the venting device 400 to the patient with adhesive. The method may also comprise detaching the venting device 400 from the deployment device 300. Detaching the venting device 400 from the deployment device 300 may comprise moving a release mechanism 600 to a released position. Moving the release mechanism 600 to the released position may comprise removing a lock 610 of the release mechanism 600 from a projection 608 of the release mechanism 600. The method may also comprise automatically lifting the deployment device 300 away from the venting device 400 in response to moving the release mechanism 600 to the released position.

It is to be understood that any of the methods disclosed above may be modified to include steps disclosed with reference to other methods disclosed above. A person of skill in the art will understand how these different steps may be combined to perform a needle thoracostomy with successful results.

Many additional implementations are possible. Further implementations are within the CLAIMS.

It will be understood that implementations of the needle thoracostomy device include but are not limited to the specific components disclosed herein, as virtually any components consistent with the intended operation of various needle thoracostomy devices may be utilized. Accordingly, for example, it should be understood that, while the drawings and accompanying text show and describe particular needle thoracostomy device implementations, any such implementation may comprise any shape, size, style, type, model, version, class, grade, measurement, concentration, material, weight, quantity, and/or the like consistent with the intended operation of needle thoracostomy devices.

The concepts disclosed herein are not limited to the specific needle thoracostomy device shown herein. For example, it is specifically contemplated that the components included in particular needle thoracostomy devices may be formed of any of many different types of materials or combinations that can readily be formed into shaped objects and that are consistent with the intended operation of the needle thoracostomy device. For example, the components may be formed of: rubbers (synthetic and/or natural) and/or other like materials; glasses (such as fiberglass), carbon-fiber, aramid-fiber, any combination therefore, and/or other like materials; elastomers and/or other like materials; polymers such as thermoplastics (such as ABS, fluoropolymers, polyacetal, polyamide, polycarbonate, polyethylene, polysulfone, and/or the like, thermosets (such as epoxy, phenolic resin, polyimide, polyurethane, and/or the like), and/or other like materials; plastics and/or other like materials; composites and/or other like materials; metals, such as zinc, magnesium, titanium, copper, iron, steel, carbon steel, alloy steel, tool steel, stainless steel, spring steel, aluminum, and/or other like materials; and/or any combination of the foregoing.

Furthermore, needle thoracostomy devices may be manufactured separately and then assembled together, or any or all of the components may be manufactured simultaneously and integrally joined with one another. Manufacture of these components separately or simultaneously, as understood by those of ordinary skill in the art, may involve 3-D printing, extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled or removably coupled with one another in any manner, such as with adhesive, a weld, a fastener, any combination thereof, and/or the like for example, depending on, among other considerations, the particular material(s) forming the components.

In places where the description above refers to particular needle thoracostomy device implementations, it should be readily apparent that a number of modifications may be made without departing from the spirit thereof and that these implementations may be applied to other implementations disclosed or undisclosed. The presently disclosed needle thoracostomy devices are, therefore, to be considered in all respects as illustrative and not restrictive.

We claim:

1. A needle thoracostomy device, comprising:
a base having a first end and a second end;
a lever having a first end and a second end, wherein the first end of the lever is hingedly coupled to the second end of the base; and
a needle assembly hingedly coupled to the second end of the lever and having a needle and a catheter, wherein the needle thoracostomy device is moveable between a stored position in which the lever and the needle assembly are adjacent the base, a raised position in which the lever is positioned at an oblique angle with respect to the base and the needle assembly extends between the lever and the base, and a deployed position in which the lever is adjacent the base and the needle assembly extends below the base;
wherein a hinge joining the lever to the base is configured to allow rotation and linear motion of the lever with respect to the base but constrain both the rotation and the linear motion such that the needle assembly moves along an axis of the needle as the needle thoracostomy device moves from the raised position to the deployed position.

2. The needle thoracostomy device of claim 1, further comprising a venting system having an outlet and a primary valve configured to drain fluid from the catheter to the outlet and restrict fluid flow from the outlet to the catheter.

3. The needle thoracostomy device of claim 2, wherein the venting system comprises a secondary valve configured to allow fluid from the catheter to bypass the primary valve.

4. The needle thoracostomy device of claim 1, further comprising a venting valve positioned adjacent the second end of the lever, the venting valve having a first port and a second port, wherein the venting valve is configured to rotate between a needle position in which the first port is aligned with the catheter and a draining position in which the second port is aligned with the catheter, wherein the venting valve is configured to fluidly couple the catheter to a venting system when in the draining position.

5. The needle thoracostomy device of claim 4, wherein the needle is removable from the needle assembly through the first port and wherein the venting valve is biased toward the draining position such that the venting valve automatically rotates to the draining position upon removal of the needle from the first port.

6. The needle thoracostomy device of claim 1, wherein the base is configured to attach to a body of a patient, wherein when in the deployed position, the needle assembly extends into the patient, and wherein the needle is configured to automatically detach from the needle assembly when the needle enters a pleural cavity of the patient.

7. The needle thoracostomy device of claim 1, wherein, when the needle thoracostomy device moves from the raised position to the deployed position, the needle thoracostomy device is configured to maintain the needle assembly at a constant angle relative to the base.

8. A needle thoracostomy device, comprising:
a base having a first end and a second end;
a lever having a first end and a second end, wherein the first end of the lever is hingedly coupled to the second end of the base; and
a needle assembly hingedly coupled to the second end of the lever and having a needle and a catheter, wherein the needle thoracostomy device is moveable between a stored position in which the lever and the needle assembly are adjacent the base, a raised position in which the lever is positioned at an oblique angle with respect to the base and the needle assembly extends between the lever and the base, and a deployed position in which the lever is adjacent the base and the needle assembly extends below the base;
wherein the base is configured to attach to a body of a patient, wherein when in the deployed position, the needle assembly extends into the patient, and wherein the needle is configured to automatically detach from the needle assembly when the needle enters a pleural cavity of the patient.

9. The needle thoracostomy device of claim 8, further comprising a venting system configured to automatically fluidly couple with the catheter upon removal of the needle from the needle assembly.

10. The needle thoracostomy device of claim 8, further comprising a venting system having an outlet and a primary valve configured to drain fluid from the catheter to the outlet and restrict fluid flow from the outlet to the catheter.

11. The needle thoracostomy device of claim 8, further comprising a venting valve positioned adjacent the second end of the lever, the venting valve having a first port and a second port, wherein the venting valve is configured to rotate between a needle position in which the first port is aligned with the catheter and a draining position in which the second port is aligned with the catheter, wherein the venting valve fluidly couples the catheter to a venting system when in the draining position.

12. The needle thoracostomy device of claim 11, wherein the needle is removable from the needle assembly through the first port and wherein the venting valve is biased toward the draining position such that the venting valve automatically rotates to the draining position upon removal of the needle from the first port.

13. The needle thoracostomy device of claim 8, wherein, when the needle thoracostomy device moves from the raised position to the deployed position, the needle thoracostomy device is configured to maintain the needle assembly at a constant angle relative to the base.

14. A needle thoracostomy device, comprising:
a base having a first end and a second end;
a lever having a first end and a second end, wherein the first end of the lever is hingedly coupled to the second end of the base; and
a needle assembly hingedly coupled to the second end of the lever and having a needle and a catheter, wherein the needle thoracostomy device is moveable between a stored position in which the lever and the needle assembly are adjacent the base, a raised position in which the lever is positioned at an oblique angle with respect to the base and the needle assembly extends between the lever and the base, and a deployed position in which the lever is adjacent the base and the needle assembly extends below the base.

15. The needle thoracostomy device of claim 14, further comprising a venting system configured to automatically fluidly couple with the catheter upon removal of the needle from the needle assembly.

16. The needle thoracostomy device of claim 14, further comprising a venting system having an outlet and a primary valve configured to drain fluid from the catheter to the outlet and restrict fluid flow from the outlet to the catheter.

17. The needle thoracostomy device of claim 16, wherein the venting system comprises a secondary valve configured to allow fluid from the catheter to bypass the primary valve.

18. The needle thoracostomy device of claim 14, further comprising a venting valve positioned adjacent the second end of the lever, the venting valve having a first port and a second port, wherein the venting valve is configured to rotate between a needle position in which the first port is aligned with the catheter and a draining position in which the second port is aligned with the catheter, wherein the venting valve fluidly couples the catheter to a venting system when in the draining position.

19. The needle thoracostomy device of claim 18, wherein the needle is removable from the needle assembly through the first port and wherein the venting valve is biased toward the draining position such that the venting valve automatically rotates to the draining position upon removal of the needle from the first port.

20. The needle thoracostomy device of claim 14, wherein, when the needle thoracostomy device moves from the raised position to the deployed position, the needle thoracostomy device is configured to maintain the needle assembly at a constant angle relative to the base.

\* \* \* \* \*